(12) United States Patent
Bobbitt et al.

(10) Patent No.: US 11,806,052 B2
(45) Date of Patent: Nov. 7, 2023

(54) SPINAL CORRECTION SYSTEM AND METHOD

(71) Applicant: WARSAW ORTHOPEDIC INC., Warsaw, IN (US)

(72) Inventors: Dustin Bobbitt, Olive Branch, MS (US); Ian J. Harding, Bristol (GB); Tyler R. Koski, Wilmette, IL (US); Lawrence G. Lenke, New York, NY (US); Ronald A. Lehman, Jr., Englewood, NJ (US); Russell P. Nockels, Chicago, IL (US); David A. Mire, Collierville, TN (US); Christopher Shaffrey, Charlottesville, VA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 214 days.

(21) Appl. No.: 17/362,318

(22) Filed: Jun. 29, 2021

(65) Prior Publication Data

US 2021/0322066 A1 Oct. 21, 2021

Related U.S. Application Data

(60) Division of application No. 15/940,231, filed on Mar. 29, 2018, now Pat. No. 11,051,859, which is a
(Continued)

(51) Int. Cl.
*A61B 17/70* (2006.01)
*A61B 17/02* (2006.01)
*A61B 17/68* (2006.01)

(52) U.S. Cl.
CPC ........ *A61B 17/7077* (2013.01); *A61B 17/025* (2013.01); *A61B 17/7002* (2013.01);
(Continued)

(58) Field of Classification Search
CPC ................ A61B 17/66; A61B 17/6458; A61B 2017/681; A61B 17/808
(Continued)

(56) References Cited

U.S. PATENT DOCUMENTS

| 776,051 A | 11/1904 | Fruehling |
| 1,920,821 A | 8/1933 | Wassenaar |

(Continued)

FOREIGN PATENT DOCUMENTS

| DE | 3414374 C2 | 10/1985 |
| DE | 3807346 C1 | 6/1989 |

(Continued)

OTHER PUBLICATIONS

U.S. Appl. No. 15/139,395, filed Apr. 27, 2016; Bobbitt, et al.; Spinal Correction System and Method.
(Continued)

*Primary Examiner* — Eduardo C Robert
*Assistant Examiner* — Tara Rose E Carter
(74) *Attorney, Agent, or Firm* — Sorell, Lenna & Schmidt, LLP

(57) ABSTRACT

A method includes providing first and second instruments. First and second fasteners are attached with vertebrae. First fasteners are connected with first and second constructs. Second fasteners are connected with a third and fourth constructs. The first construct is connected with a body of the first instrument and the second construct is connected with another body of the first instrument. The third construct is connected with a body of the second instrument and the fourth construct is connected with another body of the second instrument. Joints of the instruments are tightened. At least one of the instruments is selectively distracted. At least one of the instruments is selectively compressed. The spinal constructs are removed from the fasteners. The first
(Continued)

fasteners are connected with a first spinal rod. The second fasteners are connected with a second spinal rod. In some embodiments, spinal constructs, implants, systems and kits are disclosed.

20 Claims, 35 Drawing Sheets

Related U.S. Application Data continuation-in-part of application No. 15/139,406, filed on Apr. 27, 2016, now Pat. No. 10,194,958.

(52) U.S. Cl.
CPC ...... *A61B 17/7032* (2013.01); *A61B 17/7079* (2013.01); *A61B 2017/0256* (2013.01); *A61B 2017/681* (2013.01)

(58) Field of Classification Search
USPC .......................... 606/250–279, 86 a
See application file for complete search history.

(56) References Cited

U.S. PATENT DOCUMENTS

| | | | |
|---|---|---|---|
| 4,957,495 A | 9/1990 | Kluger | |
| 5,219,349 A | 6/1993 | Krag et al. | |
| 7,416,553 B2 | 8/2008 | Patel et al. | |
| 7,578,822 B2 | 8/2009 | Rezach et al. | |
| 7,618,424 B2 | 11/2009 | Wilcox et al. | |
| 7,655,008 B2 | 2/2010 | Lenke et al. | |
| 7,794,464 B2 | 9/2010 | Bridwell et al. | |
| 7,914,536 B2 | 3/2011 | MacDonald et al. | |
| 7,922,731 B2 | 4/2011 | Schumacher et al. | |
| 8,157,806 B2 | 4/2012 | Frigg et al. | |
| 8,206,395 B2 | 6/2012 | McLean et al. | |
| 8,277,453 B2 | 10/2012 | Kave et al. | |
| 8,287,546 B2 | 10/2012 | King et al. | |
| 8,394,109 B2 | 3/2013 | Hutton et al. | |
| 9,345,517 B2 * | 5/2016 | Zhang | A61B 17/8863 |
| 2004/0034298 A1 | 2/2004 | Johnson et al. | |
| 2005/0021040 A1 | 1/2005 | Bertagnoli | |
| 2008/0119862 A1 | 5/2008 | Wicker et al. | |
| 2009/0062857 A1 | 3/2009 | Ramsay et al. | |
| 2010/0137920 A1* | 6/2010 | Hammill, Sr. | A61B 17/7037 606/308 |
| 2010/0246923 A1 | 9/2010 | Nathaniel et al. | |
| 2011/0172662 A1 | 7/2011 | Keilen | |
| 2011/0319939 A1 | 12/2011 | Kretzer et al. | |
| 2012/0071885 A1 | 3/2012 | Forton et al. | |
| 2017/0311985 A1 | 11/2017 | Bobbitt et al. | |
| 2017/0311987 A1 | 11/2017 | Bobbitt et al. | |

FOREIGN PATENT DOCUMENTS

| | | |
|---|---|---|
| EP | 316371 B1 | 10/1991 |
| EP | 528177 A2 | 2/1993 |
| EP | 1590077 B1 | 11/2005 |
| WO | 9002527 A1 | 3/1990 |
| WO | 2004014231 A1 | 2/2004 |
| WO | 2005107415 A2 | 11/2005 |
| WO | 2006094754 A1 | 9/2006 |
| WO | 2006118998 A1 | 11/2006 |
| WO | 2007092797 A2 | 8/2007 |
| WO | 2008155772 A1 | 12/2008 |

OTHER PUBLICATIONS

U.S. Appl. No. 15/139,406, filed Apr. 27, 2016; Bobbitt, et al.; Spinal Correction System and Method.

* cited by examiner

SPINAL CORRECTION SYSTEM AND METHOD

CROSS-REFERENCE TO RELATED APPLICATIONS

This application is a divisional of U.S. patent application Ser. No. 15/940,231, filed Mar. 29, 2018, which is a continuation-in-part of U.S. patent application Ser. No. 15/139,406, filed Apr. 27, 2016, now U.S. Pat. No. 10,194,958. These applications are expressly incorporated herein by reference, in their entireties.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, corpectomy, discectomy, laminectomy, fusion, fixation and implantable prosthetics. Correction treatments used for positioning and alignment of vertebrae may employ implants, such as, for example, spinal constructs and interbody devices, for stabilization of a treated section of a spine. In some cases, the spinal constructs may be manipulated with surgical instruments for compression and distraction of vertebrae. This disclosure describes an improvement over these prior technologies.

SUMMARY

In one embodiment, a method for treating a spine is provided. The method comprises the steps of: providing a first surgical instrument and a second surgical instrument, the surgical instruments each including a first arm and a second arm, the arms each having a first part and a body that is movably connected to the first part at a first joint; attaching first fasteners with vertebrae; attaching second fasteners with the vertebrae; connecting two of the first fasteners with a first spinal construct and two of the first fasteners with a second spinal construct; connecting two of the second fasteners with a third spinal construct and two of the second fasteners with a fourth spinal construct; connecting the first spinal construct with one of the bodies of the first surgical instrument and connecting the second spinal construct with the other one of the bodies of the first surgical instrument; connecting the third spinal construct with one of the bodies of the second surgical instrument and connecting the fourth spinal construct with the other one of the bodies of the second surgical instrument; tightening the first joints to lock the bodies relative to the first parts; selectively distracting at least one of the surgical instruments; selectively compressing at least one of the surgical instruments; removing the spinal constructs from the fasteners; connecting the first fasteners with a first spinal rod; and connecting the second fasteners with a second spinal rod.

In one embodiment, a method for treating a spine is provided. The method comprises the steps of: providing a first surgical instrument and a second surgical instrument, the surgical instruments each including a first arm and a second arm, the arms each having a first part that is movably connected to a sleeve at a first joint; attaching first fasteners with vertebrae; attaching second fasteners with the vertebrae; connecting the sleeves of the first surgical instrument with the first fasteners such that the sleeves of the first surgical instrument directly engage the first fasteners; connecting the sleeves of the second spinal construct with the second fasteners such that the sleeves of the second surgical instrument directly engage the second fasteners; tightening the first joints to lock a respective one of the first parts relative to a respective one of the second parts; selectively distracting at least one of the surgical instruments; selectively compressing at least one of the surgical instruments; removing the sleeves from the fasteners; connecting the first fasteners with a first spinal rod; and connecting the second fasteners with a second spinal rod.

In one embodiment, kit for treating a spine is provided. The kit comprises a first controller, a second controller, a plurality of bone fasteners, a plurality of temporary spinal rods and a plurality of permanent spinal rods. The controllers each include: a longitudinal element; a first arm connected with the longitudinal element and including a body engageable with a first spinal construct, the body being rotatable relative to the first arm in a first orientation and a second orientation, the body including a lock to fix the body relative to the first arm; and a second arm being axially translatable relative to the first arm and including a body engageable with a second spinal construct, the body of the second arm being rotatable relative to the second arm in a first orientation and a second orientation, the body of the second arm including a lock to fix the body of the second arm relative to the second arm. In some embodiments, the kit does not include temporary spinal rods or permanent spinal rods. In some embodiments, the kit includes an adjacent set that goes with a controller set, the adjacent set being separate from the controller set.

BRIEF DESCRIPTION OF THE DRAWINGS

The present disclosure will become more readily apparent from the specific description accompanied by the following drawings, in which.

DETAILED DESCRIPTION

Figure 1:
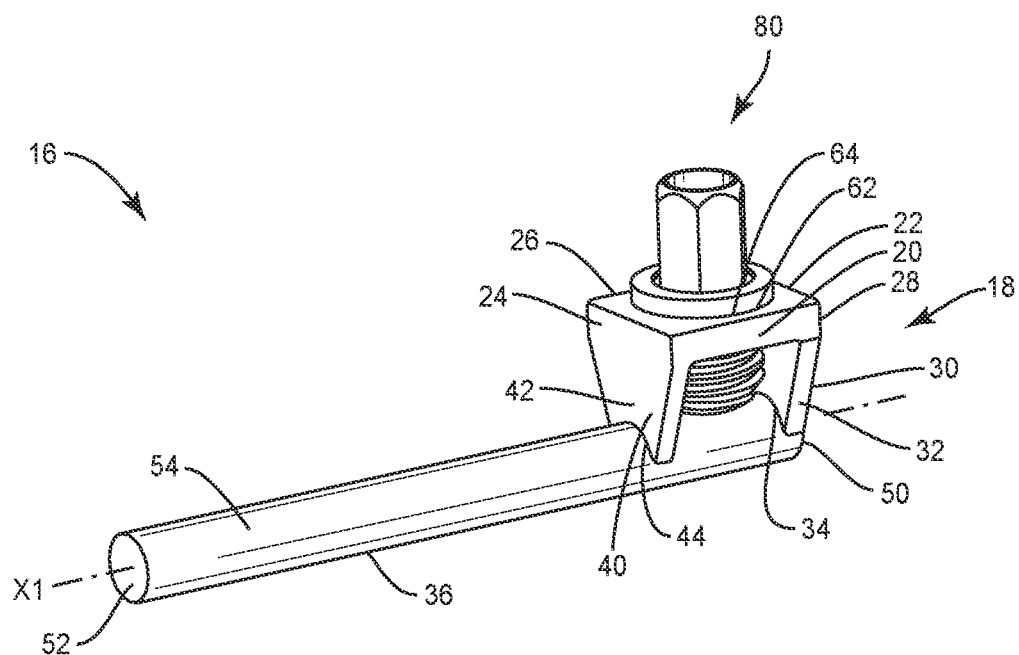
FIG. 1 is a perspective view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system comprises a spinal construct that can be employed with one or more surgical instruments for a pedicle subtraction osteotomy (PSO). In some embodiments, the present surgical system can be employed with a posterior vertebral column resection to correct angular and fixed kyphotic deformity, such as post traumatic deformity, congenital deformity and/or post infectious deformity.

In some embodiments, the present surgical system comprises a spinal construct that can be employed with one or more surgical instruments for three column manipulation of vertebrae. In some embodiments, the present surgical system comprises a spinal construct that can be employed with one or more surgical instruments for compressing, distracting or otherwise manipulating the spine. In some embodiments, the spinal construct is configured to spread an applied load to multiple bone screws to avoid pedicle screw plow and/or bone fracture. In some embodiments, the spinal construct comprises a connector that quickly and effectively bridges two screws in-situ while maintaining a low profile for improved visualization.

In some embodiments, the present surgical system includes connectors that lock onto bone screws and a rod by engaging a surgical inserter instrument into a rod slot of the bone screws. In some embodiments, the present surgical system is employed with a method that facilitates applying the connectors to the bone screws. In some embodiments, the surgical instruments can be quickly clicked on and off of the connectors. In some embodiments, the present surgical system is configured to provide surgeons with an efficient way to share load between bone screws and reduce the occurrence of screw plow and the resulting risk of bone fracture, screw toggle and screw pull out.

In some embodiments, the present surgical system is employed with a method that includes the steps of inserting bone screws in two vertebrae above and two vertebrae below a PSO site. In some embodiments, the present surgical system can include multi-axial screws (MAS) and/or dual rod multi-axial screws (DRMAS). In some embodiments, the method includes the step of attaching a rod instrument with an integrated set screw to a bone screw. The set screw attaches the rod instrument proximal to the PSO. In some embodiments, the method includes the step of securing an instrument with an integrated set screw to a distal end of the rod instrument. In some embodiments, the method includes the step of attaching a rack distractor/compressor with numerous motion points to the spinal construct. In some embodiments, the method includes the step of locking all motion points to secure the spine. In some embodiments, the present surgical system can include various instruments. In some embodiments, an angle indicating osteotome can be used to guide a cut angle of selected vertebrae. In some embodiments, the method includes the step of placing an intrabody implant in the PSO to preserve anterior height, maintain alignment of the two sides of the PSO and act as a fulcrum for closure. In some embodiments, the method includes the step of setting the rack to compression and unlocking one of the motion points to allow the spine to pivot at the PSO during closure.

In some embodiments, the present surgical system comprises a spinal construct that includes a connector body, a connector collar, a connector shaft, connector legs, connector feet and a rod. In some embodiments, the present surgical system comprises a surgical instrument that includes a driver, a sleeve and a spring latch. In some embodiments, the surgical instrument comprises an inserter that includes a sleeve and a driver assembly that slides over the spinal construct. In some embodiments, the surgical instrument comprises spring loaded latches that retain the connector body in the sleeve. In some embodiments, the inserter sleeve fits into a rod slot of a bone screw to orient a head of the bone screw.

In some embodiments, the present surgical system is employed with a method of attaching the surgical instrument with the spinal construct including the steps of pushing the driver toward the bone screw such that it translates through the sleeve and drives the connector collar down the legs. In some embodiments, a change in the connector leg profile causes the legs to close when the collar is down, and open when the collar is in an up position. In some embodiments, the connector is spring loaded to an open position such that the legs close and engage slots on the sides of the screw head. As such, the collar can translate down the legs and engage the rod to bind the rod between the sleeve and the connector feet. In some embodiments, the driver is rotated to thread the connector shaft into the connector body. This configuration locks the legs and the rod.

In some embodiments, the spring latches are engaged to remove the inserter from the spinal construct. In some embodiments, this engagement binds the screw heads in 5 of 6 degrees of freedom such that the screw heads are free to roll in a medial lateral direction. In some embodiments, surgical instruments can now click onto the spinal construct using the sleeve and spring latch quick connect engagement. In some embodiments, a distractor/compressor connects two spinal constructs to stabilize and manipulate the spine during a PSO procedure.

In some embodiments, the present surgical system includes a surgical instrument that can compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, ankylosing spondylitis. In some embodiments, the present surgical system is employed to treat hyper-kyphosis, flat lumbar back and cervical hyper lordosis, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

In some embodiments, the present surgical system is employed with a method that includes the steps of providing two surgical instruments, such, as for example, two controllers. The controllers are each provided with joints of the controllers in an open and/or loose configuration. In some embodiments, the method includes ensuring that all joints are in the open and/or loose configuration and loosening any joints that are not in the open and/or loose configuration.

In some embodiments, spinal constructs, such as, for example, temporary rods or temporary installment bars are attached with implanted screws. The screws can include one or more MAS and/or one or more DRMAS. In some embodiments, first screws are implanted along a lateral side of vertebrae and second screws are implanted along a contralateral side of the vertebrae. A first arm of the first controller is attached to a first pair of the first screws and a second arm of the first controller is attached to a second pair of the first screws. A first arm of the second controller is attached to a first pair of the second screws and a second arm of the second controller is attached to a second pair of the second screws.

In some embodiments, the screws are attached to the arms of the controllers. In some embodiments, the arms are attached to the screws by attaching sleeves of the controllers to implant components, such as, for example, the spinal constructs. In some embodiments, the arms are attached to the screws by attaching sleeves of the controllers directly to the screws. In some embodiments, the controllers are each connected directly to multiple vertebral levels. In some embodiments, the arms are connected to screws implanted, or to be implanted, in the farthest separated vertebrae. For example, when five vertebral levels are affected, the arms would be connected to screws implanted in the first and fifth vertebrae. This can provide the surgeon with more room in which to operate, including more room for manipulating the controllers and/or more room for performing related work, such as, for example, vertebral body removal and/or disc removal.

In some embodiments, first level joints of the controllers are tightened, while ensuring that the vertebrae are positioned as desired. In some embodiments, the first level joints are a distalmost joint of each of the controllers. In some embodiments, second level joints of the controllers are tightened, while ensuring that the vertebrae are positioned as desired. In some embodiments, third level joints of the controllers are tightened, while ensuring that the vertebrae are positioned as desired. In some embodiments, rack locks of the controllers are tightened, while ensuring that the vertebrae are positioned as desired.

In some embodiments, the vertebrae are distracted after at least one of the joints and/or the rack locks are tightened. In some embodiments, the vertebrae are distracted using a rack mechanism of at least one of the controllers.

In some embodiments, a surgical procedure, such as, for example, discectomy, laminectomy, fusion, laminotomy, laminectomy, nerve root retraction, foraminotomy, facetectomy, decompression, spinal nucleus or disc replacement is performed after the vertebrae are distracted.

In some embodiments, the vertebrae are distracted after the surgical procedure is performed to better accommodate an interbody implant. In some embodiments, the vertebrae are distracted using a rack mechanism of at least one of the controllers. In some embodiments, the interbody implant is relatively large or is specially designed. For example, in some embodiments, the interbody implant has a fore-aft or lateral height taper. In some embodiments, the vertebrae are distracted using one of the controllers and not the other controller. In some embodiments, the vertebrae are distracted using one of the controllers more than the other controller. In some embodiments, the vertebrae are distracted by one of the controllers and are compressed by the other controller. In some embodiments, adjustments to the vertebrae are accomplished using a rack mechanism of at least one of the controllers and/or adjusting one or more of the joints.

In some embodiments, a second surgical procedure, such as, for example, discectomy, laminectomy, fusion, laminotomy, laminectomy, nerve root retraction, foraminotomy, facetectomy, decompression, spinal nucleus or disc replacement is performed after the surgical procedure is performed and the vertebrae are distracted.

In some embodiments, the vertebrae are compressed after the second surgical procedure is performed to assist/cause the vertebrae to locate as desired to post-operation positioning, which may include assisting/causing the vertebrae to capture or more robustly engage the implant as desired, for example, at a preferred angle, or with a desired force. In some embodiments, the vertebrae are compressed using a rack mechanism of at least one of the controllers. In some embodiments, the vertebrae are compressed using one of the controllers and not the other controller. In some embodiments, the vertebrae are compressed using one of the controllers more than the other controller. In some embodiments, the vertebrae are distracted by one of the controllers and are compressed by the other controller. In some embodiments, adjustments to the vertebrae are accomplished using a rack mechanism of at least one of the controllers and/or adjusting one or more of the joints.

The controllers are removed from the screws. In embodiments that include using the spinal constructs, the spinal constructs are removed from the screws. After the controllers are removed and the spinal constructs, if used, are removed, a first permanent spinal rod is installed with each of the first screws and a second permanent spinal rod is installed with each of the second screws.

In some embodiments, the present surgical system is employed with a method that includes a plurality of steps, wherein steps may be added, omitted, or performed in any order. For example, in some embodiments, a user can attach sleeves of a first controller to a first pair of screws, then proceed to tighten joint(s) of the second controller, before tightening second level joints of the first controller. In some embodiments, first level joint(s) of the first controller is/are tightened, and first level joint(s) of the second controller is/are tightened before tightening second level joints of the first controller. In some embodiments, first level joint(s) of the first controller is/are tightened and at least one of the first level joints of the second controller are tightened before tightening first level joints of the first controller. In some embodiments, first level joint(s) of the first controller is/are tightened and at least one of the first level joints of the second controller are tightened before tightening second level joints of the first controller.

In some embodiments, one or more surgical procedure, such as, for example, removing one or more vertebrae, removing one or more vertebral body, removing one or more vertebral disc and implanting an interbody implant is/are performed before and/or after the vertebrae are distracted and/or contracted. For example, in some embodiments, at least one of the surgical procedures is performed. The vertebrae are then distracted after at least one of the surgical procedures is performed. At least one of the surgical procedures is then performed after the vertebrae are distracted. The vertebrae are then distracted a second time after at least one of the surgical procedures is performed. At least one of the surgical procedures is then performed after the vertebrae are distracted for the second time. The vertebrae are then contracted. At least one of the surgical procedures is then performed after the vertebrae are contracted.

In some embodiments, at least one of the surgical procedures is performed. The vertebrae are then distracted after at least one of the surgical procedures is performed. At least one of the surgical procedures is then performed after the vertebrae are distracted. At least one of the joints is tightened and/or loosened after at least one of the surgical procedures is performed. At least one of the surgical procedures is then performed after at least one of the surgical procedures is performed. The vertebrae are then contracted. At least one of the surgical procedures is then performed after the vertebrae are contracted.

In some embodiments, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
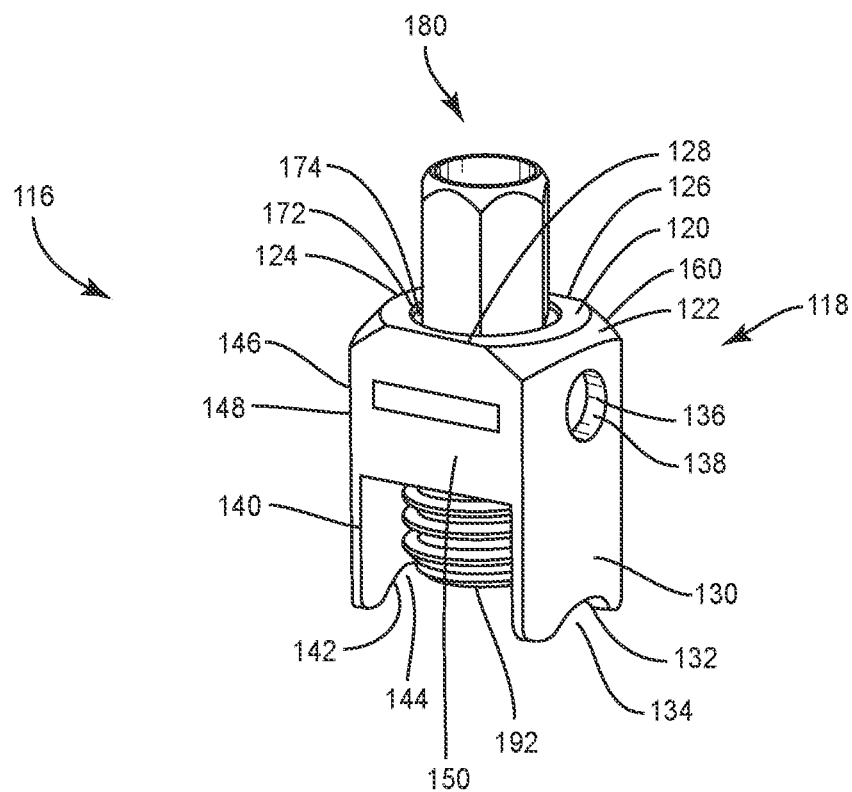
FIG. 2 is a perspective view of components of one embodiment of a surgical system in accordance with the principles of the present disclosure.

The following discussion includes a description of a surgical system and related methods of employing the surgical system in accordance with the principles of the present disclosure. Alternate embodiments are also disclosed. Reference is made to the exemplary embodiments of the present disclosure, which are illustrated in the accompanying figures. Turning to FIGS. 1 and 2, there are illustrated components of a surgical system, such as, for example, a spinal correction system 10.

The components of spinal correction system 10 can be fabricated from biologically acceptable materials suitable for medical applications, including metals, synthetic polymers, ceramics and bone material and/or their composites. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKEL-ITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal correction system 10 are configured for engagement with spinal constructs attached with vertebrae to manipulate tissue and/or correct a spinal disorder, such as, for example, a sagittal deformity, as described herein. In some embodiments, spinal correction system 10 may be employed with surgical procedures, such as, for example, corpectomy, discectomy and/or fracture/trauma treatment and may include fusion and/or fixation that employ implants to restore the mechanical support function of vertebrae.

Spinal correction system 10 includes a spinal construct, such as, for example, a connector 12. Connector 12 is engageable with bone fasteners and a surgical instrument to manipulate tissue, as described herein. Connector 12 includes a member 16 and a member 116. Member 16 includes a body, such as, for example, a support 18. Support 18 includes a wall 20 that extends between an end 22 and an end 24. Wall 20 includes a surface 26 and a surface 28 that extend between ends 22, 24. Wall 20 extends parallel to an axis X1 defined by a longitudinal element, such as, for example, a rod 36, as described herein. In some embodiments, wall 20 may extend in alternate configurations, for example, arcuate, offset, staggered and/or angled portions.

Wall 20 includes an extension, such as, for example, a leg 30. Leg 30 extends from end 22. Leg 30 is oriented substantially perpendicular to axis X1. In some embodiments, leg 30 may be variously oriented relative to axis X1, such as, for example, transverse and/or angled. Leg 30 includes a tapered configuration to facilitate engagement with a receiver of a fastener, as described herein.

Leg 30 includes a surface 32 that defines a recess 34. Recess 34 is arcuate to facilitate engagement with rod 36. In some embodiments, leg 30 is monolithically formed with rod 36. In some embodiments, leg 30 is attached with rod 36 via clips, hooks, adhesives and/or flanges. In some embodiments, surface 32 is smooth or even. In some embodiments, surface 32 may be rough, textured, porous, semi-porous, dimpled and/or polished.

Wall 20 includes an extension, such as, for example, a leg 40 disposed in spaced apart relation to leg 30. Leg 40 extends from end 24. Leg 40 is oriented substantially perpendicular to axis X1. In some embodiments, leg 40 may be variously oriented relative to axis X1, such as, for example, transverse and/or angled. Leg 40 includes a tapered configuration configured to facilitate engagement with a receiver of a fastener, as described herein.

Leg 40 includes a surface 42 that defines a recess 44. Recess 44 is arcuate to facilitate engagement with rod 36. In some embodiments, leg 40 is monolithically formed with rod 36. In some embodiments, leg 40 is attached with rod 36 via clips, hooks, adhesives and/or flanges. In some embodiments, surface 42 is smooth or even. In some embodiments, surface 42 may be rough, textured, porous, semi-porous, dimpled and/or polished.

Rod 36 extends between an end 50 and an end 52 defining axis X1, as described herein. Rod 36 includes a surface 54 configured for engagement with a coupling member of support 116, as described herein. In some embodiments, rod 36 is configured to connect the receiver of one fastener with the receiver of an adjacent fastener to connect members 16, 116, as described herein.

Wall 20 includes an inner surface 62 that defines a cavity 64 extending between surfaces 26, 28. Cavity 64 is configured for disposal of a coupling member, such as, for example, a set screw 80. In some embodiments, set screw 80 is integrally connected with member 16. Set screw 80 is configured to fix support 16 and rod 36 with the receiver of a bone fastener, as described herein.

Connector 12 includes a member 116. Member 116 includes a body, such as, for example, a support 118. Support 118 includes a wall 120 that extends between an end 122 and an end 124. Wall 120 includes a surface 126 and a surface 128 that extend between ends 122, 124. In some embodiments, wall 120 may extend in alternate configurations between ends 122, 124, such as, for example, linear, arcuate, offset, staggered and/or angled portions.

Wall 120 includes an extension, such as, for example, a leg 130. Leg 130 extends from end 122. Leg 130 is oriented substantially perpendicular to axis X1. In some embodiments, leg 130 may be variously oriented relative to axis X1, such as, for example, transverse and/or angled, which may include acute and obtuse orientations. In some embodiments, leg 130 may have various configurations, for example, round, oval, rectangular, tapered, polygonal, irregular, offset, staggered, uniform and non-uniform.

Leg 130 includes a surface 132 that defines a recess 134. Recess 134 is configured for engagement with rod 36 to facilitate connection of member 16 with member 116 and adjacent bone fasteners, as described herein. In some embodiments, the geometry of recess 134 may be arcuate to facilitate engagement with rod 36. In some embodiments, surface 132 is smooth or even. In some embodiments, surface 132 may be rough, textured, porous, semi-porous, dimpled and/or polished.

Leg 130 includes a surface 136 that defines a mating element, such as, for example, a detent 138. Detent 138 is configured for a mating engagement with various surgical instruments in a quick release configuration to facilitate the interchangeability of connector 12 with surgical instruments, as described herein. In some embodiments, detent 138 includes a circular configuration. In some embodiments the cross section geometry of detent 138 may have various configurations, such as, for example, oval, oblong, triangular, polygonal having planar or arcuate side portions, irregular, uniform, non-uniform, consistent, variable, horseshoe shape, U-shape or kidney bean shape. In some embodiments, surface 136 may have alternate surface configurations, such as, for example, rough, threaded for connection with surgical instruments, arcuate, undulating, porous, semi-porous, dimpled, polished and/or textured. Detents 138 are configured for releasable engagement with a surgical instrument to manipulate tissue such that movement of the receiver relative to a shaft of the fastener is resisted and/or prevented.

Wall 120 includes an extension, such as, for example, a leg 140, disposed in a spaced apart relation with leg 130. In some embodiments, leg 140 extends from end 124. Leg 140 is oriented substantially perpendicular to axis X1. In some embodiments, leg 140 may be variously oriented relative to axis X1, such as, for example, transverse and/or angled.

Leg 140 includes a surface 142 that defines a recess 144. Recess 144 is arcuate to facilitate engagement with rod 36. In some embodiments, surface 142 is smooth or even. In some embodiments, surface 142 may be rough, textured, porous, semi-porous, dimpled and/or polished.

Leg 140 includes a surface 146 that defines a mating element, such as, for example, a detent 148. Detent 148 is configured for a mating engagement with various surgical instruments in a quick release configuration, as described herein, to facilitate the interchangeability of connector 12 with surgical instruments, as described herein. In some embodiments, detent 148 includes a circular configuration. In some embodiments, detent 148 may have various configurations, such as, for example, oval, oblong, triangular, polygonal having planar or arcuate side portions, irregular, uniform, non-uniform, consistent, variable, horseshoe shape, U-shape or kidney bean shape. In some embodiments, surface 146 may have alternate configurations, such as, for example, rough, threaded for connection with surgical instruments, arcuate, undulating, porous, semi-porous, dimpled, polished and/or textured.

Wall 120 includes an extension 150. Extension 150 extends from wall 120 between ends 122, 124. Extension 150 connects legs 130, 140. Extension 150 is oriented substantially perpendicular to axis X1. In some embodiments, extension 150 may be variously oriented relative to axis X1, such as, for example, transverse and/or angled. Wall 120 includes an extension 160. Extension 160 extends from wall 120 between ends 122, 124 in a spaced apart relation relative to extension 150. Extension 160 connects legs 130, 140. Extension 160 is oriented substantially perpendicular to axis X1. In some embodiments, extension 160 may be variously oriented relative to axis X1, such as, for example, transverse and/or angled.

Wall 120 includes an inner surface 172 that defines an axial cavity 174 extending between surfaces 126, 128. Cavity 174 is configured for disposal of a coupling member, such as, for example, a set screw 180. In some embodiments, set screw 180 is integrally connected with member 116. Set screw 180 is configured to fix support 116 with the receiver of a bone fastener, as described herein. Set screw 180 includes a surface 192. Surface 192 is configured to engage a surface 54 of rod 36 to connect support 16 with support 116 forming connector 12.

Figure 3:
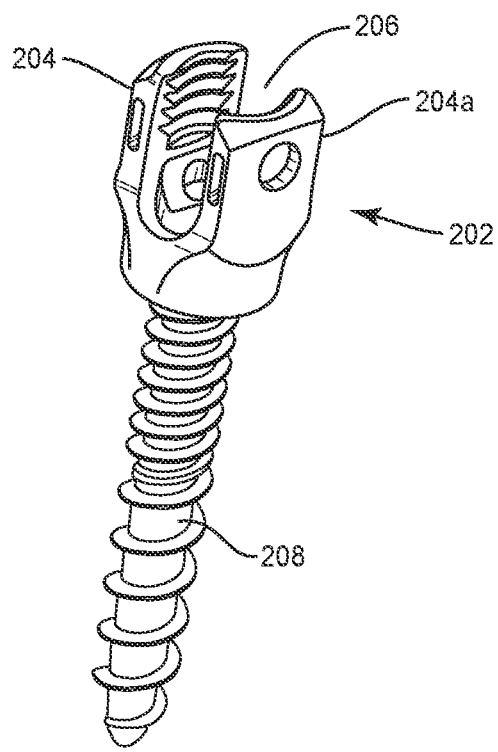
FIG. 3 is a perspective view of components of one embodiment of a surgical system in accordance with the principles of the present disclosure.

Spinal correction system 10 includes a bone fastener, such as, for example, a multi-axial screw (MAS) 200, as shown in FIG. 3. MAS 200 is configured for engagement with tissue, as described herein. MAS 200 includes a receiver 202 having a pair of spaced apart arms 204, 204a. Receiver 202 is configured for engagement with member 16 and/or member 116, as described herein.

Arms 204, 204a include an inner surface that defines a U-shaped passageway 206. Passageway 206 is configured for disposal of rod 36, as described herein. In some embodiments, all or only a portion of passageway 206 may have alternate cross section configurations, such as, for example, oval, oblong, triangular, square, polygonal, irregular, uniform, non-uniform, offset, staggered, and/or tapered. In some embodiments, arms 204, 204a may be disposed at alternate orientations, relative to a longitudinal axis of MAS 200, such as, for example, transverse, perpendicular and/or other angular orientations such as acute or obtuse, co-axial and/or may be offset or staggered.

The inner surface of receiver 202 includes a thread form configured for engagement with set screw 80 and/or set screw 180. Set screws 80, 180 are threaded with receiver 202 to attach, fix and/or lock member 16 and/or member 116 with MAS 200 attached with tissue to facilitate connection of the tissue with surgical instruments for correction treatment, as described herein.

MAS 200 includes a shaft 208 configured for penetrating tissue. Shaft 208 has a cylindrical cross-sectional configuration and includes an outer surface having an external thread form. In some embodiments, the external thread form may include a single thread or a plurality of discrete threads. In some embodiments, other engaging structures may be located on shaft 208, such as, for example, a nail configuration, barbs, expanding elements, raised elements and/or spikes to facilitate engagement of shaft 208 with tissue.

In some embodiments, all or only a portion of shaft 208 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 208 may include one or a plurality of openings. In some embodiments, all or only a portion of the outer surface of shaft 208 may have alternate surface configurations to enhance fixation with tissue, such as, for example, rough, arcuate, undulating, mesh, porous, semi-porous, dimpled and/or textured. In some embodiments, all or only a portion of shaft 208 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 208 may be cannulated.

Figure 4:
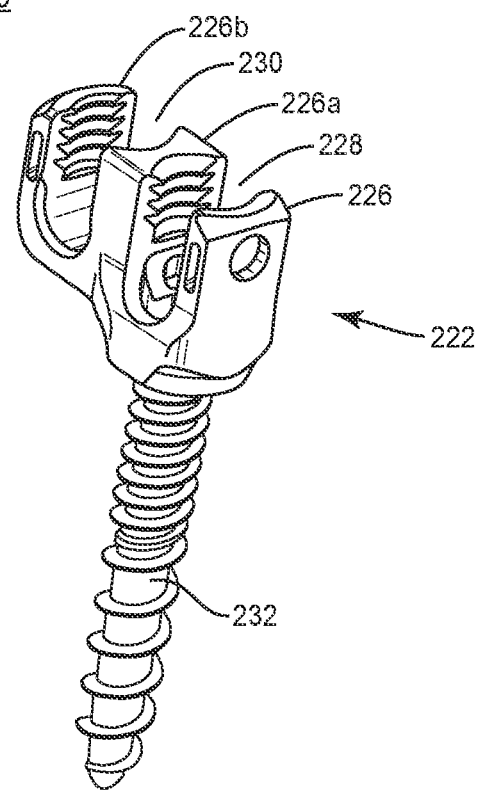
FIG. 4 is a perspective view of components of one embodiment of a surgical system in accordance with the principles of the present disclosure.

Spinal correction system 10 includes a bone fastener, such as, for example, a dual rod multi-axial screw (DRMAS) 220, as shown in FIG. 4. DRMAS 220 is configured for engagement with tissue, as described herein. DRMAS 220 includes a receiver 222. Receiver 222 includes a spaced apart arms 226, 226a, 226b. Arms 226, 226a include an inner surface that defines a U-shaped passageway 228. The inner surface of passageway 206 includes a thread form configured for engagement with set screws 80 and/or 180. Set screws 80, 180 are threaded with arms 226, 226a to attach, fix and/or lock member 16 and/or member 116 with receiver 222, as described herein. Spaced apart arms 226a, 226b include an inner surface that defines a U-shaped passageway 230 disposed adjacent to passageway 228. The inner surface of arms 226a, 226b includes a thread form configured for engagement with set screw 80 and/or set screw 180 to attach, fix and/or lock member 16 and/or member 116 with receiver 222.

MAS 220 includes a shaft 232, similar to shaft 208, configured for penetrating tissue. In some embodiments, one or more of the bone fasteners described herein can include posted screws, pedicle screws, uni-axial screws, side loading screws, sagittal adjusting screws, transverse sagittal adjusting screw, sagittal angulation screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. In some embodiments, one or more of the bone fasteners may be engaged with tissue in various orientations, such as, for example, series, parallel, offset, staggered and/or alternate vertebral levels.

Figure 5:
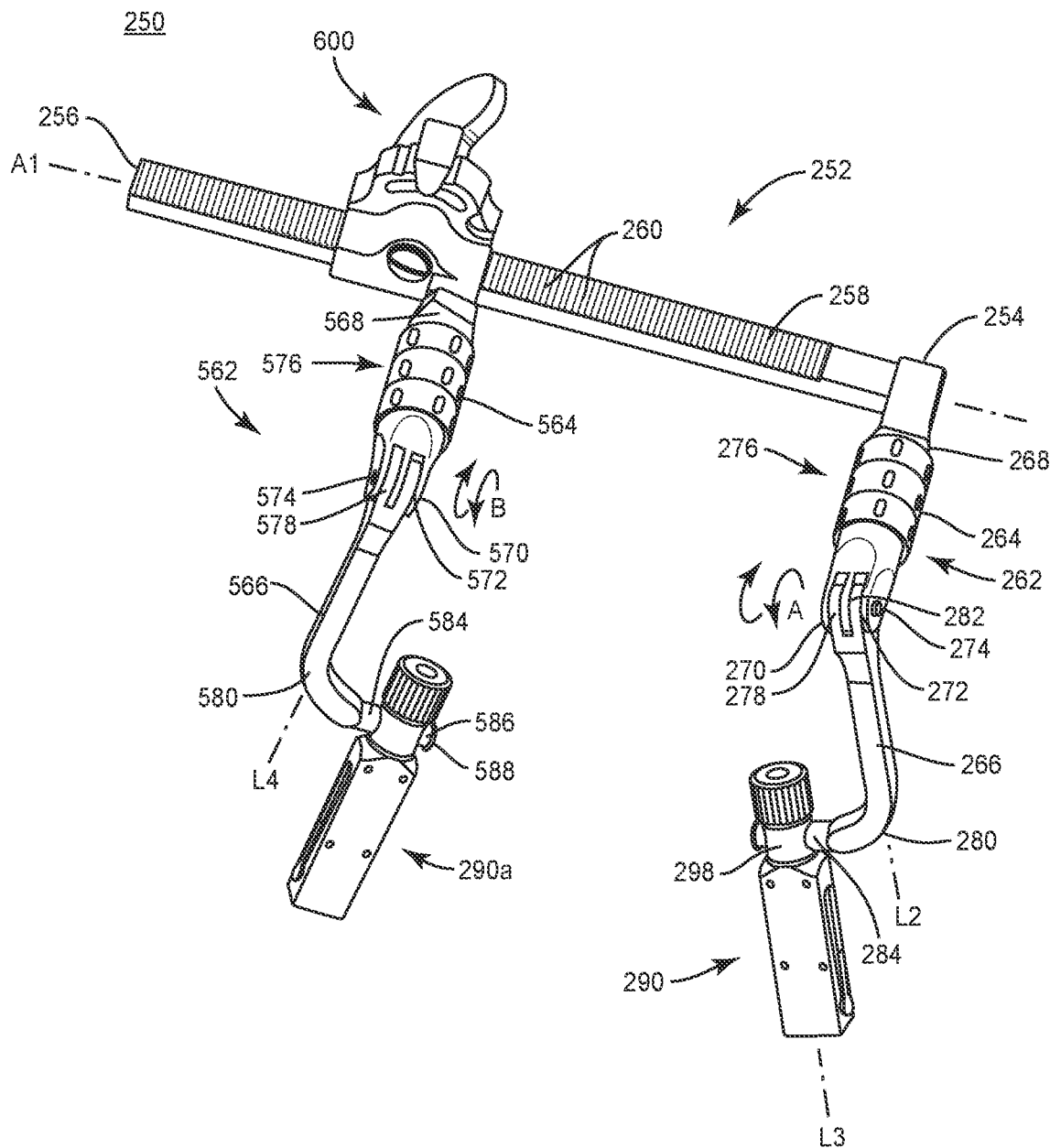
FIG. 5 is a perspective view of components of one embodiment of a surgical system in accordance with the principles of the present disclosure.

Spinal correction system 10 includes a surgical instrument, such as, for example, a compressor/distractor 250, as shown in FIG. 5. Compressor/distractor 250 includes a longitudinal element, such as, for example, a rack 252. Rack 252 extends between an end 254 and an end 256 defining a longitudinal axis A1. In some embodiments, rack 252 includes an outer surface 258 having a plurality of teeth, such as, for example, splines 260 engageable with an arm, as described herein.

Rack 252 includes an arm 262 extending from end 254. Arm 262 includes a part 264 and a part 266. Part 264 extends between an end 268 and an end 270. End 268 is configured for connection with rack 252. In some embodiments, part 264 is monolithically formed with rack 252. In some embodiments, end 268 is attached with rack 252 with, for example, clips, hooks, adhesives and/or flanges. In some embodiments, all or only a portion of part 264 may include cross section configurations, such as, for example, oval, oblong, triangular, square, polygonal, irregular, uniform, non-uniform, offset, staggered, undulating, arcuate, variable and/or tapered. In some embodiments, rack 252 and part 264 define a joint, such as, for example a third level joint of arm 262 configured to allow part 264 to pivot relative to rack 252 in the directions shown by arrows A in FIG. 5. Locking mechanism 276 may be manipulated to tighten the third level joint of arm 262 to fix part 264 relative to rack 252. Locking mechanism 276 may be manipulated to loosen the third level joint of arm 262 to allow part 264 to pivot relative to rack 252.

End 270 includes a surface that defines a cavity 272. Cavity 272 is configured for disposal of part 266. In some embodiments, cavity 272 includes a pin hinge 274 configured to facilitate a pivotable connection with part 266. Pin hinge 274 facilitates rotation of part 266 relative to part 264. Part 266 is configured to rotate relative to part 264, in the directions shown by arrows A in FIG. 5. In some embodiments, part 264 includes a locking mechanism 276 configured to fix part 266 relative to part 264. In some embodiments, hinge pin 274 defines a joint, such as, for example a second level joint of arm 262 configured to allow part 266 to pivot relative to part 264 in the directions shown by arrows A in FIG. 5. Locking mechanism 276 may be manipulated to tighten the second level joint of arm 262 to fix part 266 relative to part 264, as discussed herein. Locking mechanism 276 may be manipulated to loosen the second level joint of arm 262 to allow part 266 to pivot relative to part 264, as discussed herein.

Figure 6:
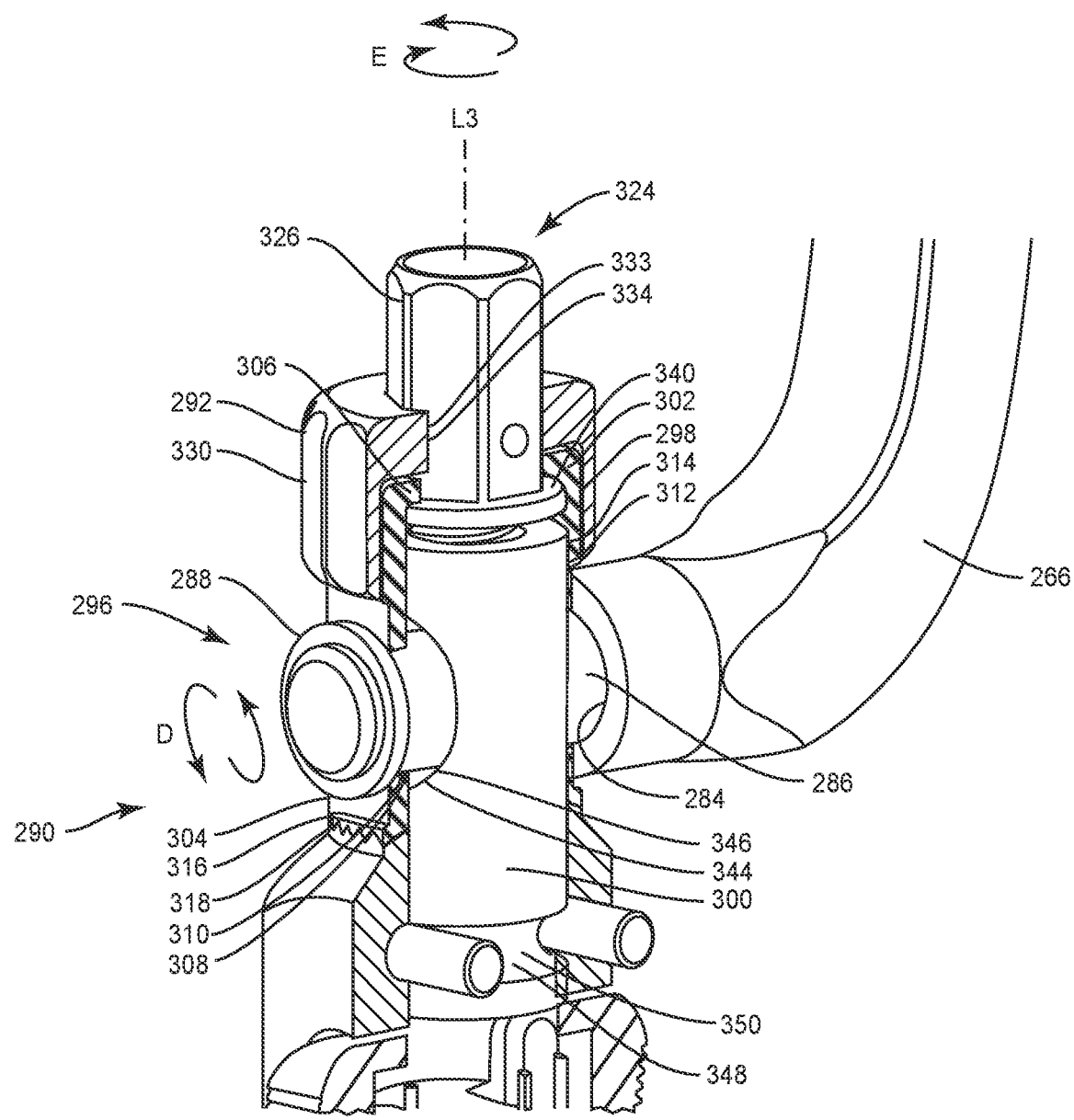
FIG. 6 is a cutaway view of components of the system shown in FIG. 5.
Figure 7:
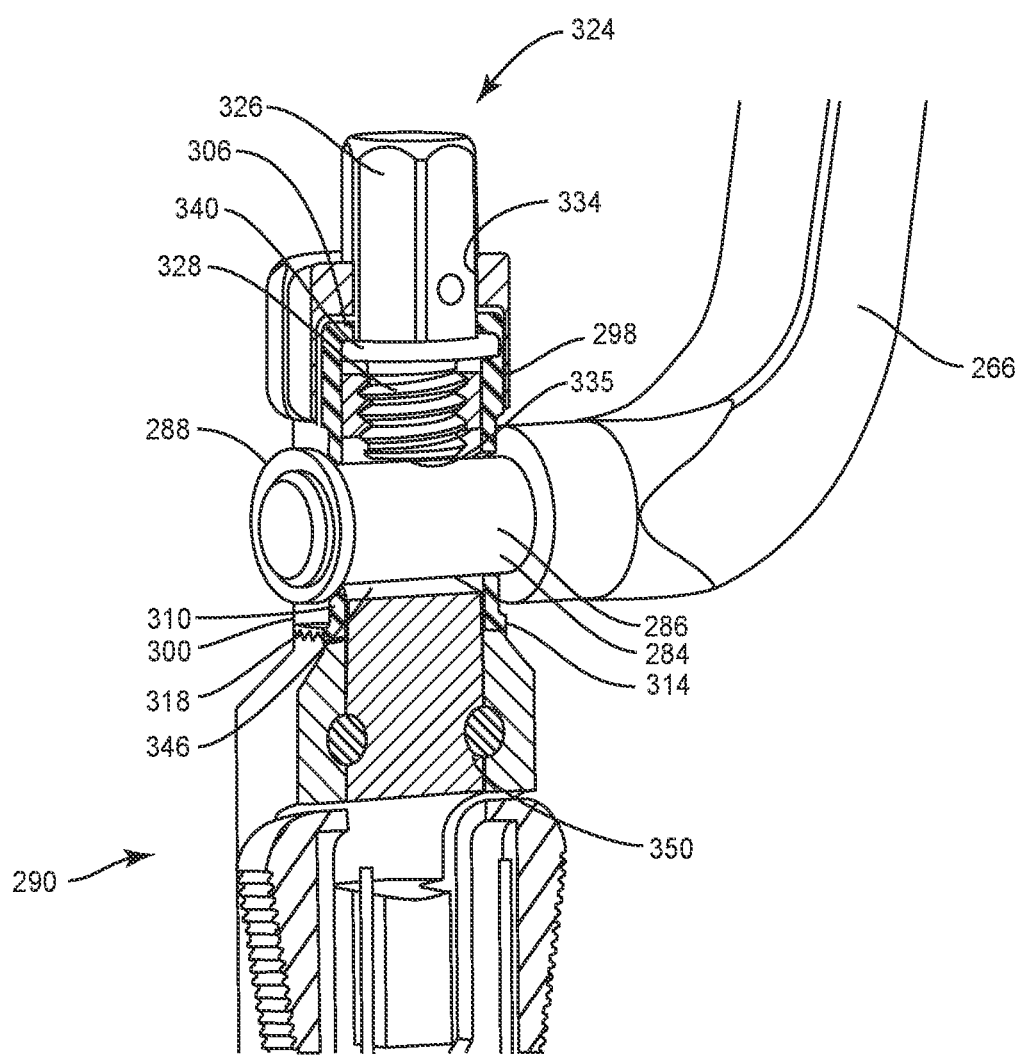
FIG. 7 is a perspective view in part cross section of the components shown in FIG. 6.
Figure 8:
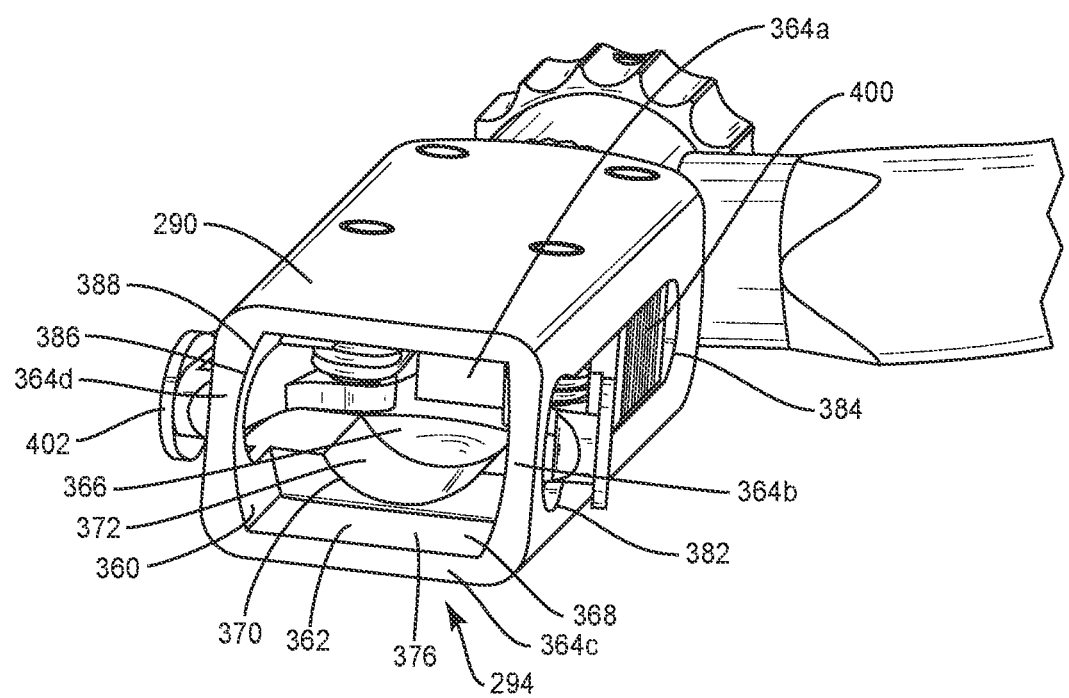
FIG. 8 is a break away perspective view of the components shown in FIG. 6.

Part 266 extends between an end 278 and an end 280 and defines an axis L2. End 278 includes a surface that defines a cavity 282. Cavity 282 is configured for disposal of pin 274 and connection with part 264, as described herein. End 280 includes an extension, such as, for example, a rod 284. In some embodiments, rod 284 extends transverse to axis L2. In some embodiments, all or only a portion of rod 284 may be disposed at alternate orientations, relative to axis L2, such as, for example, perpendicular and/or other angular orientations such as acute or obtuse, co-axial and/or may be offset or staggered. Rod 284 includes a surface 286 configured for engagement with a body, such as, for example, a sleeve 290, as shown in FIGS. 6-8. In some embodiments, surface 286 includes a circumferential lip 288 configured to resist and/or prevent disengagement of rod 284 from sleeve 290. Rod 284 is configured to facilitate rotation of sleeve 290 relative to arm 262, in the directions shown by arrows D and arrows E in FIG. 6 in a non-locking orientation, as described herein.

Sleeve 290 extends between an end 292 and an end 294 defining an axis L3. End 292 is connected with rod 284 by a lock 296. Sleeve 290 is disposable in a non-locking orientation for rotation relative to rod 284, in the direction shown by arrows D in FIG. 6. Lock 296 is configured to fix sleeve 290 relative to rod 284 in a locked orientation to resist and/or prevent rotation of sleeve 290 relative to rod 284, as described herein.

Lock 296 includes a collar 298 that extends between an end 302 and an end 304. End 302 includes a circumferential flange 306 configured for engagement with a screw 324 to facilitate translation of collar 298, as described herein. Engagement of flange 306 with screw 324 facilitates translation of collar 298 into the non-locking orientation.

Screw 324 includes a head 326 and a threaded shaft 328. In some embodiments, head 326 includes a hexagonal cross-section. In some embodiments, head 326 may have alternative cross-sections, such as, for example, rectangular, polygonal, hexalobe, oval, irregular, cruciform, phillips, square, polygonal or star cross sectional configuration.

Screw 324 includes a circumferential ring 340 configured to engage flange 306. Ring 340 is disposed between head 326 and shaft 328. Engagement of flange 306 with collar 298 facilitates translation of collar 298 into the non-locking orientation. In some embodiments, screw 324 includes a knob 330. Knob 330 includes a gripping surface 332 configured to facilitate rotation of screw 324. Knob 330 includes a surface 333 that defines a cavity 334. Cavity 334 is configured for a mating engagement with head 326. In some embodiments, cavity 334 includes a hexagonal cross-section to mate with head 326. In some embodiments, cavity 334 may have alternative cross-sections, such as, for example, rectangular, polygonal, hexalobe, oval, irregular, cruciform, phillips, square, polygonal or star cross sectional configuration.

Shaft 328 includes a surface 335 configured to engage surface 286 of rod 284. Rotation of screw 324 in a clockwise direction causes screw to translate into engagement with rod 284 to fix rod 284 with sleeve 290 in the locked orientation to resist and/or prevent rotation of sleeve 290 relative to rod 284. Surface 335 is configured to apply a force to rod 284 to fix sleeve 290 relative to rod 284. Engagement of screw 324 with rod 284 is configured to fix rod 284 between screw 324 and collar 298 preventing rotation of sleeve 290 about rod 284. Rotation of screw 324 in a counter clockwise direction causes screw to translate out of engagement with rod 284 into the non-locking orientation to allow rotation of sleeve 290 relative to rod 284.

Collar 298 includes a surface 308 that defines an opening 310. Opening 310 is configured for disposal of rod 284. In some embodiments, all or only a portion of opening 310 may include cross section configurations, such as, for example, oval, oblong, triangular, square, polygonal, irregular, uniform, non-uniform, offset, staggered, undulating, arcuate, variable and/or tapered. Collar 298 includes a surface 312 that defines a cavity 314. Cavity 314 is configured for disposal of a shaft 300, as described herein. In some embodiments, cavity 314 extends along axis L3. In some embodiments, all or only a portion of cavity 314 may be disposed at alternate orientations, relative to axis L3, such as, for example, perpendicular and/or other angular orientations such as acute or obtuse, co-axial and/or may be offset or staggered.

End 304 includes a surface 316 that defines an engagement surface, such as, for example, a splined surface 318. Sleeve 290 is disposable in a non-locking orientation for rotation relative to axis L3, in the directions shown by arrows E in FIG. 6. Splines 318 are engageable with a surface of sleeve 290 to fix sleeve 290 relative to arm 262 to resist and/or prevent rotation of sleeve 290, in the directions shown by arrows E in FIG. 6. Locking of rod 284 with sleeve 290 causes splines 318 to translate axially into engagement with sleeve 290 to fix sleeve 290 relative to arm 266 and axis L3. Splines 318 are configured for translation in a second, opposite direction out of engagement with sleeve 290 to facilitate rotation of sleeve 290 relative to arm 266 and axis L3.

Shaft 300 includes a surface 344 that defines an opening 346. Opening 346 is disposed in alignment with opening 310 to receive and support rod 284. Shaft 300 includes a surface 348 that defines a groove 350. Groove 350 is circumferentially disposed about surface 348. Groove 350 is configured for disposal of pins 352 disposed with sleeve 290. Pins 352 and groove 350 engage to prevent shaft 300 from translating while allowing shaft 300 to rotate relative to sleeve 290. In some embodiments, surface 286 and surface 344 define a joint, such as, for example a first level joint of arm 262 configured to allow sleeve 290 to pivot relative to part 266 in the directions shown by arrows A in FIG. 5. Tightening the first level joint of arm 262 causes screw 324 to translate into engagement with rod 284 to fix sleeve 290 relative to part 266, as discussed herein. Loosing the first level joint of arm 262 causes screw 324 to translate out of engagement with rod 284 to allow sleeve 290 to pivot relative to part 266, as discussed herein.

Figure 9:
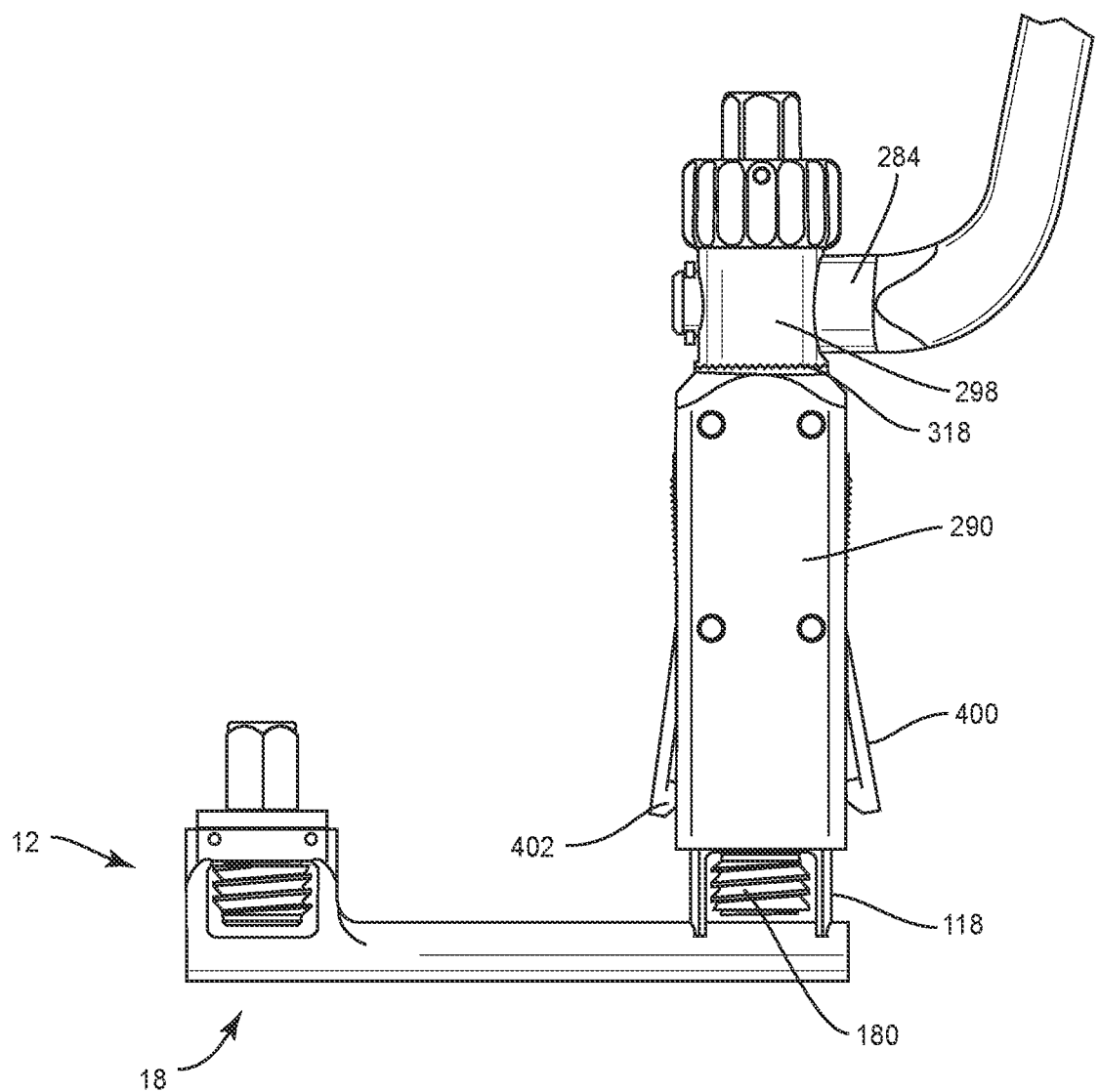
FIG. 9 is a side view of components of one embodiment of a surgical system in accordance with the principles of the present disclosure.
Figure 10:
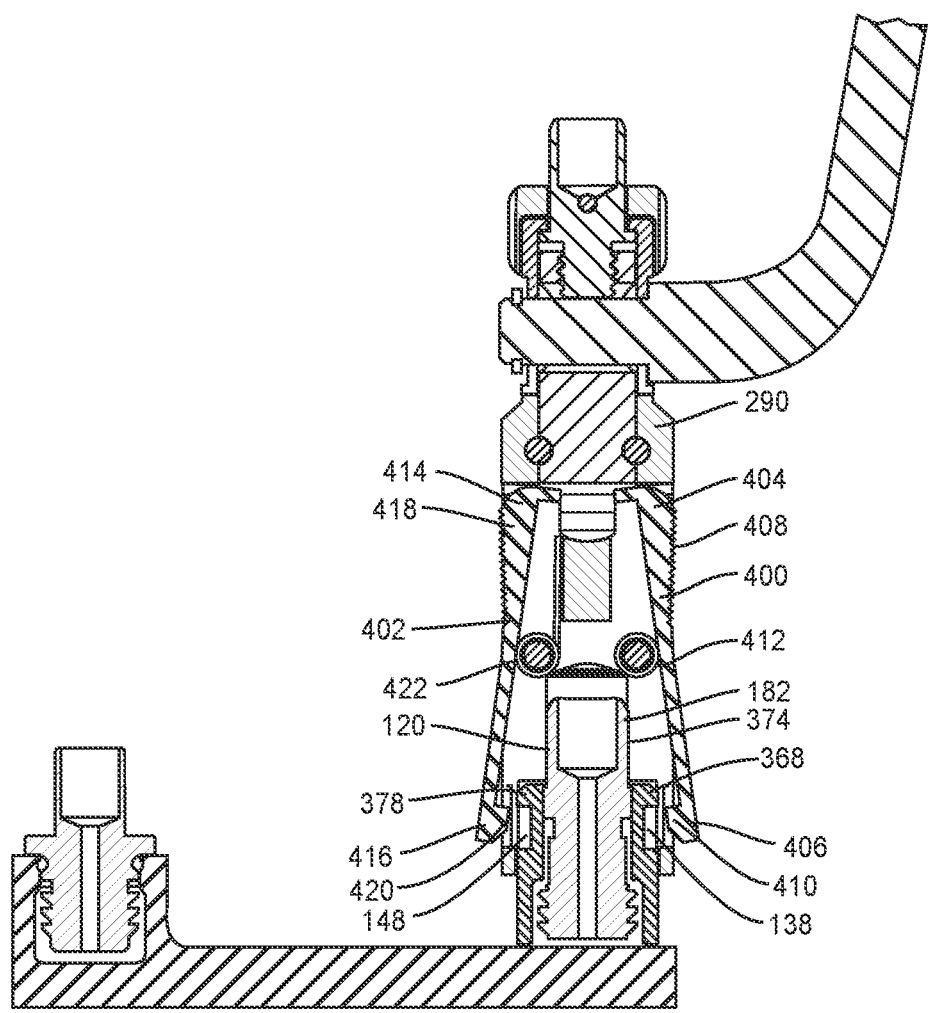
FIG. 10 is a cross section view of the components shown in FIG. 9.

End 294 of sleeve 290 includes a surface 360 that defines a cavity 362, as shown in FIGS. 8-12. Cavity 362 includes walls 364a, 364b, 364c and 364d that define a tubular configuration. In some embodiments, cavity 362 may have alternative cross-sections, such as, for example, rectangular, polygonal, oval, or irregular. Cavity 362 includes a portion 366 and a portion 368. Portion 366 includes a surface 370 that defines a recess 372. Recess 372 includes a female receptacle, such as, for example, a channel 374. Channel 374 is configured for disposal of head 182 of set screw 180, as shown in FIG. 10. Portion 368 includes a surface 376 configured for a mating engagement with support 118. Portion 366 merges with portion 368 at a surface 378 that defines a ledge 380. Ledge 380 is configured to contact wall 120. Portions 366, 368 are configured to guide support 118 into cavity 362. Cavity 362 is configured to capture and engage support 118, as described herein.

Wall 364b includes a surface 382 that defines an elongate opening 384. Opening 384 is configured for moveable disposal of an arm, such as, for example, a latch 400, as described herein. Wall 364d includes a surface 386 that defines an elongate opening 388. Opening 388 is configured for moveable disposal of an arm, such as, for example, a latch 402, as described herein. Latches 400, 402 are configured to engage detents 138, 148 to capture support 118.

Figure 11:
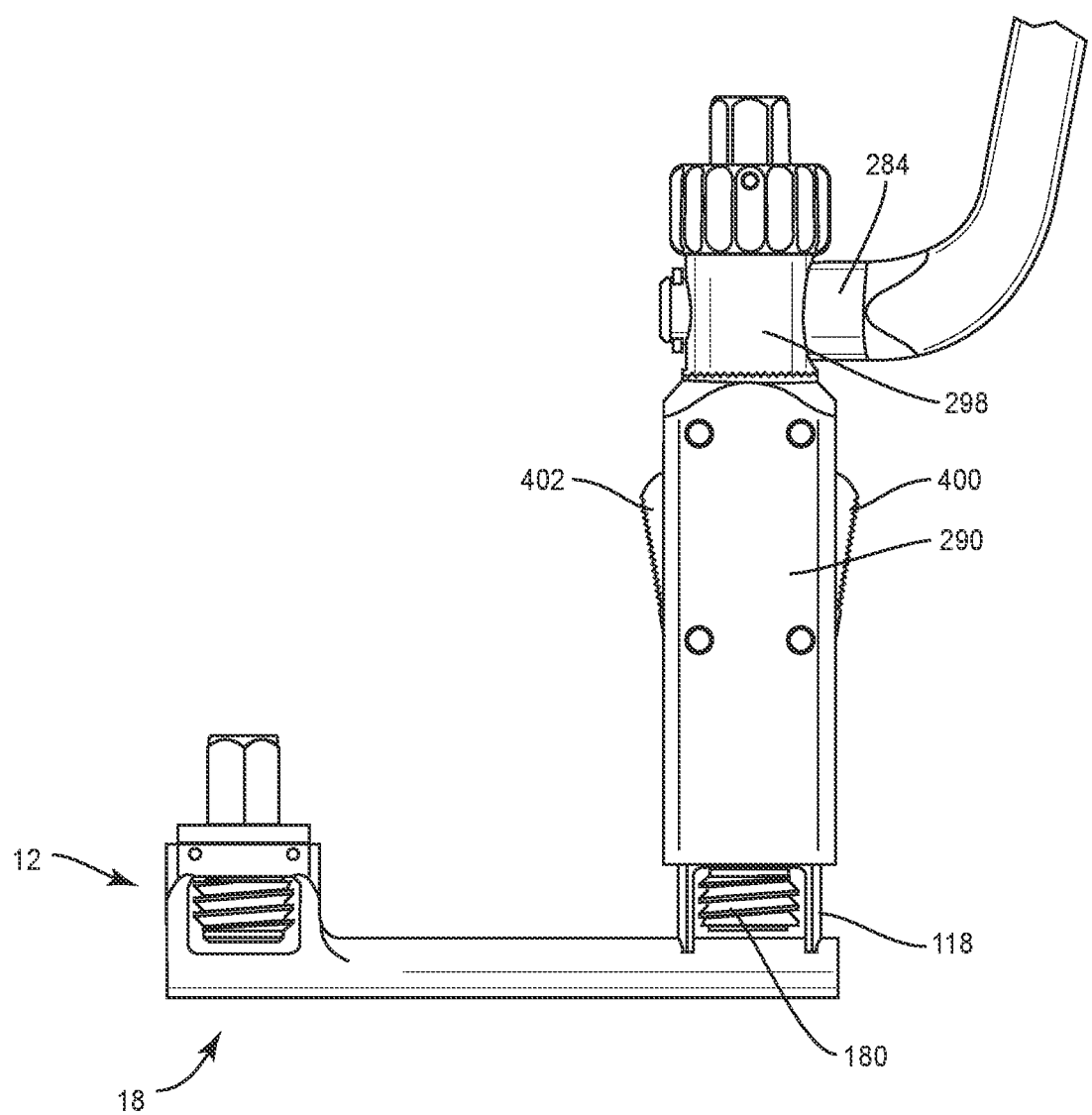
FIG. 11 is a side view of the components shown in FIG. 9.
Figure 12:
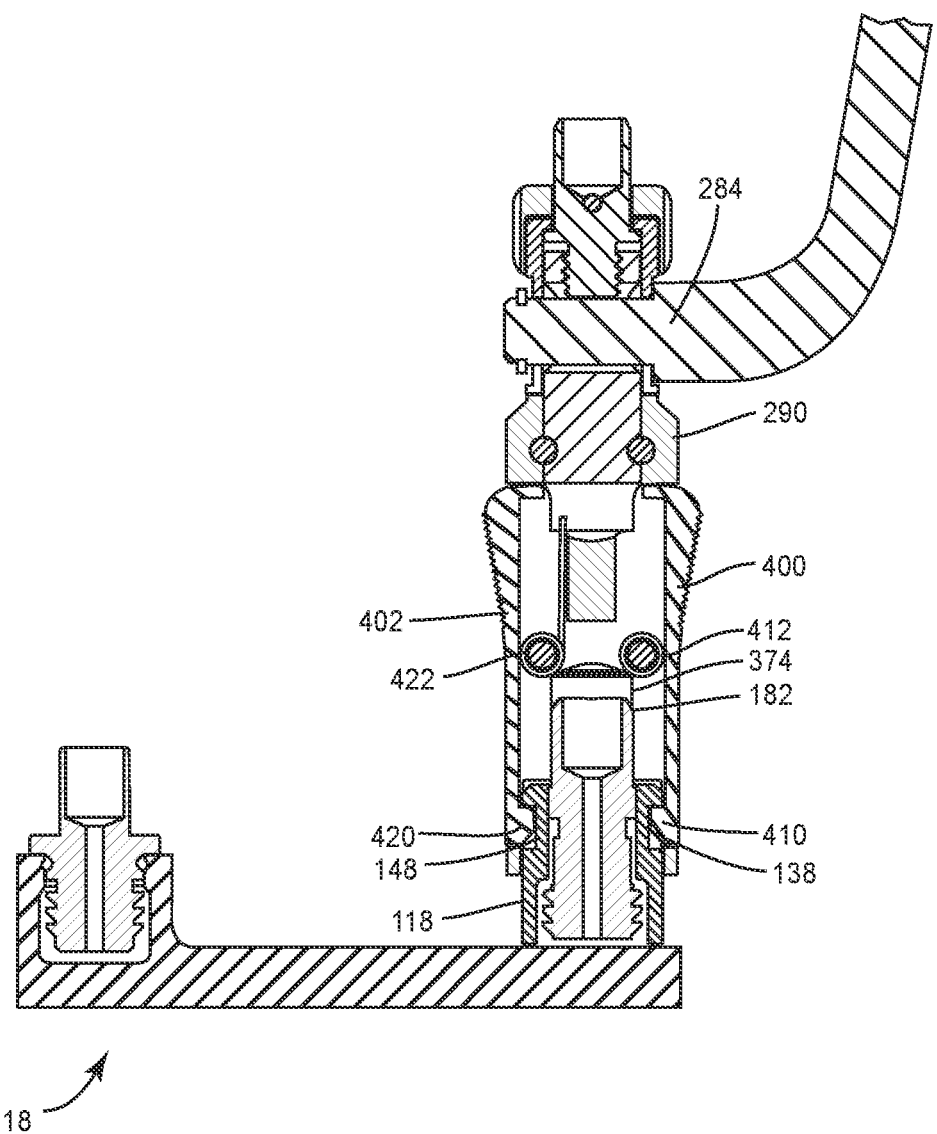
FIG. 12 is a cross section view of the components shown in FIG. 9.

Latches 400, 402 are configured for relative movement to capture support 116 in a quick release configuration, as described herein. Latch 400 extends between an end 404 and an end 406. End 404 includes a gripping surface 408 configured to facilitate manipulation of latch 400. End 406 includes a capture element 410. Capture element 410 is configured to engage detent 138. Latch 400 is connected with sleeve 290 by a spring 412. Spring 412 is configured to resiliently bias latch 400 in the closed configuration, as shown in FIG. 11.

Latch 402 extends between an end 414 and an end 416. End 414 includes a gripping surface 418 configured to facilitate manipulation of latch 402. End 416 includes a capture element 420. Capture element 420 is configured to engage detent 148. Latch 402 is connected with sleeve 290 by a spring 422. Spring 422 is configured to resiliently bias latch 402 in the closed configuration, as shown in FIG. 11. In some embodiments, latches 400, 402 are resiliently biased to a closed configuration to capture support 118, as shown in FIGS. 11, and manipulable to an open configuration, as shown in FIGS. 9 and 10. Latches 400, 402 engage support 118 in a quick release configuration such that sleeves 290, 290a and supports 118 are connectable in releasably fixed engagement via biased latches 400, 402 to facilitate intra-operative connection, as described herein. In some embodiments, the quick release configuration of spinal correction system 10 may include threaded connection, clips, dovetail connection, adhesive, key/keyslot, friction fit and/or pressure fit.

Rack 252 includes an arm 562. Arm 562 is configured for axial translation along axis A1 relative to arm 262. Arm 562 includes a part 564 and a part 566. Part 564 extends between an end 568 and an end 570. End 568 is configured for connection with rack 252. In some embodiments, end 588 includes a lock 600. Lock 600 is configured for manipulation in various orientations to fix arm 562 in various configurations relative to arm 262 along rack 252. In some embodiments, lock 600 is oriented to allow translation of arm 562 towards arm 262. In some embodiments, lock 600 is oriented to allow translation of arm 462 away from arm 262. In some embodiments, lock 600 is oriented to allow translation of arm 462 towards and away from arm 262. In some embodiments, lock 600 is oriented to resist and/or prevent translation of arm 562 to fix arm 562 with rack 252. In some embodiments, end 668 is attached with rack 252 via, for example, clips, hooks, adhesives and/or flanges. In some embodiments, rack 252 and part 564 define a joint, such as, for example a third level joint of arm 562 configured to allow part 564 to pivot relative to rack 252 in the directions shown by arrows B in FIG. 5. Locking mechanism 576 may be manipulated to tighten the third level joint of arm 562 to fix part 264 relative to rack 252. Locking mechanism 576 may be manipulated to loosen the third level joint of arm 562 to allow part 564 to pivot relative to rack 252.

End 570 includes a surface that defines a cavity 572. Cavity 572 is configured for disposal of part 566, similar to part 266 described herein. Cavity 572 includes a pin hinge 574 configured to facilitate a pivotable connection with part 566. Pin hinge 574 facilitates rotation of part 566 relative to part 564. Part 566 is configured to rotate relative to part 564, in the directions shown by arrows B in FIG. 5. Part 564 includes a locking mechanism 576 configured to fix part 566 relative to part 564. In some embodiments, hinge 574 defines a joint, such as, for example a second level joint of arm 562 configured to allow part 566 to pivot relative to part 564 in the directions shown by arrows B in FIG. 5. Locking mechanism 576 may be manipulated to tighten the second level joint of arm 562 to fix part 566 relative to part 564, as discussed herein. Locking mechanism 576 may be manipulated to loosen the second level joint of arm 562 to allow part 566 to pivot relative to part 564, as discussed herein.

Part 566 extends between an end 578 and an end 580 and defines an axis L4. End 578 includes a surface that defines a cavity 582. Cavity 582 is configured for disposal of pin hinge 574 and connection with part 564, as described herein. End 580 includes a rod 584, similar to rod 284 described herein. Rod 584 includes a surface 586 configured for engagement with a sleeve 290a, similar to sleeve 290 described herein. Surface 586 includes a circumferential lip 588 configured to resist and/or prevent disengagement of rod 584 from sleeve 290a, similar to that described herein. Rod 584 is configured to facilitate rotation of sleeve 290a relative to arm 562 between a non-locking orientation and a locked orientation, similar to sleeve 290 described herein. In some embodiments, surface 586 and an inner surface of sleeve 290a define a joint, such as, for example a first level joint of arm 562 configured to allow sleeve 290a to pivot relative to part 566 in the directions shown by arrows B in FIG. 5. Tightening the first level joint of arm 562 causes a screw similar to screw 324 to translate into engagement with rod similar to rod 284 to fix sleeve 290a relative to part 566, as discussed herein. Loosening the first level joint of arm 562 causes the screw to translate out of engagement with the rod to allow sleeve 290a to pivot relative to part 566, as discussed herein.

Figure 13:
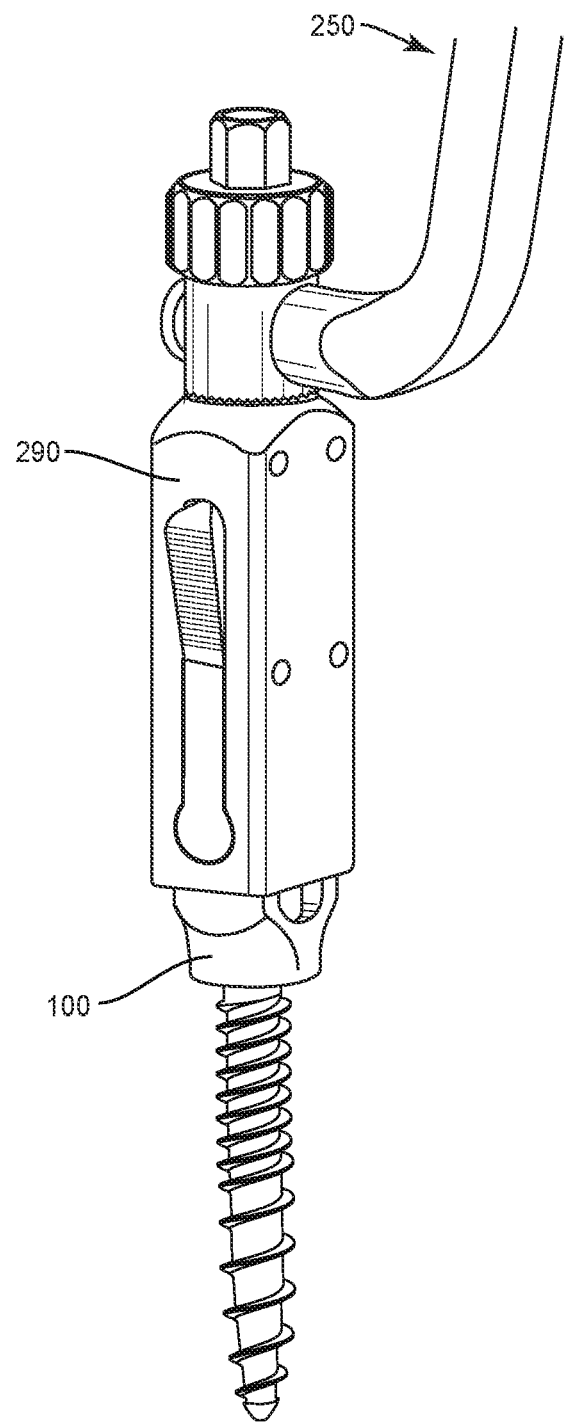
FIG. 13 is a perspective view of components of one embodiment of a surgical system in accordance with the principles of the present disclosure.

In some embodiments, surgical instrument 250 is configured for a direct connection with the receiver of a fixed angle bone fastener 100, as shown in FIG. 13. In some embodiments, sleeve 290 and/or sleeve 290a are configured for engagement with the receiver of bone fastener 100 to direct a compression and/or distraction load along a single bone fastener.

In assembly, operation and use, spinal correction system 10 including spinal construct 12 and surgical instrument 250, similar to the systems and methods described with regard to FIGS. 1-13, is employed with a surgical procedure, such as, for example, a PSO for treatment of a spine of a patient including vertebrae V, as shown in FIGS. 14-21. Spinal correction system 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of spinal construct 12.

Spinal correction system 10 is employed with a PSO procedure for treatment of an applicable condition or injury of an affected section of a spinal column and adjacent areas within a body. For example, vertebrae V includes a vertebral level V1, a vertebral level V2 and a vertebral level V3. Diseased and/or damaged vertebrae and intervertebral discs are disposed at vertebrae V2 between vertebrae V1 and V3. In some embodiments, components of spinal correction system 10 are configured for insertion with a vertebral space to space apart articular joint surfaces, provide support and maximize stabilization of vertebrae V.

Figure 14:
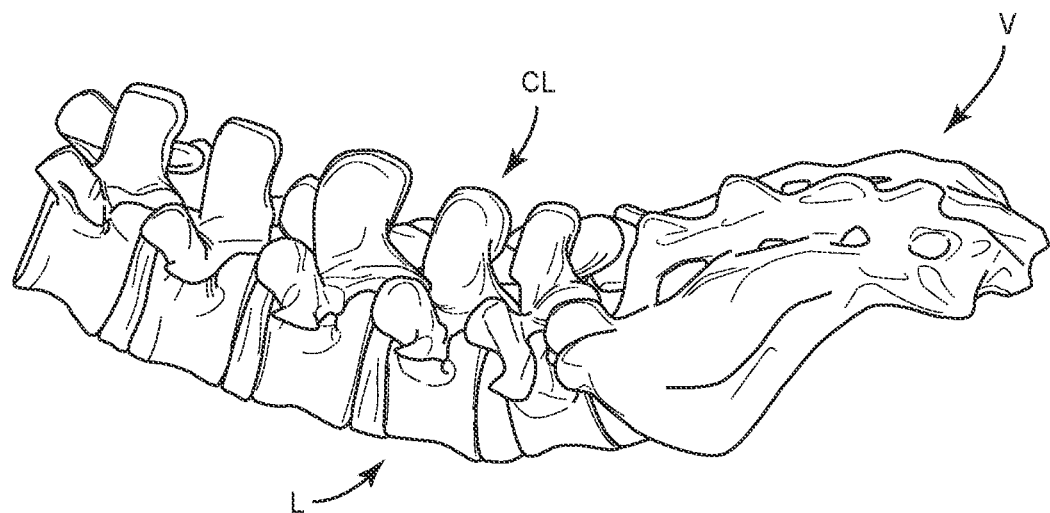
FIG. 14 is a lateral view of vertebrae.

In use, to treat the affected section of vertebrae V, a medical practitioner obtains access to a surgical site including vertebrae V, as shown in FIG. 14, in any appropriate manner, such as through incision and retraction of tissues. In some embodiments, spinal correction system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

Figure 15:
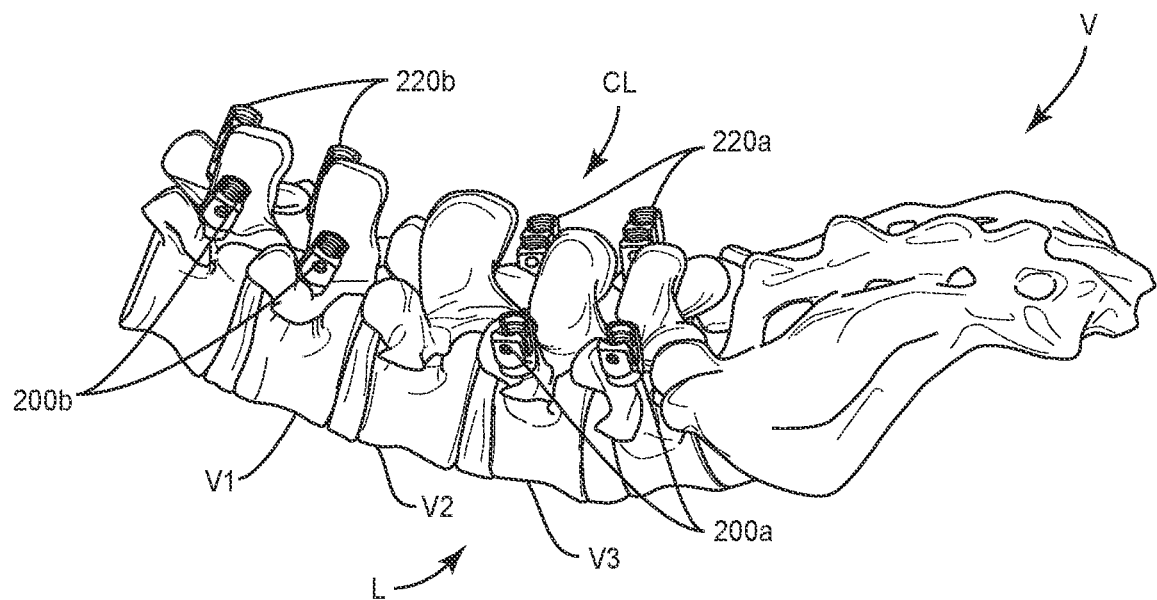
FIG. 15 is a perspective view of components of one embodiment of a surgical system in accordance with the principles of the present disclosure disposed with vertebrae.

MAS screws 200 are engaged with vertebrae V along a lateral side L of vertebrae V, as shown in FIG. 15. In some embodiments, MAS screws 200 are disposed in pairs 200*a*, 200*b* alongside L. In some embodiments, pair 200*a* is disposed inferior to vertebra V2 and pair 200*b* is disposed superior to vertebra V2. DRMAS 220 are engaged along a contralateral side CL of vertebrae V, as shown in FIG. 15. In some embodiments, DRMAS screws 220 are disposed in pairs 220*a*, 220*b* alongside CL. In some embodiments, pair 220*a* is disposed inferior to vertebra V2 and pair 220*b* is disposed superior to vertebra V2. The receivers of MAS 200 and DRMAS 220 are configured to rotate within six degrees relative to the shafts.

Figure 16:
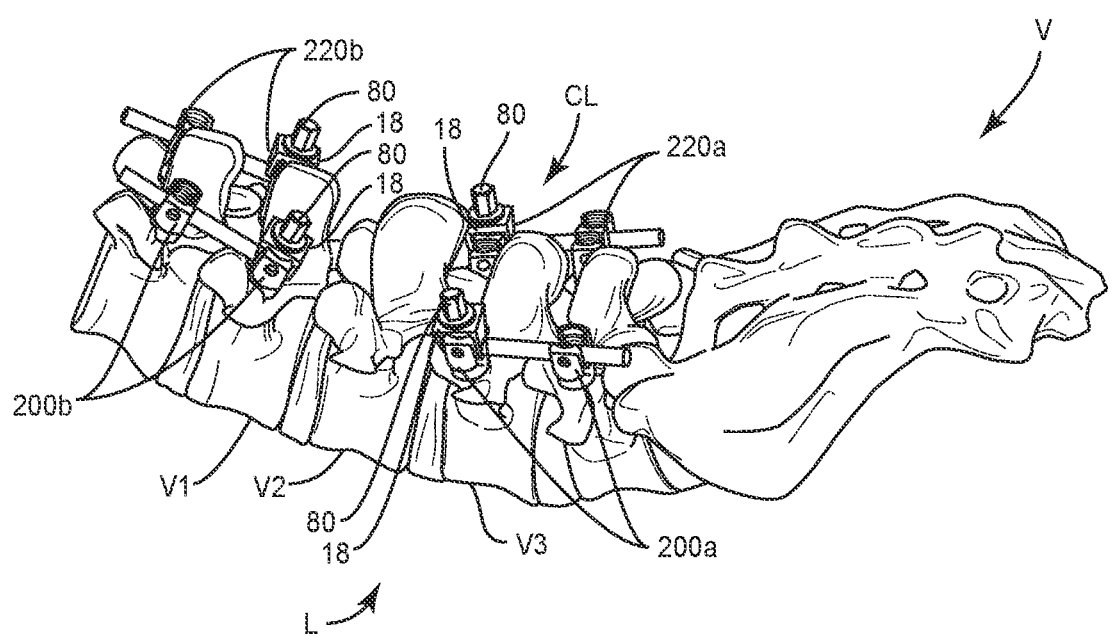
FIG. 16 is a perspective view of components of one embodiment of a surgical system in accordance with the principles of the present disclosure disposed with vertebrae.

Support 18 is engaged with pair 200*a* such that support 18 is disposed adjacent vertebra V2 and rod 36 extends in an inferior orientation to an adjacent MAS 200, as shown in FIG. 16. Set screw 80 is engaged with receiver 202 disposed adjacent vertebrae V2. Support 18 is engaged with pair 200*b* such that support 18 is disposed adjacent vertebra V2 and rod 36 extends in a superior orientation to an adjacent MAS 200. Set screw 80 is engaged with receiver 202 disposed adjacent vertebrae V2.

Support 18 is engaged with pair 220*a* such that support 18 is disposed adjacent vertebra V2 and rod 36 extends in an inferior orientation to an adjacent MAS screw 200. Set screw 80 is engaged with receiver 222 disposed adjacent vertebrae V2. Support 18 is engaged with pair 220*b* such that support 18 is disposed adjacent vertebra V2 and rod 36 extends in a superior orientation to an adjacent MAS 200. Set screw 80 is engaged with receiver 222 disposed adjacent vertebrae V2.

Figure 17:
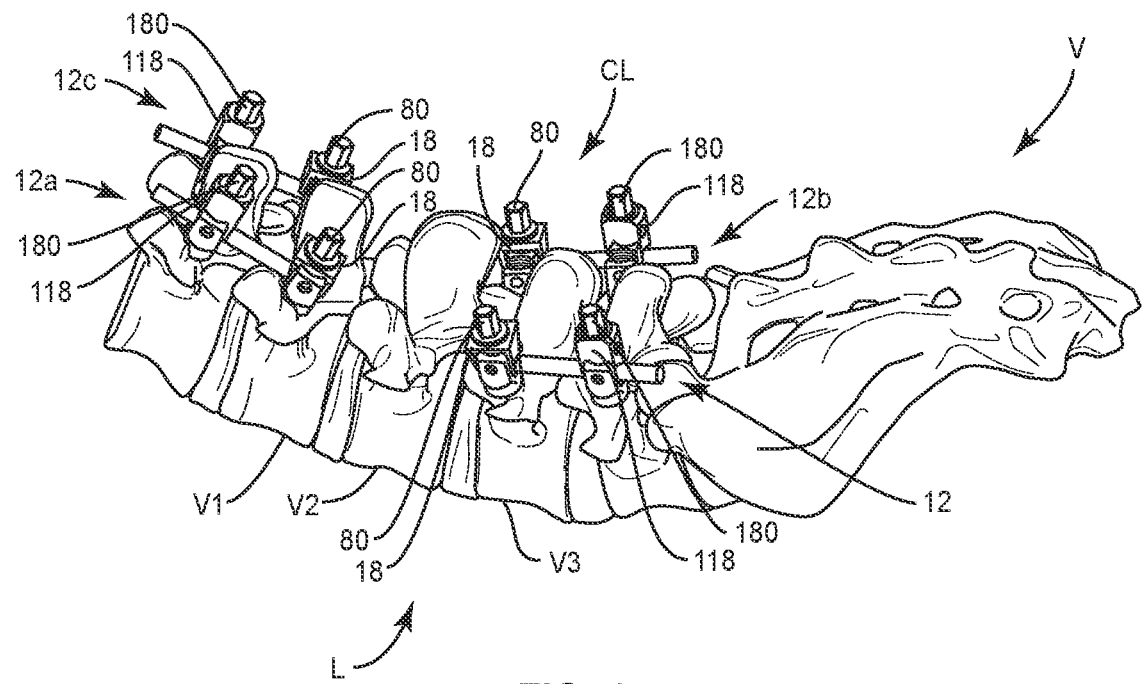
FIG. 17 is a perspective view of components of one embodiment of a surgical system in accordance with the principles of the present disclosure disposed with vertebrae.

A surgical instrument, such as, for example, a driver is connected with set screw 80 and/or set screw 180 to facilitate engagement of supports 18, 118. Support 118 is engaged with pair 200*a* such that set screw 180 is engaged with the adjacent MAS screw 200 receiver 202 and rod 36, as shown in FIG. 17. Support 118 is engaged with pair 200*b* such that set screw 180 is engaged with the adjacent receiver 202 and rod 36. Support 118 is engaged with pair 220*a* such that set screw 180 is engaged with the adjacent DRMAS 220 receiver 222 and rod 36. Support 118 is engaged with pair 220*b* such that set screw 180 is engaged with the adjacent DRMAS 220 receiver 222 and rod 36.

Engagement of supports 18, 118 with rod 36 and the adjacent bone fasteners construct connector 12. Attachment of connectors 12 with pairs 200*a*, 200*b*, 200*a*, 200*b* resists and/or prevents movement of the receivers relative to the shafts and/or vertebrae attached therewith. In some embodiments, movement of the receivers relative to the shafts and/or vertebrae can be prevented in one or a plurality of degrees of freedom of the fasteners, as described herein.

Figure 18:
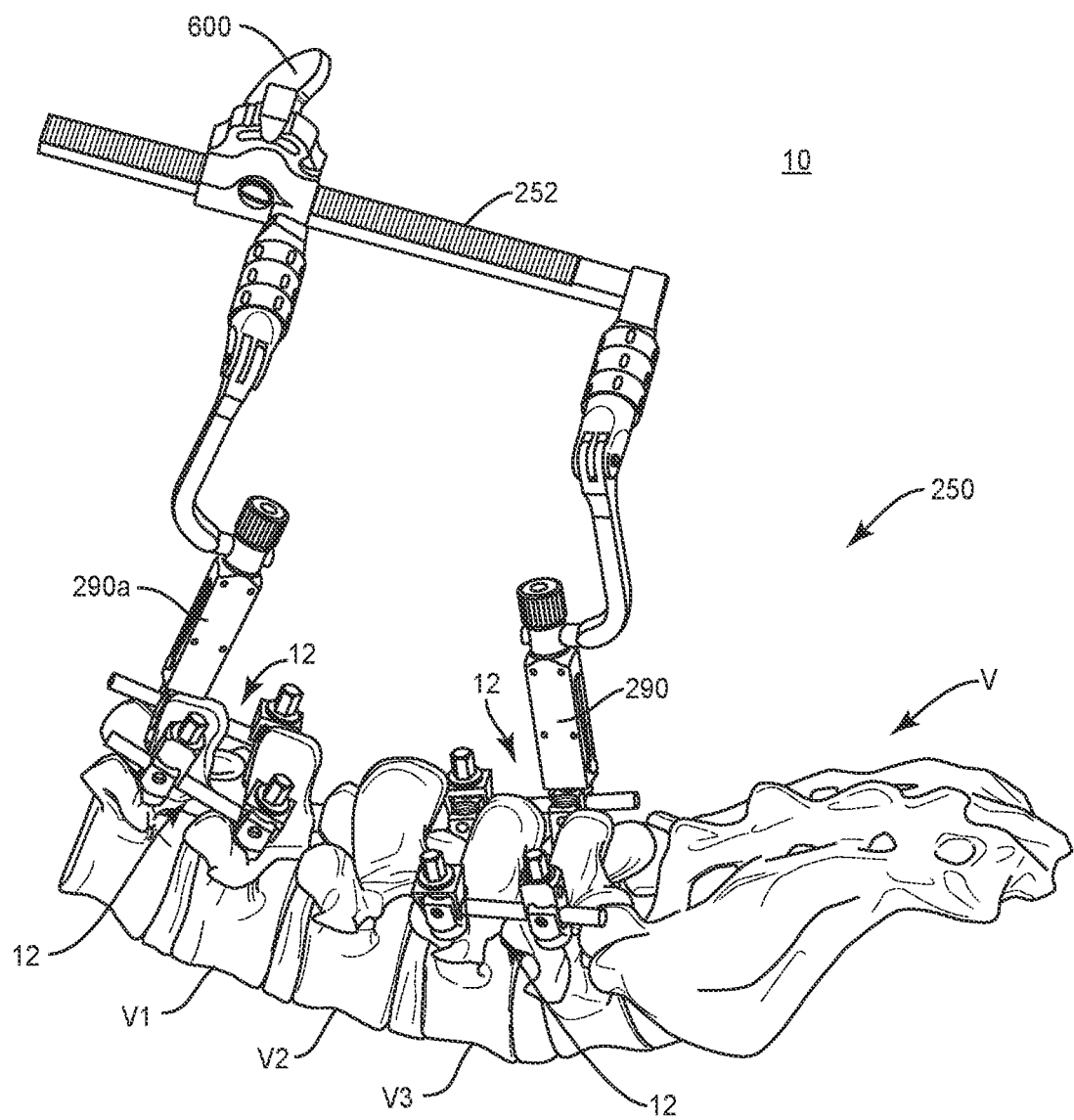
FIG. 18 is a perspective view of components of one embodiment of a surgical system in accordance with the principles of the present disclosure disposed with vertebrae.

Surgical instrument 250 is connected with supports 118 disposed alongside CL of vertebrae V, as shown in FIG. 18. In some embodiments, part 266 and/or part 566 are rotatable relative to arm 262, arm 562, rack 252, the spinal constructs and/or vertebrae V to orient sleeve 290 and/or sleeve 290*a* in a selected orientation to capture one or more connector 12. In some embodiments, part 266 is fixed in a selected orientation with locking mechanism 276 and part 566 is fixed in a selected orientation with locking mechanism 576, as described herein. Sleeves 290, 290*a* are translated over supports 118 such that capture elements 406, 416 are engaged with detents 138, 148 in a quick release configuration, as described herein.

Figure 19:
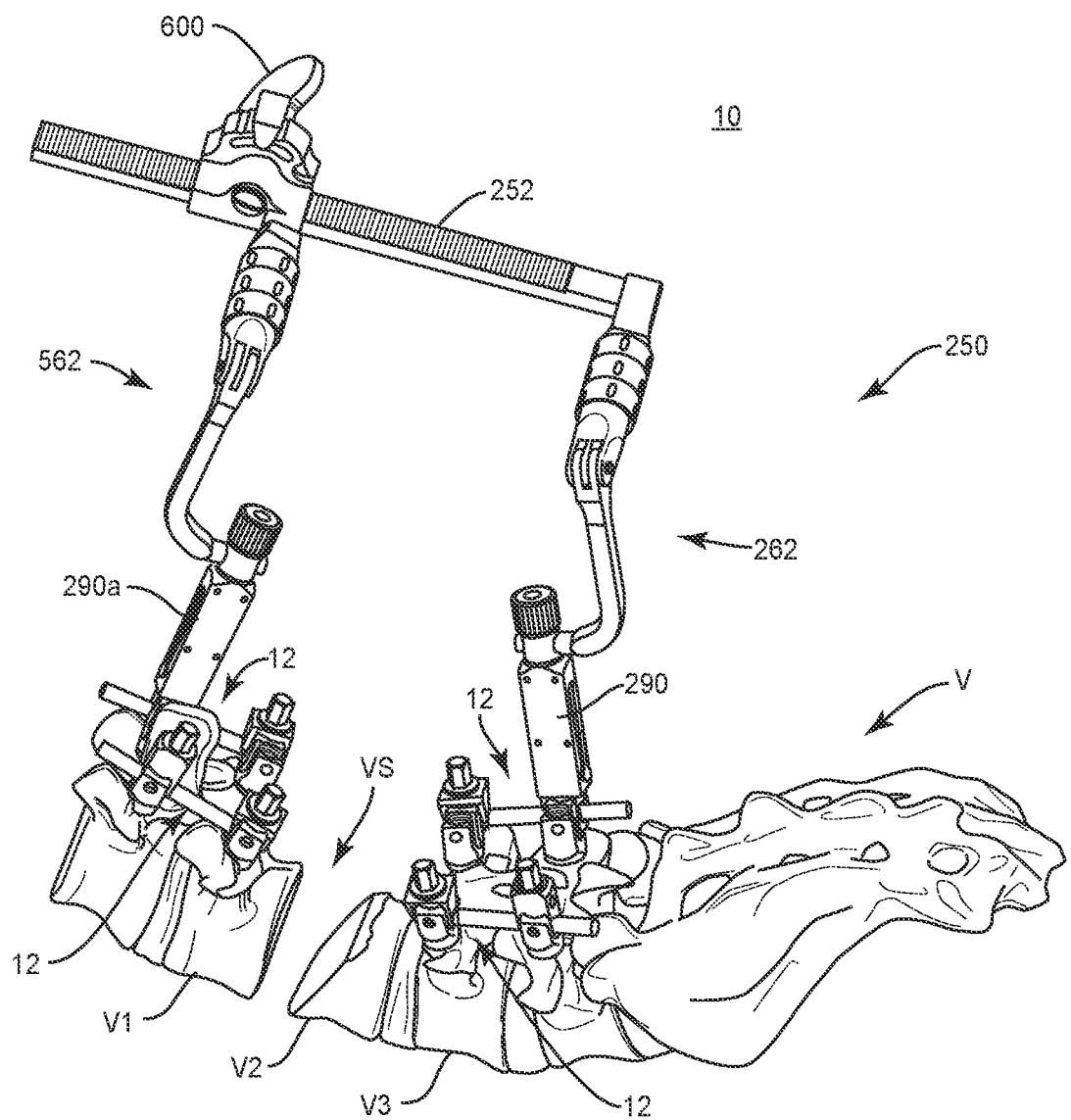
FIG. 19 is a perspective view of components of one embodiment of a surgical system in accordance with the principles of the present disclosure disposed with vertebrae.

In some embodiments, a surgical instrument, such as, for example, an osteotome is utilized to facilitate removing all or a portion of vertebra V2 and adjacent intervertebral disc tissue to define a vertebral space VS, as shown in FIG. 19. In some embodiments, vertebral space VS can include posterior portions of the spine, such as, for example, pedicles, laminae and/or spinous process. In some embodiments, a wedge portion of bone and/or other tissue is removed from a selected vertebra and adjacent intervertebral disc tissue remains intact.

Figure 20:
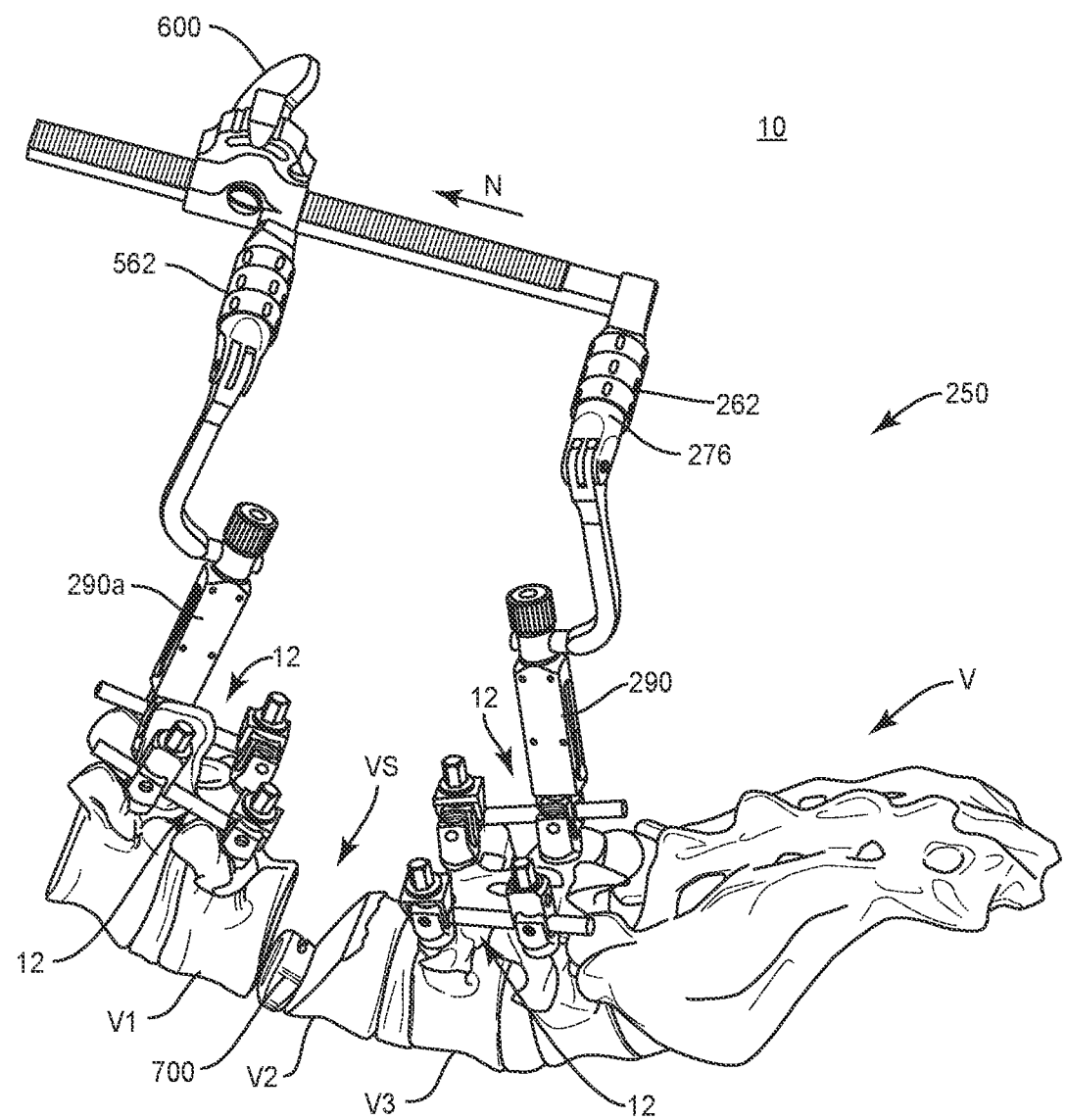
FIG. 20 is a perspective view of components of one embodiment of a surgical system in accordance with the principles of the present disclosure disposed with vertebrae.

Lock 600 is manipulated to axially translate arm 562 along rack 252 relative to arm 262 to facilitate compression and/or distraction of vertebrae V. Translation of arm 562 relative to arm 262 along rack 252, in a direction shown by arrow N in FIG. 20, distracts vertebrae V to open vertebral space VS. In some embodiments, a spinal implant, such as, for example, an intrabody implant 700 is disposed within vertebral space VS, as shown in FIG. 20. In some embodiments, intrabody implant 700 is configured to preserve anterior height and maintain alignment of vertebrae V. Intrabody implant 700 provides a fulcrum about which vertebrae V1, V2 are pivoted by surgical instrument 250.

Figure 21:
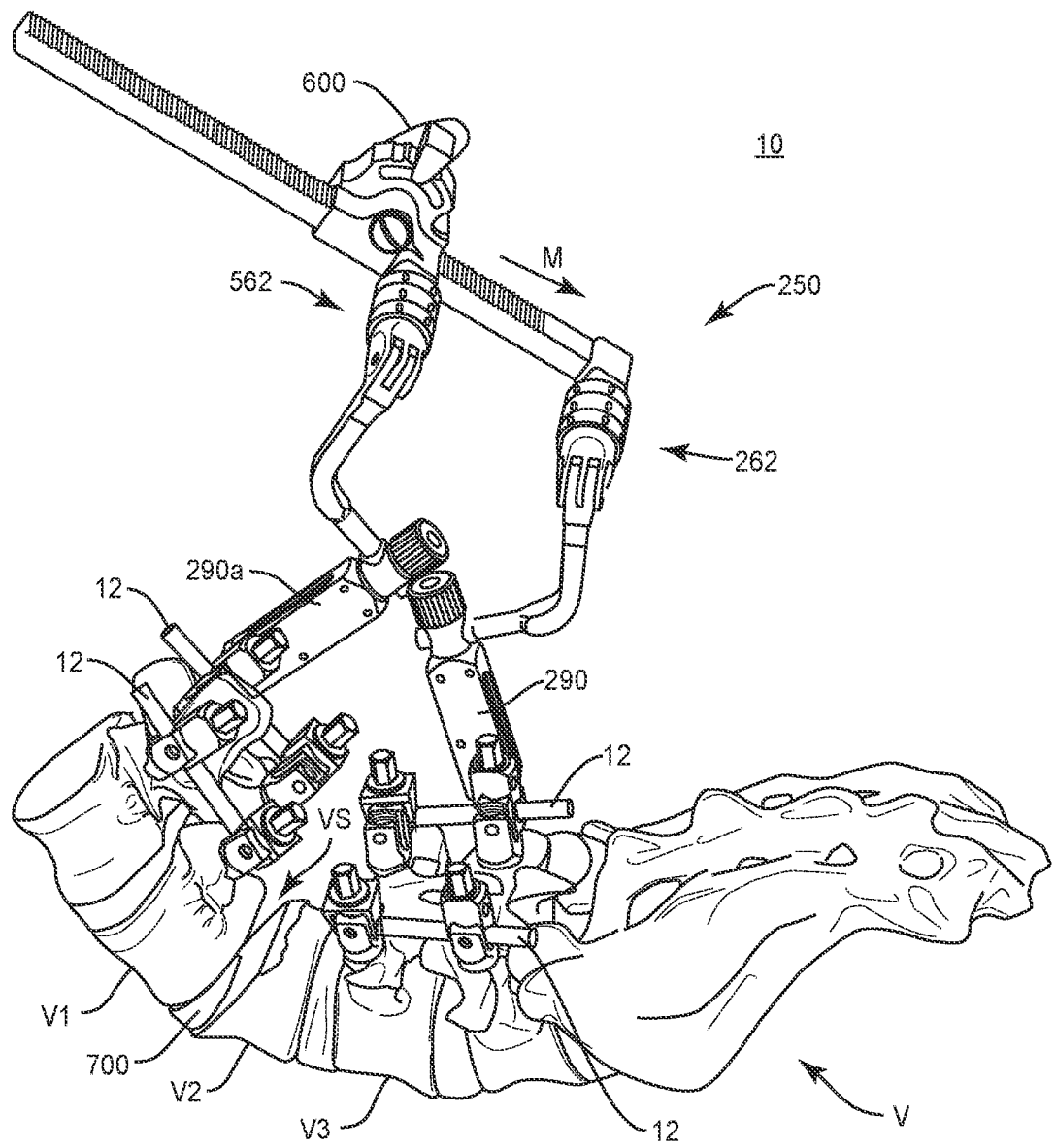
FIG. 21 is a perspective view of components of one embodiment of a surgical system in accordance with the principles of the present disclosure disposed with vertebrae.

Surgical instrument 250 is manipulated to pivot vertebrae V1, V2 about intrabody implant 700. Translation of arm 562, in a direction shown by arrow M in FIG. 21, is configured to compress vertebrae V to achieve correction, for example, a selected lordosis. In some embodiments, surgical instrument 250 manipulates vertebrae V during a surgical correction treatment to rotate, displace, pull, twist or align vertebrae V to a selected orientation for sagittal, coronal and/or axial correction. In some embodiments, surgical instrument 250 applies derotation forces to vertebrae V for correction of vertebrae V.

Upon completion of a procedure, as described herein, the surgical instruments, assemblies and non-implanted components of spinal correction system 10 are removed and the incision(s) are closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of plates, connectors and/or bone fasteners for use with a single vertebral level or a plurality of vertebral levels.

In some embodiments, spinal correction system 10 includes one or a plurality of alternate surgical instruments, each configured for mating engagement in a quick release configuration with spinal constructs, as described herein. This configuration facilitates the interchangeability of the spinal constructs with the alternate surgical instruments. In some embodiments, spinal correction system 10 includes one or a plurality of alternate surgical instruments, such as, for example, inserters, extenders, reducers, spreaders, distractors, blades, retractors, clamps, forceps, elevators and drills, which may be alternately sized and dimensioned, and arranged as a kit.

In some embodiments, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration.

In one embodiment, as shown in FIGS. 22-31, spinal correction system 10, similar to the systems and methods described with regard to FIGS. 1-21, includes a spinal construct, such as, for example, a connector 1412, similar to the connectors described herein.

Connector 1412 is engageable with fasteners and a surgical instrument to manipulate tissue, similar to that described herein. Connector 1412 includes a member 1416. Member 1416 includes a body, such as, for example, a support 1418. Support 1418 includes a wall 1420 that extends between an end 1422 and an end 1424. Wall 1420 extends parallel to a longitudinal axis X2 defined by a rod 1442, as described herein. Wall 1420 includes a surface 1426 that defines a channel 1428. Channel 1428 is configured for disposal of an actuator, as described herein.

Wall 1420 includes an extension, such as, for example, a leg 1430. Leg 1430 extends from end 1422. Leg 1430 is pivotally connected with end 1422 with a pin to facilitate rotation of leg 1430 relative to support 1420, as described herein. Leg 1430 includes a surface 1432 that defines a portion of a support cavity 1434. Cavity 1434 is configured to capture at least a portion of a bone fastener 1650, as described herein. Surface 1432 is configured to surround and/or engage a portion of a receiver of bone fastener 1650. Surface 1432 defines a tab 1436 projecting into cavity 1434 and configured for releasably capturing bone fastener 1650.

Leg 1430 includes a surface 1438 that defines an opening 1440. Surface 1438 is configured for engagement with a rod 1442, as described herein. Leg 1430 is configured for relative movement to capture MAS 1650, as described herein. In some embodiments, leg 1430 is resiliently biased in an open configuration and is movable to a closed configuration to capture bone fastener 1650, as described herein.

Wall 1420 includes an extension, such as, for example, a leg 1450. Leg 1450 extends from end 1424. Leg 1450 is pivotally connected with end 1424 with a pin to facilitate rotation of leg 1450 relative to support 1420, as described herein. Leg 1450 includes a surface 1452 that defines a portion of support cavity 1434, as described herein. Surface 1452 is configured to surround and/or engage a portion of a receiver of bone fastener 1650. Surface 1452 defines a tab 1456 projecting into cavity 1434 and configured for releasably capturing bone fastener 1650. Leg 1450 includes a surface 1458 that defines an opening 1460. Surface 1458 is configured for engagement with rod 1442, as described herein.

Leg 1450 is configured for relative movement to capture bone fastener 1650, as described herein. In some embodiments, leg 1450 is resiliently biased in an open configuration and is movable to a closed configuration to capture bone fastener 1650, as described herein.

Rod 1442 extends between an end 1470 and an end 1472. Rod 1442 is configured for engagement with a rod contact member, as described herein. In some embodiments, rod 1442 includes an outer threaded surface engageable with leg 1430 and/or leg 1450. In some embodiments, rod 1442 is configured to connect a receiver of one bone fastener with a receiver of an adjacent bone fastener, as described herein.

Member 1416 includes a part, such as, for example, a collar 1480. Collar 1480 includes a surface 1482 that defines an opening 1484. Opening 1484 is configured for slidable disposal of leg 1430. Collar 1480 includes a surface 1486 that defines an opening 1488. Opening 1488 is configured for slidable disposal of leg 1450. Collar 1480 includes an extension, such as, for example, a rod contact member 1490. Rod contact member 1490 includes a surface 1492 configured to engage rod 1442. Collar 1480 is configured for axial translation relative to legs 1430, 1450 to move legs 1430, 1450 into a capture configuration to capture bone fastener 1650. Translation of collar 1480 causes surface 1492 to translate into engagement with rod 1442.

Collar 1480 includes a surface 1494 that defines a channel 1496. Channel 1496 is in communication with channel 1428. Channel 1496 is configured for disposal of actuator 1500. Actuator 1500 extends between an end 1502 and an end 1504. End 1502 includes a surface 1506 configured for connection with a surgical instrument, such as, for example, a driver. In some embodiments, surface 1506 includes a hexagonal cross-section to facilitate engagement with a surgical tool or instrument. In some embodiments, surface 1506 may have alternative cross-sections, such as, for example, rectangular, polygonal, hexalobe, oval, or irregular.

End 1504 is fixedly connected with collar 1480 to axially translate collar 1480 to move legs 1430, 1450 into engagement with bone fastener 1650 and engage surface 1492 with rod 1442. In some embodiments, actuator 1500 includes a spring 1507 configured to bias legs 1430, 1450 in an open configuration. Translation of actuator 1500 into support 1420 causes a surface of support 1420 to compress spring 1507 to overcome the bias of spring 1507. Compression of spring 1507 facilitates translation of collar 1480 along legs 1430, 1450 into a capture configuration.

Support 1418 includes a surface 1508 that defines a mating element, such as, for example, a slot 1510. Support 1418 includes a surface 1512 that defines a mating element, such as, for example, a slot 1514. Slots 1510, 1514 are configured for mating engagement with a surgical instrument, as described herein. In some embodiments, slots 1510, 1514 include a circular configuration. Slots 1510, 1514 are configured for releasable engagement with a surgical instrument to facilitate manipulation of tissue such that movement of a receiver relative to a shaft of bone fastener 1650 is resisted and/or prevented.

Figure 22:
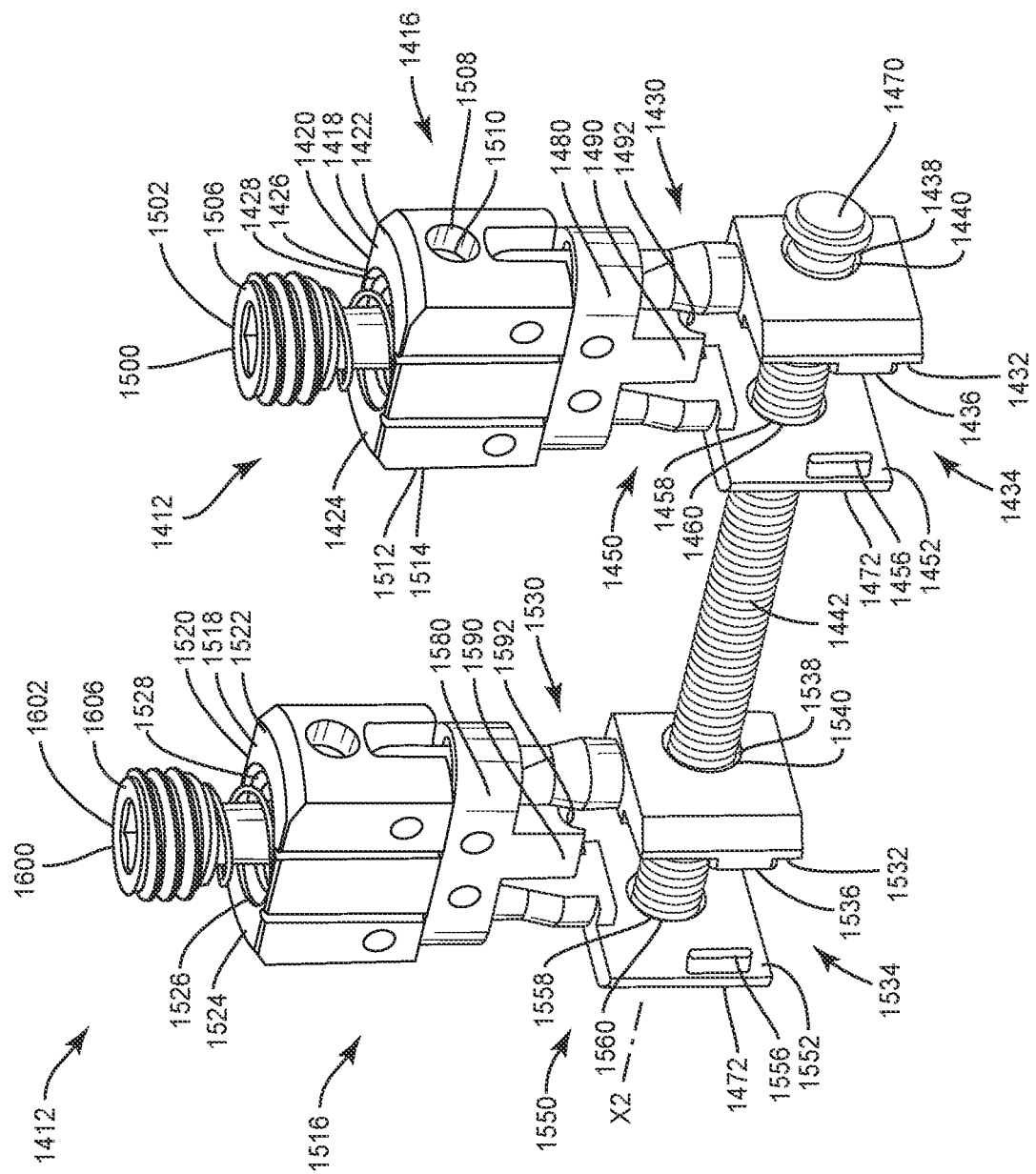
FIG. 22 is a perspective view of components of one embodiment of a surgical system in accordance with the principles of the present disclosure.

Connector 1412 includes a member 1516. Member 1516 includes a body, such as, for example, a support 1518. Support 1518 includes a wall 1520 that extends between an end 1522 and an end 1524. Wall 1520 extends parallel to axis X2, as shown in FIG. 22. Wall 1520 includes a surface 1526 that defines a channel 1528. Channel 1528 is configured for disposal of an actuator, as described herein.

Wall 1520 includes an extension, such as, for example, a leg 1530. Leg 1530 extends from end 1522. Leg 1530 is pivotally connected with end 1522 with a pin to facilitate rotation of leg 1530 relative to support 1520, as described herein. Leg 1530 includes a surface 1532 that defines a portion of a support cavity 1534. Cavity 1534 is configured to capture at least a portion of bone fastener 1650, as described herein. Surface 1532 is configured to surround and/or engage a portion of a receiver of bone fastener 1650.

Surface 1532 defines a tab 1536 projecting into cavity 1534 and configured for releasably capturing bone fastener 1650.

Leg 1530 includes a surface 1538 that defines an opening 1540. Surface 1538 is configured for engagement with a rod 1442, as described herein. Leg 1530 is configured for relative movement to capture bone fastener 1650, as described herein. In some embodiments, leg 1530 is resiliently biased in an open configuration and is movable to a closed configuration to capture bone fastener 1650, as described herein.

Wall 1520 includes an extension, such as, for example, a leg 1550. Leg 1550 extends from end 1524. Leg 1550 is pivotally connected with end 1524 with a pin to facilitate rotation of leg 1550 relative to support 1520, as described herein. Leg 1550 includes a surface 1552 that defines a portion of support cavity 1534, as described herein. Surface 1552 is configured to surround and/or engage a portion of a receiver of bone fastener 1650. Surface 1552 defines a tab 1556 projecting into cavity 1534 and configured for releasably capturing bone fastener 1650.

Leg 1550 includes a surface 1558 that defines an opening 1560. Surface 1558 is configured for engagement with rod 1442, as described herein. Leg 1550 is configured for relative movement to capture bone fastener 1650, as described herein. In some embodiments, leg 1550 is resiliently biased in an open position and is movable to capture bone fastener 1650, as described herein. In some embodiments, rod 1442 includes an outer threaded surface engageable with leg 1530 and/or leg 1550.

Member 1516 includes a part, such as, for example, a collar 1580. Collar 1580 includes a surface 1582 that defines an opening 1584. Opening 1584 is configured for slidable disposal of leg 1530. Collar 1580 includes a surface 1586 that defines an opening 1588. Opening 1588 is configured for slidable disposal of leg 1550. Rod contact member 1590 includes a surface 1592 configured to engage rod 1442.

Collar 1580 is configured for axial translation relative to legs 1530, 1550 to move legs 1530, 1550 into a capture configuration to capture bone fastener 1650. Translation of collar 1580 causes surface 1592 to translate into engagement with rod 1442.

Collar 1580 includes a surface 1594 that defines a channel 1596. Channel 1596 is in communication with channel 1528. Channel 1596 is configured for disposal of actuator 1600. Actuator 1600 extends between an end 1602 and an end 1604. End 1602 includes a surface 1606 configured for connection with a surgical instrument, such as, for example, a driver. In some embodiments, surface 1606 includes a hexagonal cross-section to facilitate engagement with a surgical tool or instrument. In some embodiments, surface 1606 may have alternative cross-sections, such as, for example, rectangular, polygonal, hexalobe, oval, or irregular.

End 1604 is fixedly connected with collar 1580 to axially translate collar 1580 to move legs 1530, 1550 into engagement with bone fastener 1650 and engage surface 1592 with rod 1442. In some embodiments, actuator 1600 includes a spring 1607 configured to bias legs 1530, 1550 in the open configuration. Translation of actuator 1600 into support 1520 causes a surface of support 1520 to compress spring 1507 to overcome the bias of spring 1507. Compression of spring 1507 facilitates translation of collar 1580 along legs 1530, 1550 into a capture configuration.

Figure 23:
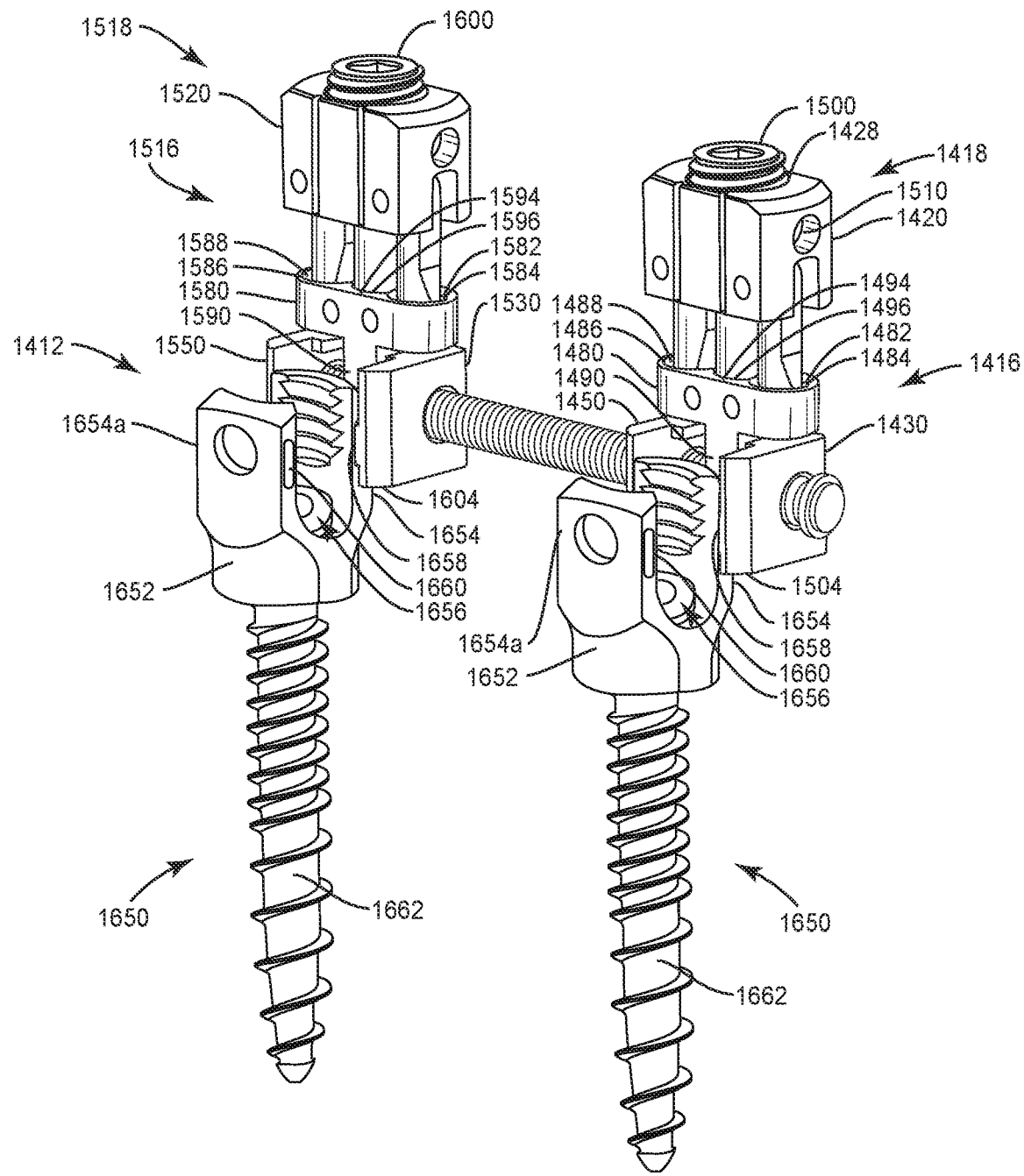
FIG. 23 is a perspective view of components of one embodiment of a surgical system in accordance with the principles of the present disclosure.
Figure 24:
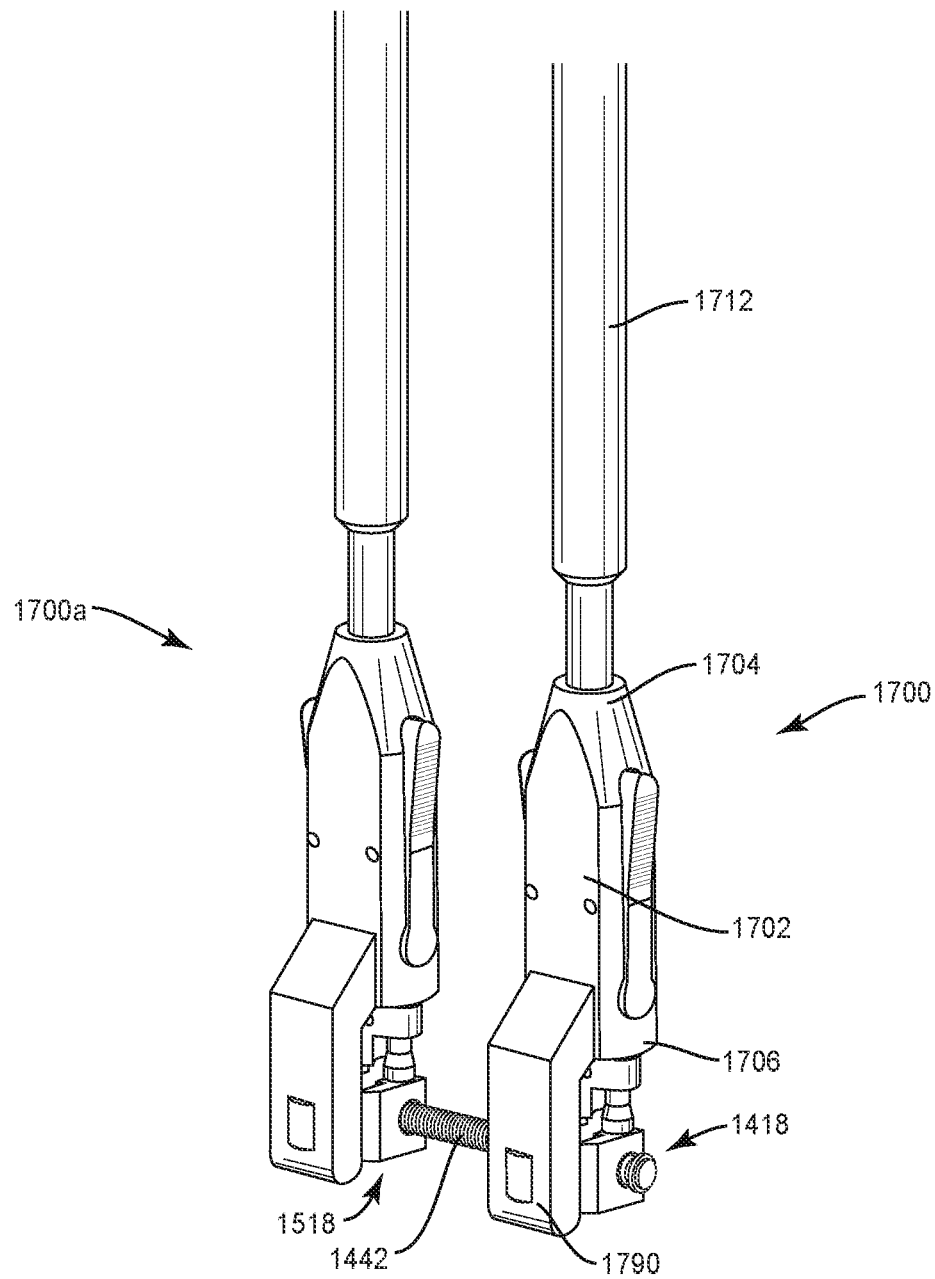
FIG. 24 is a perspective view of components of one embodiment of a surgical system in accordance with the principles of the present disclosure.

Bone fastener 1650 is configured for implantation with tissue, as described herein. Bone fastener 1650 includes a receiver 1652 having a pair of spaced apart arms 1654, 1654a. Receiver 1652 is configured for engagement with connector 1412, as described herein. Arms 1654, 1654a include an inner surface that defines a U-shaped passageway 1656, as shown in FIG. 23. Passageway 1656 is configured for disposal of rod 1442, as described herein.

Arm 1654 includes slot 1658 configured for mating engagement with a surgical instrument, as described herein. Arm 1654a includes slots 1660 configured for a mating engagement with a surgical instrument, as described herein. In some embodiments, slots 1658, 1660 include an elongate configuration. Slots 1658, 1660 are configured for releasable engageable with a surgical instrument to facilitate manipulation of tissue such that movement of a receiver relative to a shaft of bone fastener 1650 is resisted and/or prevented. Bone fastener 1650 includes a shaft 1662 configured for penetrating tissue, as described herein.

In assembly, operation and use, spinal correction system 10, similar to the systems and methods described herein, including connector 1412, as described herein, is employed with a surgical procedure, such as, for example, a PSO procedure for treatment of a spine of a patient including vertebrae V, as shown in FIGS. 24-31. Spinal correction system 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of connector 1412.

Figure 31:
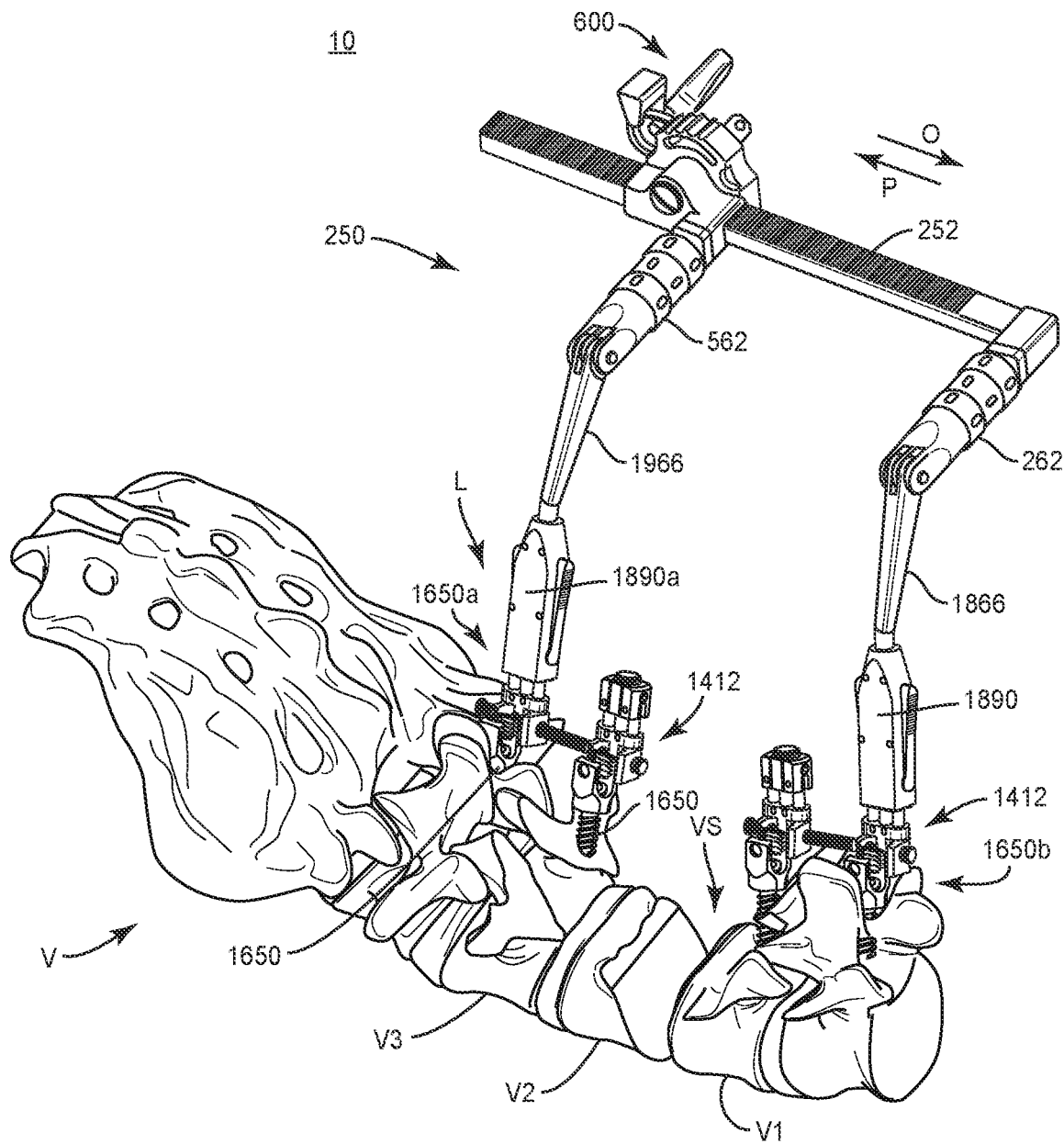
FIG. 31 is a perspective view of components of one embodiment of a surgical system in accordance with the principles of the present disclosure disposed with vertebrae.

In use, to treat the affected section of vertebrae V, similar to that described herein, a medical practitioner obtains access to a surgical site including vertebrae V, as shown in FIG. 31, in any appropriate manner, such as through incision and retraction of tissues. An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region. Bone fasteners 1650 are engaged with vertebrae V along a lateral side L of vertebrae V. In some embodiments, bone fasteners 1650 are disposed in pairs 1650a, 1650b alongside L. In some embodiments, pair 1650a is disposed inferior to vertebra V2 and pair 1650b is disposed superior to vertebra V2.

Supports 1418, 1518 are connected to a surgical instrument, such as, for example, an inserter 1700 and an inserter 1700a, similar to inserter 1700 described herein, as shown in FIGS. 24-29. Inserter 1700 includes a member, such as, for example, a sleeve 1702. Sleeve 1702 extends between an end 1704 and an end 1706 defining an axis L4. End 1704 includes a surface 1708 that defines an opening 1710. Opening 1710 is configured for disposal of a driver 1712, as described herein. Sleeve 1702 includes a surface 1714 that defines a channel 1716. Channel 1716 is disposed in communication with opening 1710 to facilitate insertion and manipulation of driver 1712, as described herein. End 1706 includes a surface 1720 that defines a cavity 1722. Cavity 1722 includes walls 1724a, 1724b, 1724c and 1724d that define a tubular configuration. Cavity 1722 is configured to capture and engage support 1418, as described herein.

Wall 1724b includes a surface 1726 that defines an elongate opening 1728. Opening 1728 is configured for moveable disposal of an arm 1740, as described herein. Wall 1724d includes a surface 1730 that defines an elongate opening 1732. Opening 1732 is configured for moveable disposal of an arm 1742, as described herein. Arms 1740, 1742 are configured to engage detents 1510, 1514 to capture support 1418.

Figure 26:
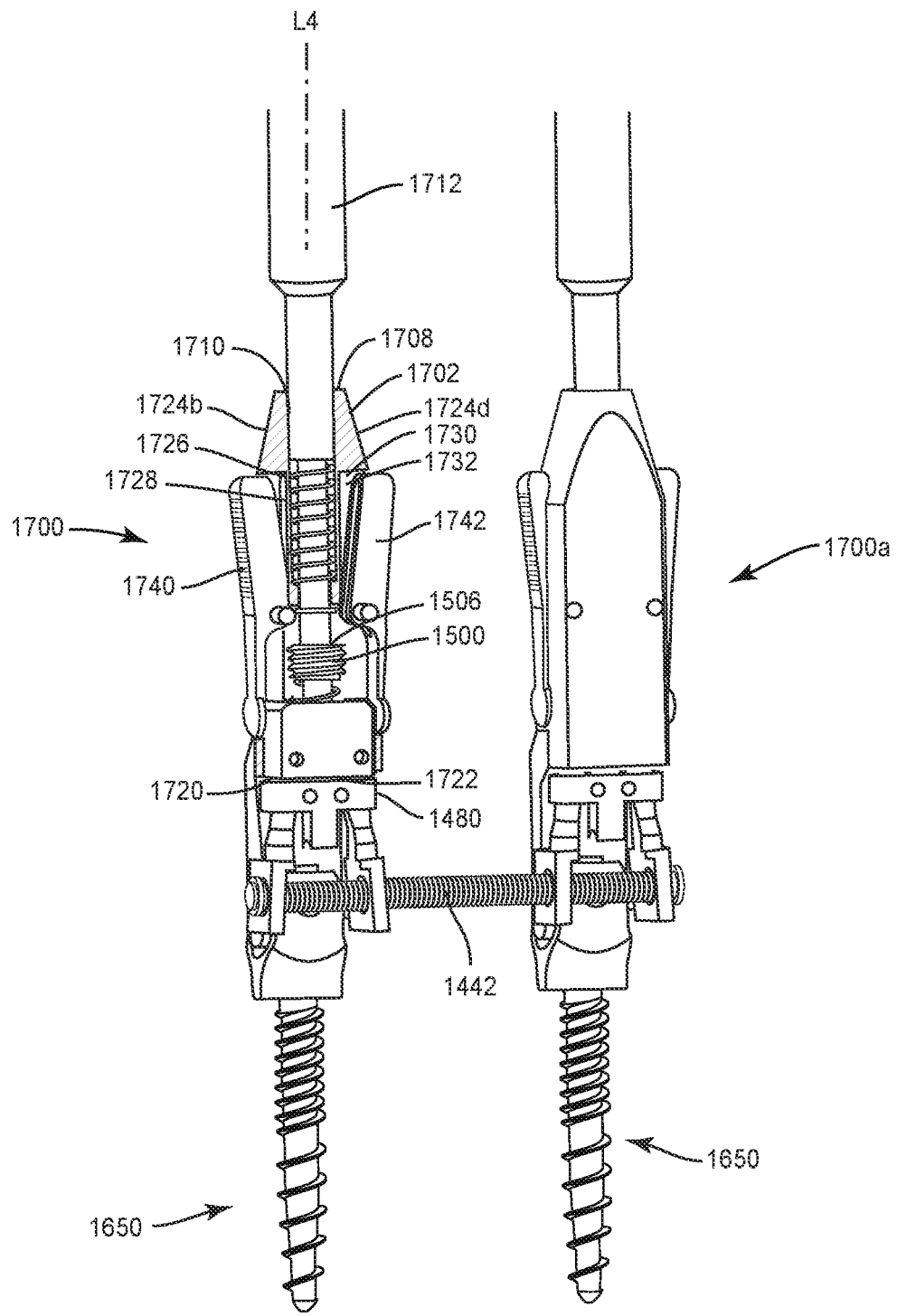
FIG. 26 is a perspective view in part cutaway of components of one embodiment of a surgical system in accordance with the principles of the present disclosure.
Figure 27:
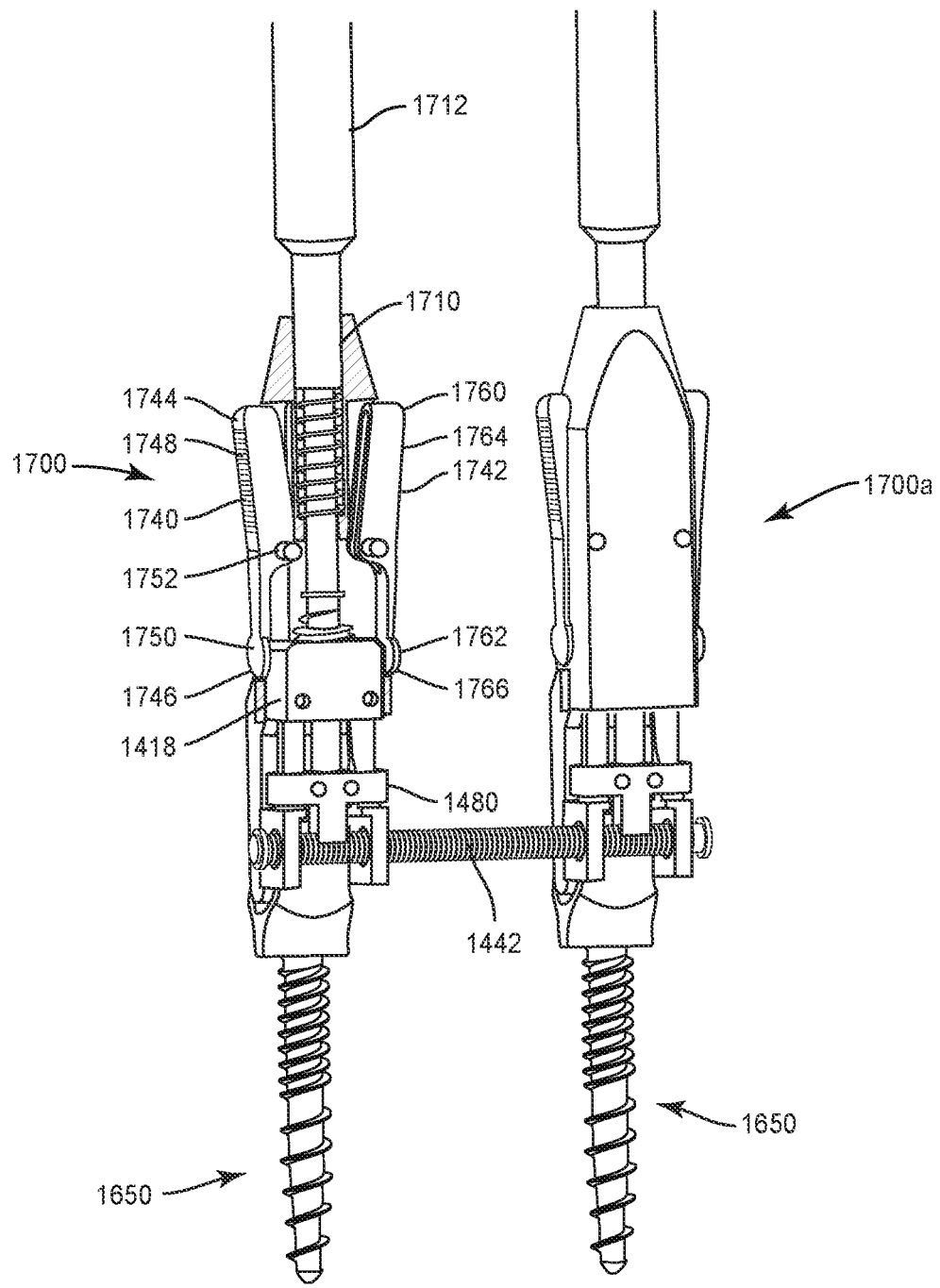
FIG. 27 is a perspective view in part cutaway of components of one embodiment of a surgical system in accordance with the principles of the present disclosure.

Arms 1740, 1742 are configured for relative movement to capture support 1418 in a quick release configuration, as described herein. Arm 1740 extends between an end 1744 and an end 1746. End 1744 includes a gripping surface 1748 configured to facilitate manipulation of arm 1740. End 1746 includes a capture element 1750. Capture element 1750 is configured to engage detent 1510. Arm 1740 is connected with sleeve 1702 by a spring 1752. Spring 1752 is configured to resiliently bias arm 1740 in a closed configuration, as shown in FIG. 26.

Figure 28:
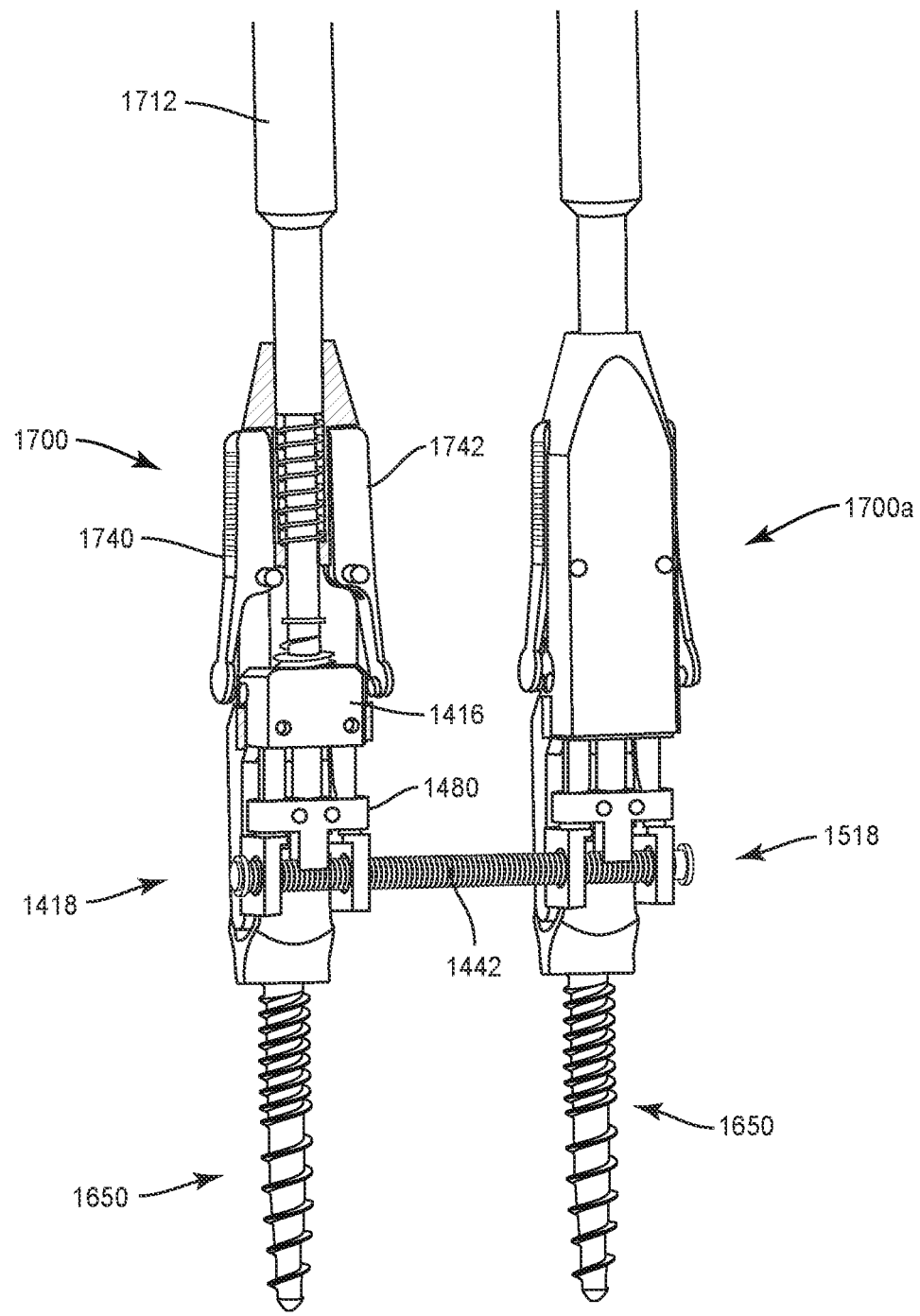
FIG. 28 is a perspective view in part cutaway of components of one embodiment of a surgical system in accordance with the principles of the present disclosure.
Figure 29:
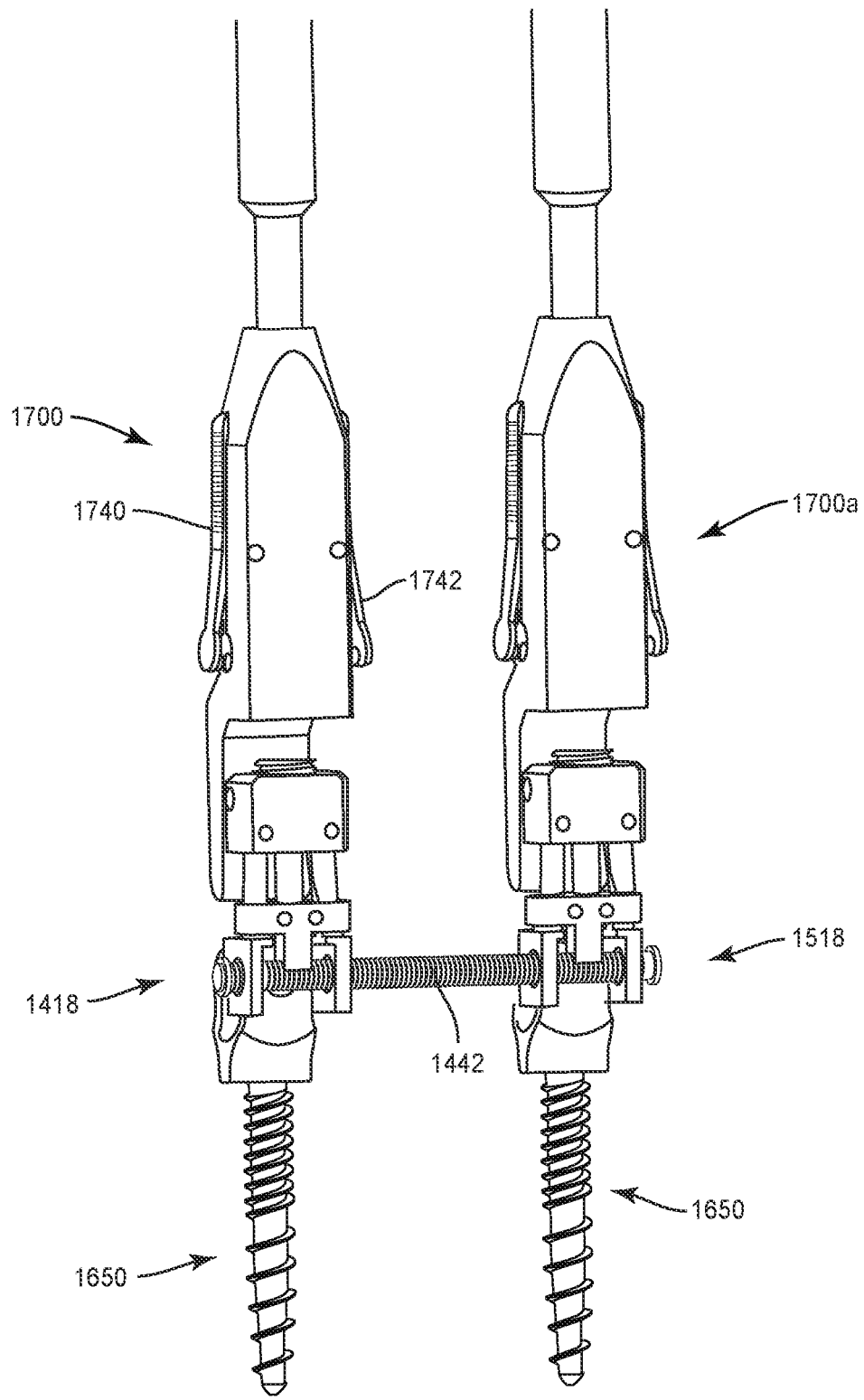
FIG. 29 is a perspective view of components of one embodiment of a surgical system in accordance with the principles of the present disclosure.

Arm 1742 extends between an end 1760 and an end 1762. End 1760 includes a gripping surface 1764 configured to facilitate manipulation of arm 1742. End 1762 includes a capture element 1766. Capture element 1766 is configured to engage detent 1514. Arm 1742 is connected with sleeve 1702 by a spring 1768. Spring 1768 is configured to resiliently bias arm 1742 in a closed configuration, as shown in FIG. 26. In some embodiments, arms 1740, 1742 are resiliently biased in a closed configuration to capture support 1418, as shown in FIG. 26, and in an open configuration, as shown in FIG. 28, as described herein. Movement of arms 1740, 1742 is configured to engage support 1418 in a quick release configuration such that sleeve 1702 and support 1418 are releasably fixable without tools, via biased arms 1740, 1742 to facilitate intra-operative connection, similar to that described herein.

Figure 25:
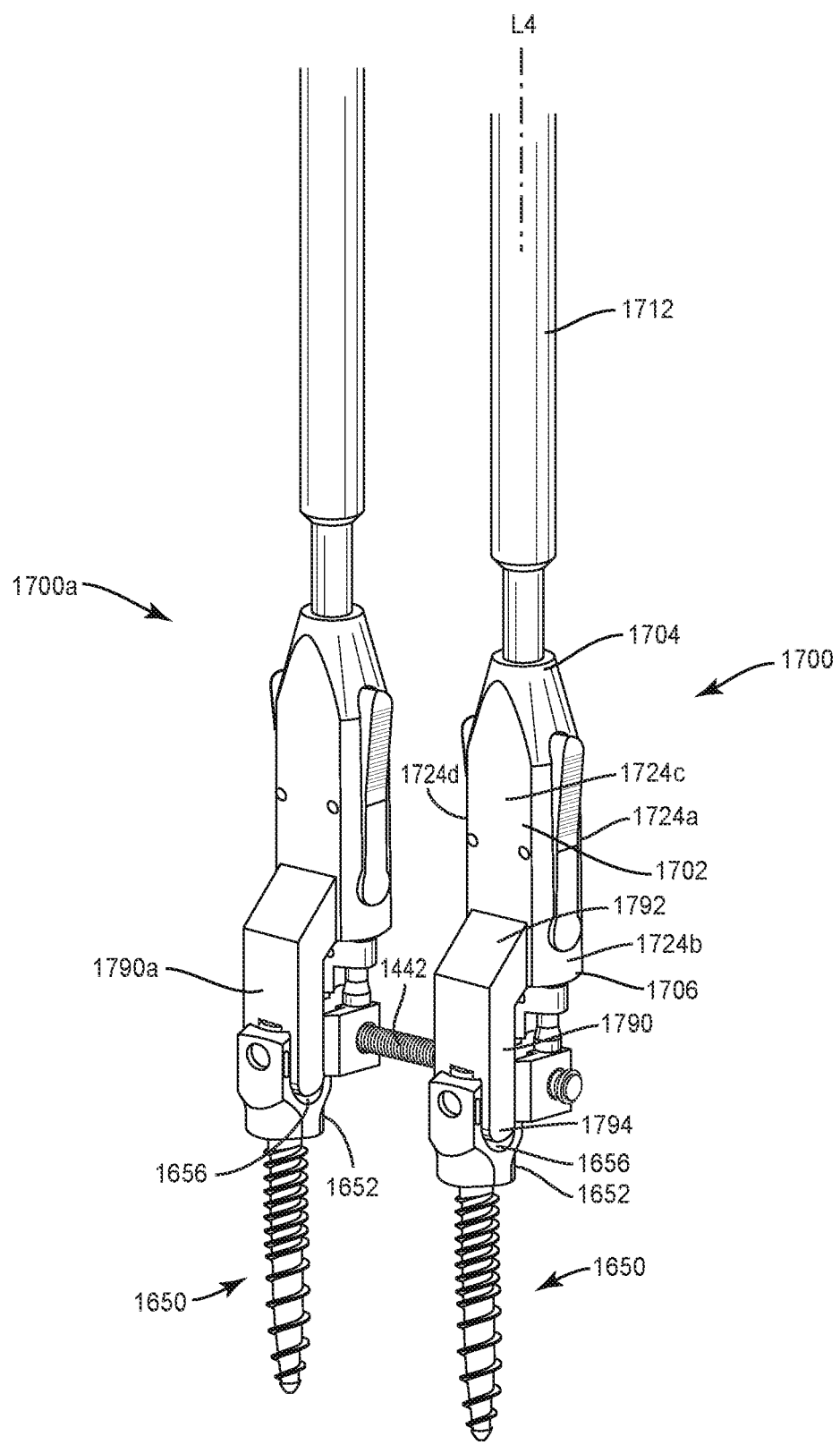
FIG. 25 is a perspective view of components of one embodiment of a surgical system in accordance with the principles of the present disclosure.

Inserter 1700 includes a projection, such as, for example, an extension 1790. Extension 1790 is disposed offset from axis L4, as shown in FIG. 25. In some embodiments, extension 1790 may be variously oriented relative to axis L4, such as, for example, transverse and/or angled. Extension 1790 extends between an end 1792 and an end 1794. End 1792 is configured for connection with sleeve 1702. In some embodiments, extension 1790 is monolithically formed with sleeve 1702. End 1794 is configured for disposal with passageway 1656 of bone fasteners 1650 to facilitate engagement therewith.

Inserters 1700, 1700a are configured to guide supports 1418, 1518 for connection with bone fasteners 1650. As driver 1712 translates into engagement with actuator 1500, actuator 1500 causes translation of collar 1480 over legs 1430, 1450 to move legs 1430, 1450 into a closed configuration. In the closed configuration, legs 1430, 1450 engage slots 1658 to capture bone fastener 1650. Collar 1480 is translated into engagement with rod 1442 to fix rod 1442 with support 1418 and bone fastener 1650. Similarly, inserter 1700a includes an extension 1790a and is manipulated to engage support 1518 with bone fastener 1650. Supports 1418, 1518 are connected with bone fasteners 1650 to resist and/or prevent movement of receivers 1652. In some embodiments, bone fasteners 1650 include 6 degrees of freedom of movement, similar to that described herein, and supports 1418, 1518 are connected with bone fasteners 1650 to resist and/or prevent movement of receivers 1652 in 5 of 6 degrees of freedom of movement such that receivers 1652 are free to roll in a medial lateral direction. Inserters 1700, 1700a include a quick release configuration, as described herein, and are removed from supports 1418, 1518.

Figure 30:
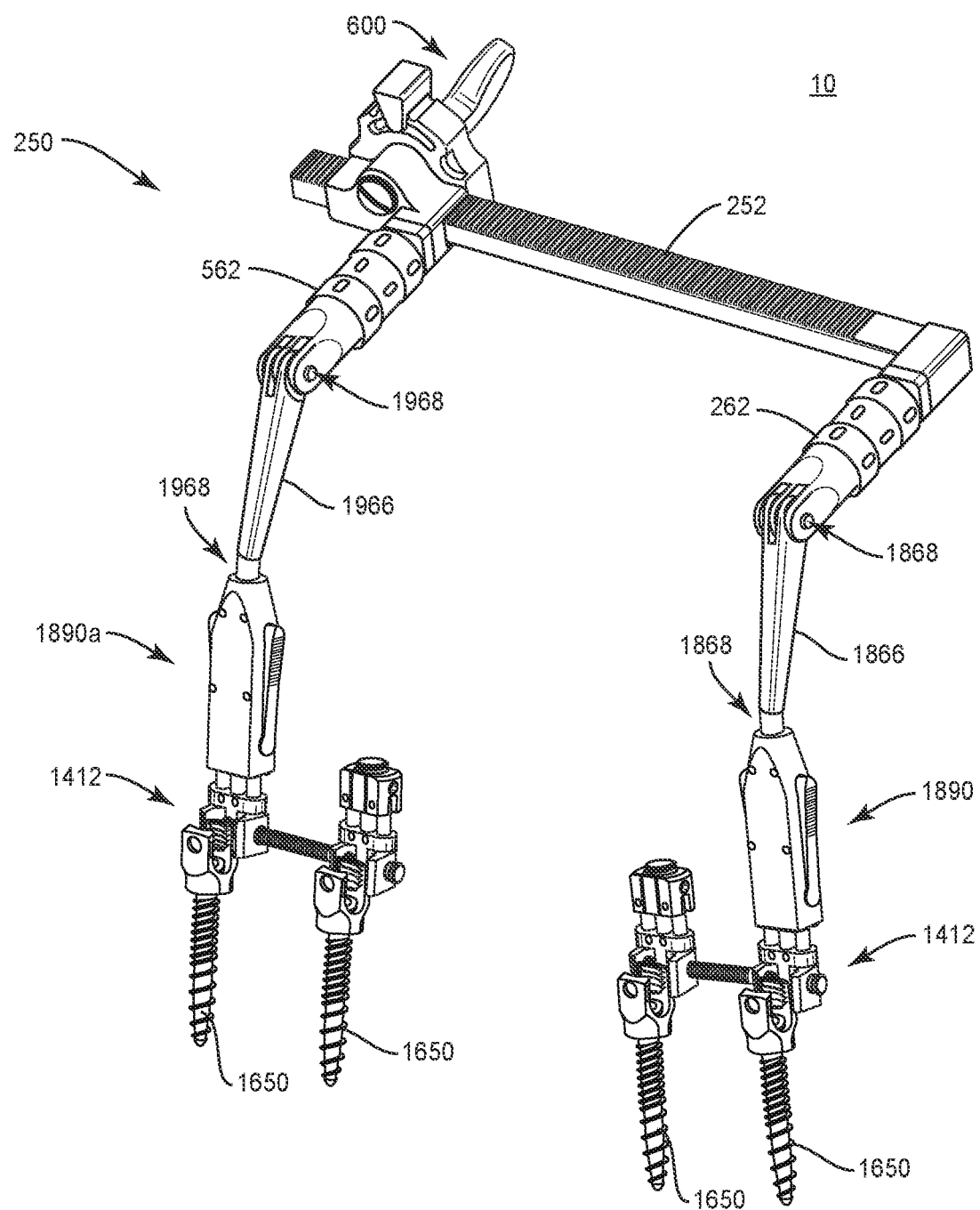
FIG. 30 is a perspective view of components of one embodiment of a surgical system in accordance with the principles of the present disclosure.

Referring to FIGS. 30 and 31, surgical instrument 250, as described herein, includes arm 262 connected with a linear part 1866, similar to part 266 described herein, and arm 562 connected with a linear part 1966, similar to part 566 described herein. Part 1866 is connected with a sleeve 1890, similar to sleeve 1700 described herein and part 1966 is connected with a sleeve 1890a, similar to sleeve 1700 described herein. In some embodiments, rack 252 and part 1866 define a joint, such as, for example a third level joint of arm 262 configured to allow part 1866 to pivot relative to rack 252. A locking mechanism similar to locking mechanism 276 may be manipulated to tighten the third level joint of arm 262 to fix part 1866 relative to rack 252. The locking mechanism may be manipulated to loosen the third level joint of arm 262 to allow part 1866 to pivot relative to rack 252. In some embodiments, rack 252 and part 1966 define a joint, such as, for example a third level joint of arm 562 configured to allow part 1966 to pivot relative to rack 252. A locking mechanism similar to locking mechanism 576 may be manipulated to tighten the third level joint of arm 562 to fix part 1966 relative to rack 252. The locking mechanism may be manipulated to loosen the third level joint of arm 562 to allow part 1966 to pivot relative to rack 252.

In some embodiments, part 1866 is pivotable relative to arm 262 about a hinge pin 1868 and part 1966 is pivotable relative to arm 562 about a hinge pin 1968. In some embodiments, hinge pin 1868 defines a joint, such as, for example a second level joint of arm 262 configured to allow part 1866 to pivot relative to arm 262. A locking mechanism similar to locking mechanism 276 may be manipulated to tighten the second level joint of arm 262 to fix part 1866 relative to arm 262, as discussed herein. The locking mechanism may be manipulated to loosen the second level joint of arm 262 to allow part 1866 to pivot relative to arm 262, as discussed herein. In some embodiments, hinge pin 1968 defines a joint, such as, for example a second level joint of arm 562 configured to allow part 1966 to pivot relative to arm 562. A locking mechanism similar to locking mechanism 576 may be manipulated to tighten the second level joint of arm 562 to fix part 1966 relative to arm 562, as discussed herein. The locking mechanism may be manipulated to loosen the second level joint of arm 562 to allow part 1966 to pivot relative to arm 562, as discussed herein.

In some embodiments, part 1866 and sleeve 1890 define a joint, such as, for example, a first level joint 1868 of arm 262 configured to allow sleeve 1890 to pivot relative to part 1866. Tightening first level joint 1868 of arm 262 causes sleeve 1890 to be fixed relative to part 1866. Loosing first level joint 1868 of arm 262 causes sleeve 1890 to pivot relative to part 1866. In some embodiments, part 1966 and sleeve 1890a define a joint, such as, for example, a first level joint 1968 of arm 562 configured to allow sleeve 1890a to pivot relative to part 1966. Tightening first level joint 1968 of arm 562 causes sleeve 1890a to be fixed relative to part 1966. Loosing first level joint 1968 of arm 562 causes sleeve 1890a to pivot relative to part 1966.

Surgical instrument 250 is connected with supports 1418, 1518 disposed along a side of vertebrae V, as shown in FIG. 31. In some embodiments, part 1866 and/or part 1966 are rotatable relative to arm 262, arm 562, rack 252, the spinal constructs and/or vertebrae V to orient sleeve 1890 and/or sleeve 1890a in a selected orientation to capture one or more connectors 1412. In some embodiments, part 1866 is fixed in a selected orientation with locking mechanism 276 and part 1966 is fixed in a selected orientation with locking mechanism 576, as described herein. Sleeves 1890, 1890a are translated over supports 1418, 1518 and engaged with slots 1510, 1514 in a quick release configuration, as described herein. Slots 1510, 1514 are configured for a mating engagement with one or a plurality of alternate surgical instruments in a quick release configuration, as described herein, to facilitate the interchangeability of connectors 1412 with alternate surgical instruments, as described herein.

Lock 600 is manipulated to axially translate arm 562 along rack 252 relative to arm 262 to facilitate compression and/or distraction of vertebrae V. Translation of arm 562 relative to arm 262 along rack 252, in a direction shown by arrow P in FIG. 31, distracts vertebrae V to open vertebral space VS. In some embodiments, a spinal implant, such as, for example, an intrabody implant is disposed within vertebral space VS, as described herein.

Translation of arm 562, in a direction shown by arrow O in FIG. 31, is configured to compress vertebrae V to achieve correction, for example, a selected lordosis. In some embodiments, surgical instrument 250 manipulates vertebrae V during a surgical correction treatment to rotate, displace, pull, twist or align vertebrae V to a selected orientation for sagittal, coronal and/or axial correction. In some embodiments, surgical instrument 250 applies derotation forces to vertebrae V for correction of vertebrae V.

In some embodiments, spinal correction system 10 includes surgical instrument 250, a surgical instrument 250a that is the same or similar to surgical instrument 250 and a plurality of spinal constructs or temporary spinal rods, such as, for example, a plurality of short rods, a plurality of connectors that are the same or similar to connector 12 and/or a plurality of connectors that are the same or similar to connector 1412. As shown in FIGS. 32-36, surgical instrument 250a includes a sleeve 290b that is the same or similar to sleeve 290 and a sleeve 290c that is the same or similar to sleeve 290a. Spinal correction system 10 may also be employed with other surgical procedures, such as, for example, discectomy, laminectomy, fusion, laminotomy, laminectomy, nerve root retraction, foraminotomy, facetectomy, decompression, spinal nucleus or disc replacement and bone graft and implantable prosthetics including plates, rods, and bone engaging fasteners.

MAS screws 200 are engaged with vertebrae V along lateral side L of vertebrae V, as shown in FIG. 15. In some embodiments, MAS screws 200 are disposed in pairs 200a, 200b alongside L. In some embodiments, pair 200a is disposed inferior to vertebra V2 and pair 200b is disposed superior to vertebra V2. DRMAS 220 are engaged along a contralateral side CL of vertebrae V, as shown in FIG. 15. In some embodiments, DRMAS screws 220 are disposed in pairs 220a, 220b alongside CL. In some embodiments, pair 220a is disposed inferior to vertebra V2 and pair 220b is disposed superior to vertebra V2. The receivers of MAS 200 and DRMAS 220 are configured to rotate within six degrees relative to the shafts of MAS 200 and DRMAS 220.

Connectors, such as, for example, temporary spinal rods are engaged with pairs 200a, 200b, 220a, 220b. For example, in some embodiments, connector 12 is engaged with pair 200a such that support 18 is disposed adjacent vertebra V2 and rod 36 extends in an inferior orientation to an adjacent MAS 200, as shown in FIG. 16. Set screw 80 is engaged with receiver 202 disposed adjacent vertebrae V2. A connector 12a that is the same or similar to connector 12 is engaged with pair 200b such that support 18 is disposed adjacent vertebra V2 and rod 36 extends in a superior orientation to an adjacent MAS 200. Set screw 80 is engaged with receiver 202 disposed adjacent vertebrae V2. A connector 12b that is the same or similar to connector 12 is engaged with pair 220a such that support 18 is disposed adjacent vertebra V2 and rod 36 extends in an inferior orientation to an adjacent DRMAS 220, as shown in FIG. 16. Set screw 80 is engaged with receiver 202 disposed adjacent vertebrae V2. A connector 12c that is the same or similar to connector 12 is engaged with pair 220b such that support 18 is disposed adjacent vertebra V2 and rod 36 extends in a superior orientation to an adjacent DRMAS 220. Set screw 80 is engaged with receiver 202 disposed adjacent vertebrae V2.

A surgical instrument, such as, for example, a driver is connected with set screw 80 and/or set screw 180 to facilitate engagement of supports 18, 118. Support 118 is engaged with pair 200a such that set screw 180 is engaged with the adjacent MAS screw 200 receiver 202 and rod 36, as shown in FIG. 17. Support 118 is engaged with pair 200b such that set screw 180 is engaged with the adjacent receiver 202 and rod 36. Support 118 is engaged with pair 220a such that set screw 180 is engaged with the adjacent DRMAS 220 receiver 222 and rod 36. Support 118 is engaged with pair 220b such that set screw 180 is engaged with the adjacent DRMAS 220 receiver 222 and rod 36.

Attachment of connectors 12, 12a, 12b, 12c with pairs 200a, 200b, 220a, 220b resists and/or prevents movement of the receivers of MAS 200 and DRMAS 220 relative to the shafts of MAS 200 and DRMAS 220 and/or vertebrae attached therewith. In some embodiments, movement of the receivers of MAS 200 and DRMAS 220 relative to the shafts of MAS 200 and DRMAS 220 and/or vertebrae can be prevented in one or a plurality of degrees of freedom of the fasteners, as described herein.

Figure 32:
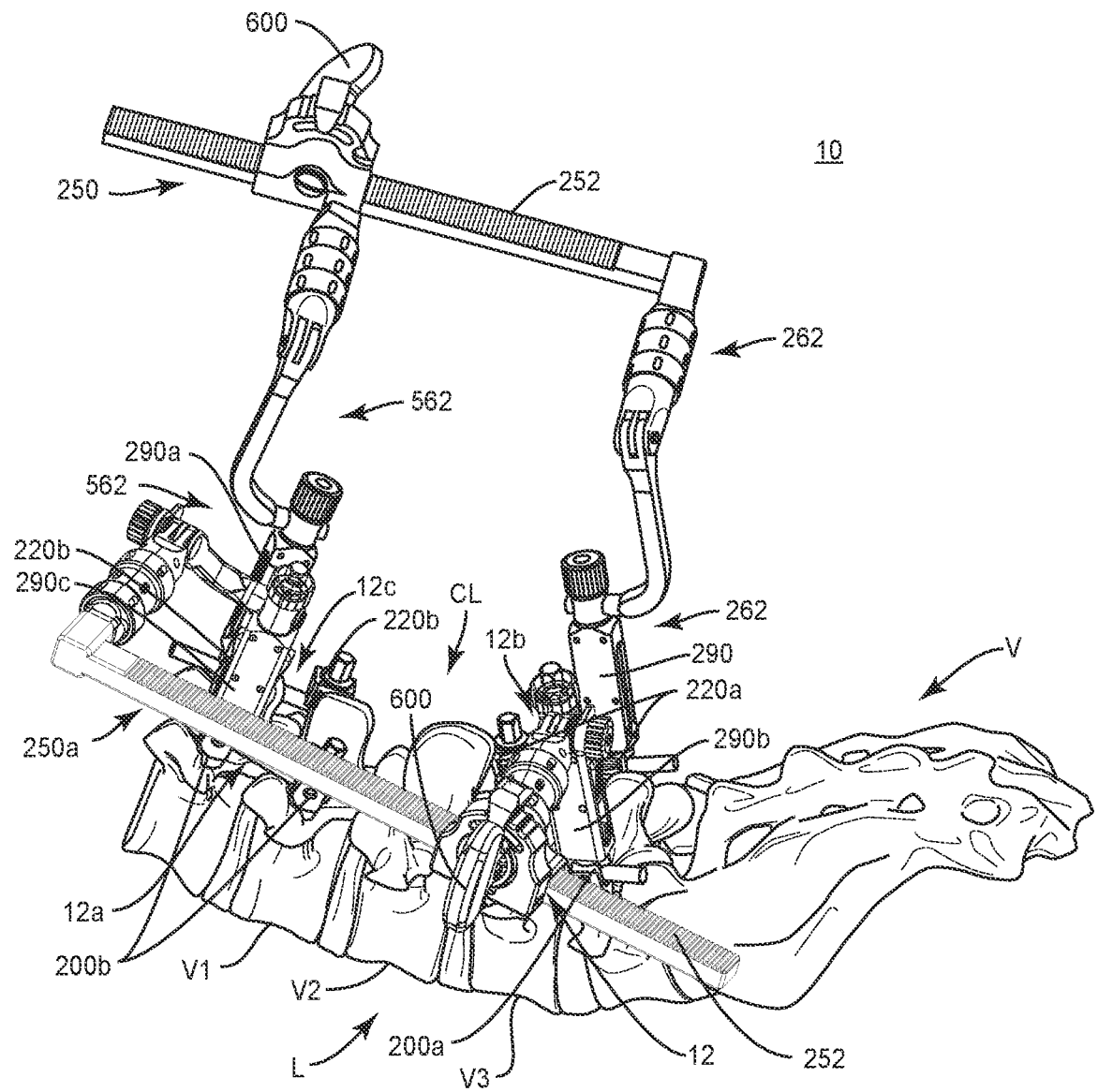
FIG. 32 is a perspective view of components of one embodiment of a surgical system in accordance with the principles of the present disclosure disposed with vertebrae.

Surgical instrument 250 is connected with supports 118 disposed alongside CL of vertebrae V and surgical instrument 250a is connected with supports 118 disposed alongside L of vertebrae V, as shown in FIG. 32. In particular, sleeve 290 is connected with support 118 that is connected with pair 220a alongside CL; sleeve 290a is connected with support 118 that is connected with pair 220b alongside CL; sleeve 290b is connected with support 118 that is connected with pair 200a alongside L; and sleeve 290C is connected with support 118 that is connected with pair 200b alongside L. In some embodiments, connectors 1412 are attached with pairs 200a, 200b, 220a, 220b in place of connectors 12, 12a, 12b, 12c and surgical instruments 250, 250a are connected with connectors 1412, as discussed herein.

In some embodiments, one or more of the joints of arms 262, 562 of surgical instrument 250 and/or one or more of the joints of arms 262, 562 of surgical instrument 250a are loosened prior to connecting surgical instrument 250 and/or surgical instrument 250a with connectors 12, 12a, 12b and/or 12c. For example, in some embodiments, the first level joint of arm 262 of surgical instrument 250 is loosened to allow sleeve 290 to pivot relative to part 266 prior to connecting surgical instrument 250 with connector 12b. In some embodiments, the first level joint of arm 562 of surgical instrument 250 is loosened to allow sleeve 290a to pivot relative to part 566 prior to connecting surgical instrument 250 with connector 12c.

In some embodiments, the second level joint of arm 262 of surgical instrument 250 is loosened to allow part 264 to pivot relative to part 266 of surgical instrument 250 prior to connecting surgical instrument 250 with connector 12b. In some embodiments, the second level joint of arm 562 of surgical instrument 250 is loosened to allow part 564 to pivot relative to part 566 of surgical instrument 250 prior to connecting surgical instrument 250 with connector 12c.

In some embodiments, the third level joint of arm 262 of surgical instrument 250 is loosened to allow part 264 to pivot relative to rack 252 of surgical instrument 250 prior to connecting surgical instrument 250 with connector 12b. In some embodiments, the third level joint of arm 562 of surgical instrument 250 is loosened to allow part 564 to pivot relative to rack 252 of surgical instrument 250 prior to connecting surgical instrument 250 with connector 12*c*.

In some embodiments, the first level joint of arm 262 of surgical instrument 250*a* is loosened to allow sleeve 290*b* to pivot relative to part 266 prior to connecting surgical instrument 250*a* with connector 12. In some embodiments, the first level joint of arm 562 of surgical instrument 250*a* is loosened to allow sleeve 290*c* to pivot relative to part 566 prior to connecting surgical instrument 250*a* with connector 12*a*.

In some embodiments, the second level joint of arm 262 of surgical instrument 250*a* is loosened to allow part 264 to pivot relative to part 266 of surgical instrument 250*a* prior to connecting surgical instrument 250 with connector 12. In some embodiments, the second level joint of arm 562 of surgical instrument 250*a* is loosened to allow part 564 to pivot relative to part 566 of surgical instrument 250*a* prior to connecting surgical instrument 250 with connector 12*a*.

In some embodiments, the third level joint of arm 262 of surgical instrument 250*a* is loosened to allow part 264 to pivot relative to rack 252 of surgical instrument 250*a* prior to connecting surgical instrument 250*a* with connector 12. In some embodiments, the third level joint of arm 562 of surgical instrument 250 is loosened to allow part 564 to pivot relative to rack 252 of surgical instrument 250*a* prior to connecting surgical instrument 250*a* with connector 12*a*.

In some embodiments, one or more of the joints of arms 262, 562 of surgical instrument 250 and/or one or more of the joints of arms 262, 562 of surgical instrument 250*a* are tightened after connecting surgical instrument 250 and/or surgical instrument 250*a* with connectors 12, 12*a*, 12*b* and/or 12*c*. For example, in some embodiments, the first level joint of arm 262 of surgical instrument 250 is tightened to fix sleeve 290 relative to part 266 after connecting surgical instrument 250 with connector 12*b*. In some embodiments, the first level joint of arm 562 of surgical instrument 250 is tightened to fix sleeve 290*a* to part 566 after connecting surgical instrument 250 with connector 12*c*. In some embodiments, the first level joint of arm 262 and/or arm 562 of surgical instrument 250 is/are tightened while ensuring that vertebrae V are positioned as desired.

In some embodiments, the second level joint of arm 262 of surgical instrument 250 is tightened to fix part 264 relative to part 266 of surgical instrument 250 after connecting surgical instrument 250 with connector 12*b*. In some embodiments, the second level joint of arm 562 of surgical instrument 250 is tightened to fix part 564 to pivot relative to part 566 of surgical instrument 250 after connecting surgical instrument 250 with connector 12*c*. In some embodiments, the second level joint of arm 262 and/or arm 562 of surgical instrument 250 is/are tightened while ensuring that vertebrae V are positioned as desired.

In some embodiments, the third level joint of arm 262 of surgical instrument 250 is tightened to fix part 264 relative to rack 252 of surgical instrument 250 after connecting surgical instrument 250 with connector 12*b*. In some embodiments, the third level joint of arm 562 of surgical instrument 250 is tightened to fix part 564 relative to rack 252 of surgical instrument 250 after connecting surgical instrument 250 with connector 12*c*. In some embodiments, the third level joint of arm 262 and/or arm 562 of surgical instrument 250 is/are tightened while ensuring that vertebrae V are positioned as desired. In some embodiments, at least one of the joints of arm 262 of surgical instrument 250 and/or at least one of the joints of arm 262 of surgical instrument 250 is/are tightened before surgical instrument 250*a* is attached to connectors 12, 12*a*.

In some embodiments, the first level joint of arm 262 of surgical instrument 250*a* is tightened to fix sleeve 290*b* relative to part 266 after connecting surgical instrument 250*a* with connector 12. In some embodiments, the first level joint of arm 562 of surgical instrument 250*a* is tightened to fix sleeve 290*c* relative to part 566 after connecting surgical instrument 250*a* with connector 12*a*. In some embodiments, the first level joint of arm 262 and/or arm 562 of surgical instrument 250*a* is/are tightened while ensuring that vertebrae V are positioned as desired. In some embodiments, the first level joints of arms 262, 562 of surgical instrument 250 and the first level joints of arms 262, 562 of surgical instrument 250*a* are tightened before the second level joints of arms 262, 562 of surgical instrument 250 are tightened.

In some embodiments, the second level joint of arm 262 of surgical instrument 250*a* is tightened to fix 264 to pivot relative to part 266 of surgical instrument 250*a* after connecting surgical instrument 250 with connector 12. In some embodiments, the second level joint of arm 562 of surgical instrument 250*a* is tightened to fix part 564 relative to part 566 of surgical instrument 250*a* after connecting surgical instrument 250 with connector 12*a*. In some embodiments, the second level joint of arm 262 and/or arm 562 of surgical instrument 250*a* is/are tightened while ensuring that vertebrae V are positioned as desired.

In some embodiments, the third level joint of arm 262 of surgical instrument 250*a* is tightened to fix part 264 relative to rack 252 of surgical instrument 250*a* after connecting surgical instrument 250*a* with connector 12. In some embodiments, the third level joint of arm 562 of surgical instrument 250 is tightened to fix part 564 relative to rack 252 of surgical instrument 250*a* after connecting surgical instrument 250*a* with connector 12*a*. In some embodiments, the third level joint of arm 262 and/or arm 562 of surgical instrument 250*a* is/are tightened while ensuring that vertebrae V are positioned as desired. In some embodiments, the first level joints of arms 262, 562 of surgical instrument 250 and at least one of the joints of arms 262, 562 of surgical instrument 250*a* are tightened the second level joints of arms 262, 562 of surgical instrument 250 are tightened.

In some embodiments, a rack lock, such as, for example, lock 600 of surgical instrument 250 and/or lock 600 of surgical instrument 250*a* is/are tightened after one or more of the joints of arms 262, 562 of surgical instrument 250 and/or one or more of the joints of arms 262, 562 of surgical instrument 250*a* are tightened to fix arm 264 of surgical instrument 250 relative to arm 564 of surgical instrument 250 and/or to fix arm 264 of surgical instrument 250*a* relative to arm 564 of surgical instrument 250*a*. In some embodiments, the rack lock of surgical instrument 250 and/or the rack lock of surgical instrument 250*a* is/are tightened while ensuring that vertebrae V are positioned as desired.

Figure 33:
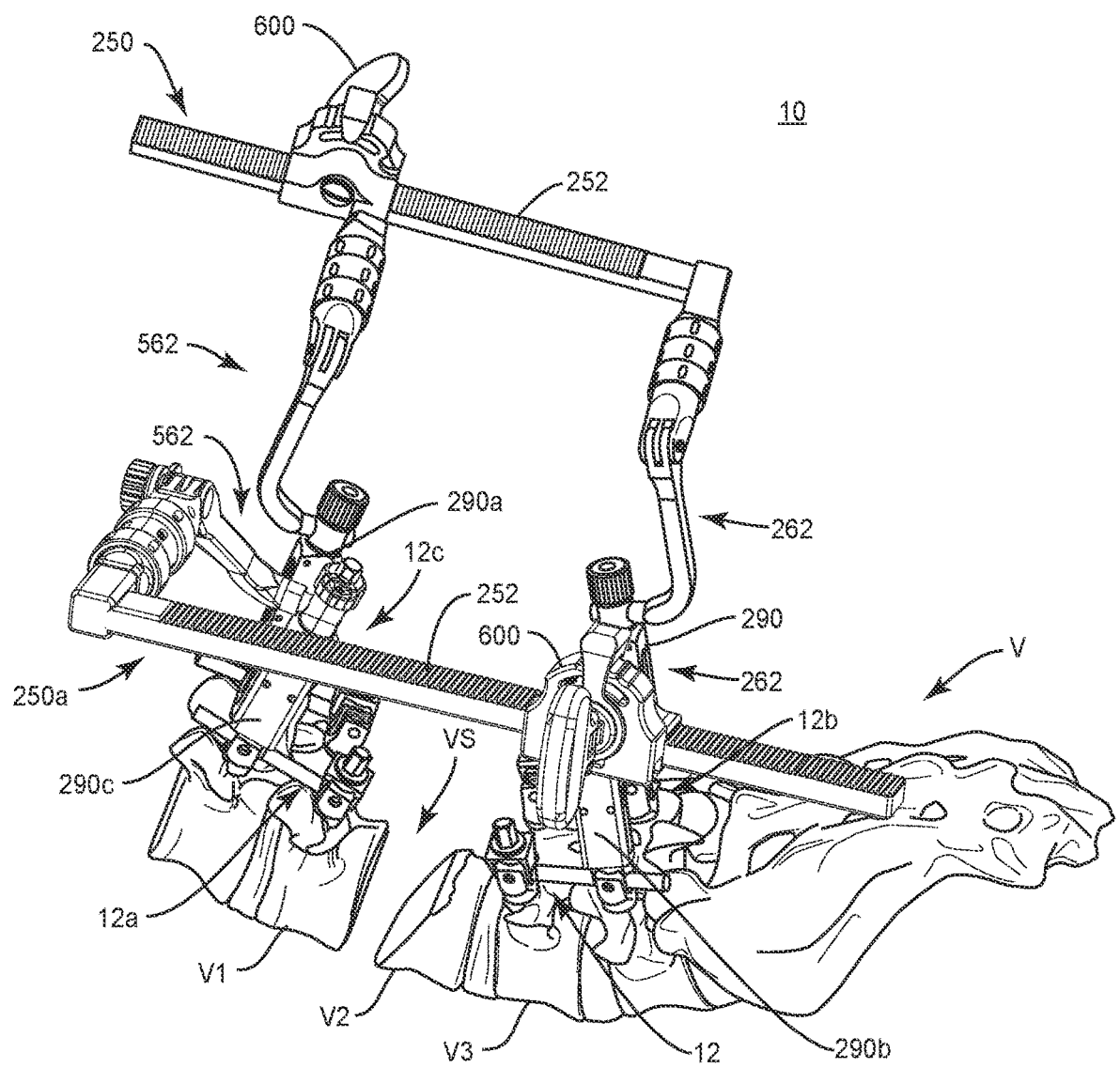
FIG. 33 is a perspective view of components of one embodiment of a surgical system in accordance with the principles of the present disclosure disposed with vertebrae.

In some embodiments, a surgical instrument, such as, for example, an osteotome is utilized to facilitate removing all or a portion of vertebra V2 and adjacent intervertebral disc tissue to define a vertebral space VS after the rack lock of surgical instrument 250 and/or the rack lock of surgical instrument 250*a* is/are tightened, as shown in FIG. 33. In some embodiments, vertebral space VS can include posterior portions of the spine, such as, for example, pedicles, laminae and/or spinous process. In some embodiments, a wedge portion of bone and/or other tissue is removed from a selected vertebra and adjacent intervertebral disc tissue remains intact.

Figure 34:
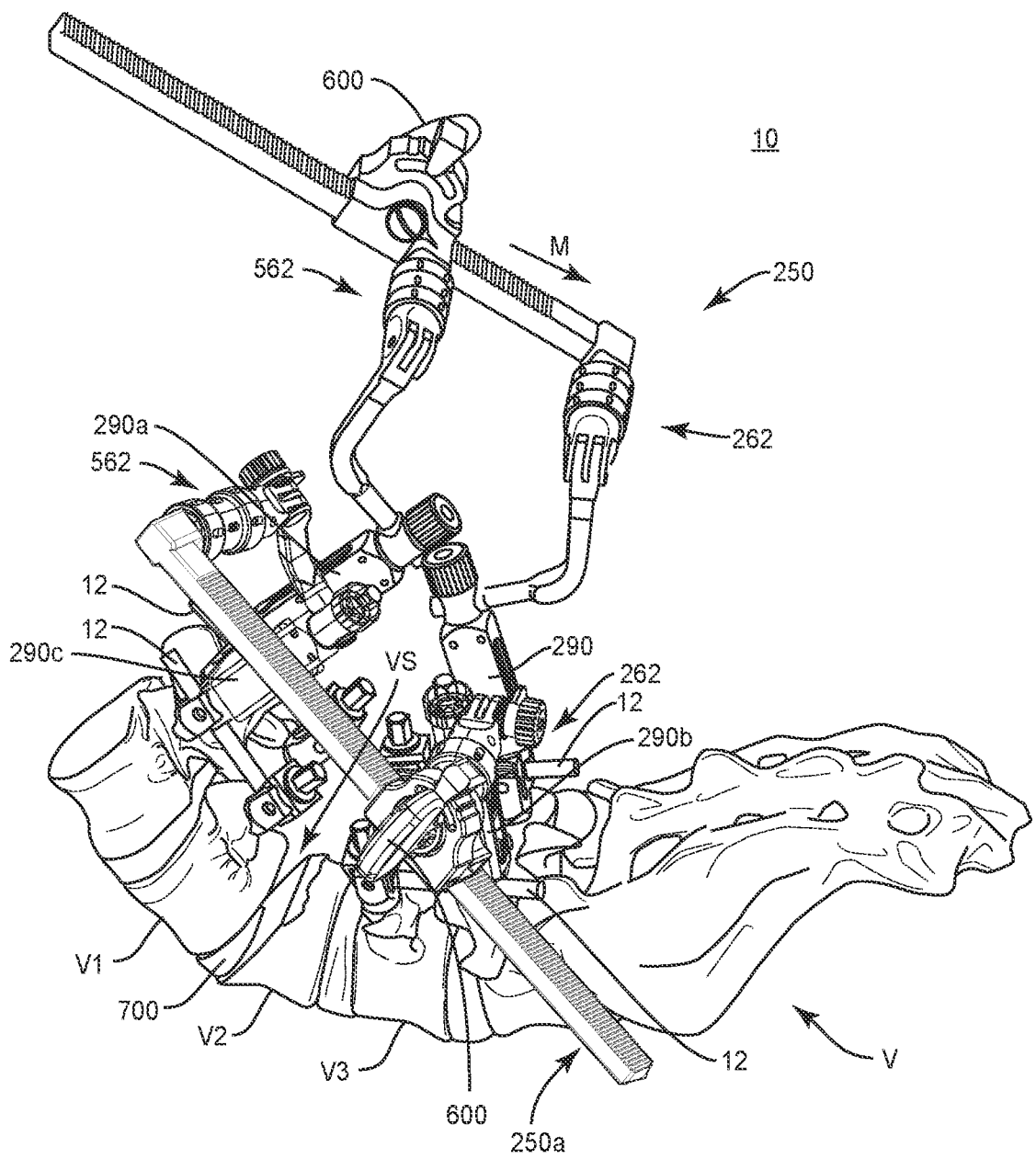
FIG. 34 is a perspective view of components of one embodiment of a surgical system in accordance with the principles of the present disclosure disposed with vertebrae.

In some embodiments, vertebrae V are selectively distracted after the osteotome creates vertebral space VS to better accommodate a spinal implant, such as, for example, implant 700. In some embodiments, vertebrae V are selectively distracted by loosening and/or unlocking the rack lock of surgical instrument 250 and/or the rack lock of surgical instrument 250*a* to allow arm 562 of surgical instrument 250 to translate relative to arm 262 along rack 252 of surgical instrument 250 and/or to allow arm 562 of surgical instrument 250*a* to translate relative to arm 262 along rack 252 of surgical instrument 250*a*. As arm 562 of surgical instrument 250 translates relative to arm 262 along rack 252 of surgical instrument 250 and/or arm 562 of surgical instrument 250*a* translates relative to arm 262 along rack 252 of surgical instrument 250*a*, vertebra V1 pivots relative to vertebra V2 about the fulcrum provided by implant 700. Implant 700 is then disposed within vertebral space VS, as shown in FIG. 34. In some embodiments, implant 700 is configured to preserve anterior height and maintain alignment of vertebrae V. In some embodiments, the rack lock of surgical instrument 250 and/or the rack lock of surgical instrument 250*a* is/are tightened after implant 700 is disposed within vertebral space VS. In some embodiments, selectively distracting vertebrae V comprises distracting vertebrae V with one of surgical instruments 250, 250*a* and compressing vertebrae with the other one of surgical instruments 250, 250*a*.

In some embodiments, vertebrae V are selectively compressed after implant 700 is disposed within vertebral space VS. Vertebrae V are selectively compressed by loosening and/or unlocking the rack lock of surgical instrument 250 and/or the rack lock of surgical instrument 250*a* to allow arm 562 of surgical instrument 250 to translate relative to arm 262 along rack 252 of surgical instrument 250 and/or to allow arm 562 of surgical instrument 250*a* to translate relative to arm 262 along rack 252 of surgical instrument 250*a*. As arm 562 of surgical instrument 250 translates relative to arm 262 along rack 252 of surgical instrument 250 and/or arm 562 of surgical instrument 250*a* translates relative to arm 262 along rack 252 of surgical instrument 250*a*, vertebrae V compress to achieve correction, for example, a selected lordosis, as shown in FIG. 34. Vertebrae V are compressed to assist and/or cause vertebrae V to locate at a desired post-operation position, which may include assisting and/or causing vertebrae V to capture or more robustly engage implant 700. In some embodiments, capturing or more robustly engaging implant 700 comprises positioning vertebrae V at preferred angles relative to one another. In some embodiments, surgical instrument 250 and/or surgical instrument 250*a* manipulate(s) vertebrae V during a surgical correction treatment to rotate, displace, pull, twist or align vertebrae V to a selected orientation for sagittal, coronal and/or axial correction. In some embodiments, surgical instrument 250 and/or surgical instrument 250*a* apply derotation forces to vertebrae V for correction of vertebrae V. In some embodiments, the rack lock of surgical instrument 250 and/or the rack lock of surgical instrument 250*a* is/are loosened and/or unlocked after implant 700 is disposed within vertebral space VS and prior to compressing vertebrae V. In some embodiments, the rack lock of surgical instrument 250 and/or the rack lock of surgical instrument 250*a* is/are tightened and/or locked after vertebrae V are compressed. In some embodiments, selectively compressing vertebrae V comprises distracting vertebrae V with one of surgical instruments 250, 250*a* and compressing vertebrae with the other one of surgical instruments 250, 250*a*.

Figure 35:
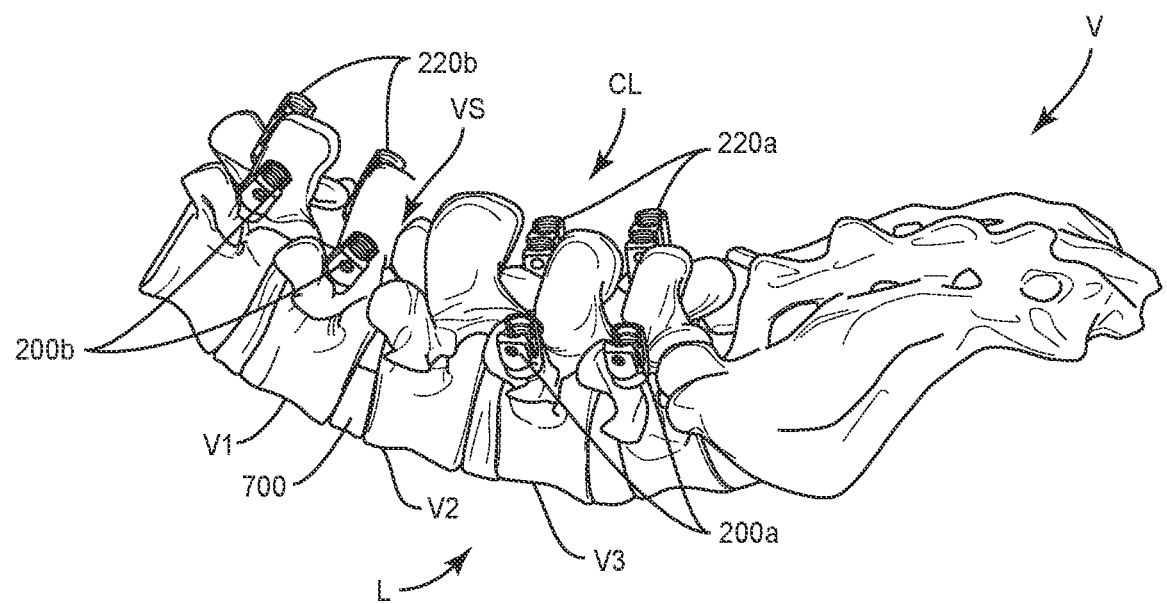
FIG. 35 is a perspective view of components of one embodiment of a surgical system in accordance with the principles of the present disclosure disposed with vertebrae.
Figure 36:
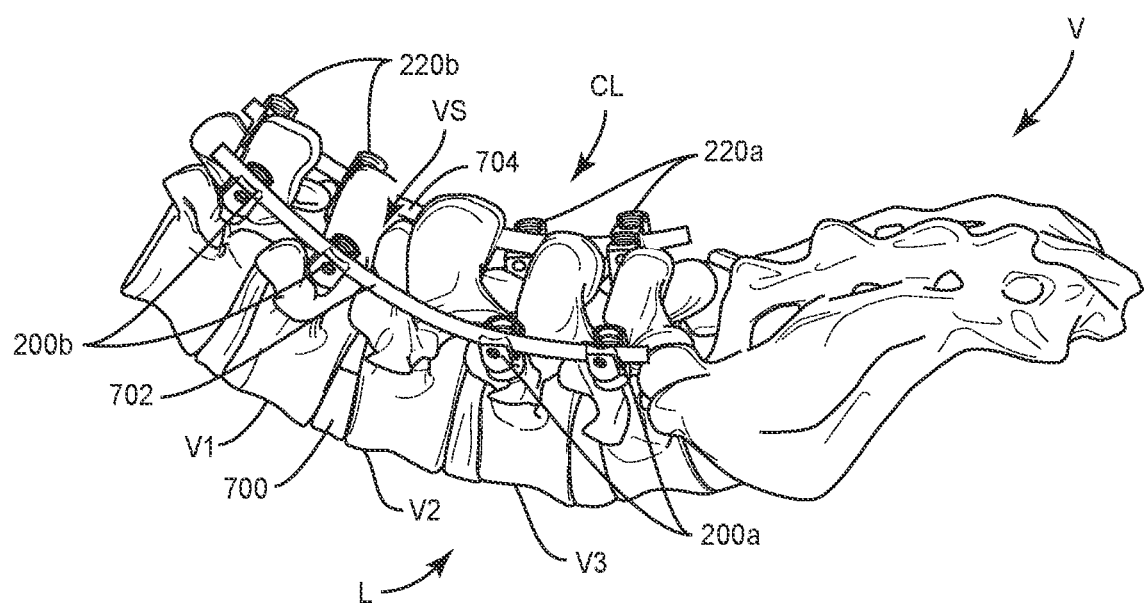
FIG. 36 is a perspective view of components of one embodiment of a surgical system in accordance with the principles of the present disclosure disposed with vertebrae.

Surgical instrument 250, surgical instrument 250*a* and spinal connectors 12, 12*a*, 12*b*, 12*c* are removed after vertebrae V are compressed to achieve selected lordosis, as shown in FIG. 35. After surgical instruments 250, 250*a* and connectors 12, 12*a*, 12*b*, 12*c* are removed, pair 200*a* is not connected to pair 200*b* and pair 220*a* is not connected to pair 220*b*, as shown in FIG. 35. Furthermore, screws 200 of pair 200*a* are not connected to one another, screws 200 of pair 200*b* are not connected to one another, screws 220 of pair 220*a* are not connected to one another and screws 220 of pair 220*b* are not connected to one another, as shown in FIG. 35. A spinal rod 702 is positioned within implant cavities of the receivers of pairs 200*a*, 200*b* and a spinal rod 704 is positioned within implant cavities of the receivers of pairs 220*a*, 220*b* to maintain selected lordosis, as shown in FIG. 36. In some embodiments, the rack lock of surgical instrument 250 and/or the rack lock of surgical instrument 250*a* is/are loosened and/or unlocked after implant 700 is disposed within vertebral space VS and before vertebrae V are compressed. In some embodiments, the rack lock of surgical instrument 250 and/or the rack lock of surgical instrument 250*a* is/are tightened and/or locked after vertebrae V are compressed and before spinal rods 702, 704 are connected with pairs 200*a*, 200*b*, 220*a*, 220*b*. In some embodiments, set screws are connected with each of screws 200, 220 such that the set screws directly engage spinal rod 702 or spinal rod 704 to maintain selected lordosis. That is, outer threads of the set screws are threaded with inner thread of receivers of screws 200, 220 to translate the set screws relative to screws 200, 220 such that the set screws directly engage spinal rod 702 or spinal rod 704 to maintain selected lordosis.

Figure 37:
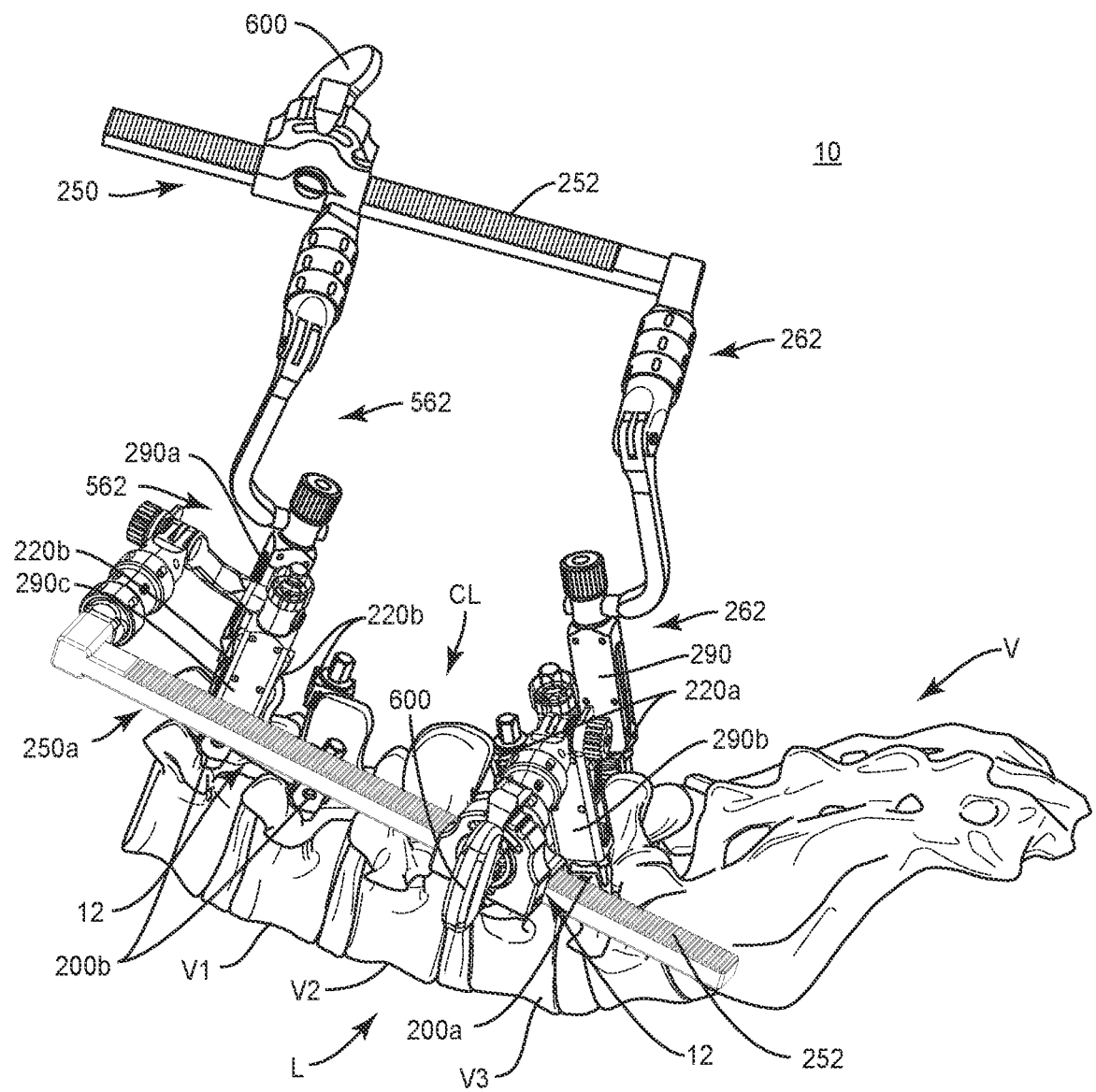
FIG. 37 is a perspective view of components of one embodiment of a surgical system in accordance with the principles of the present disclosure disposed with vertebrae.
Figure 38:
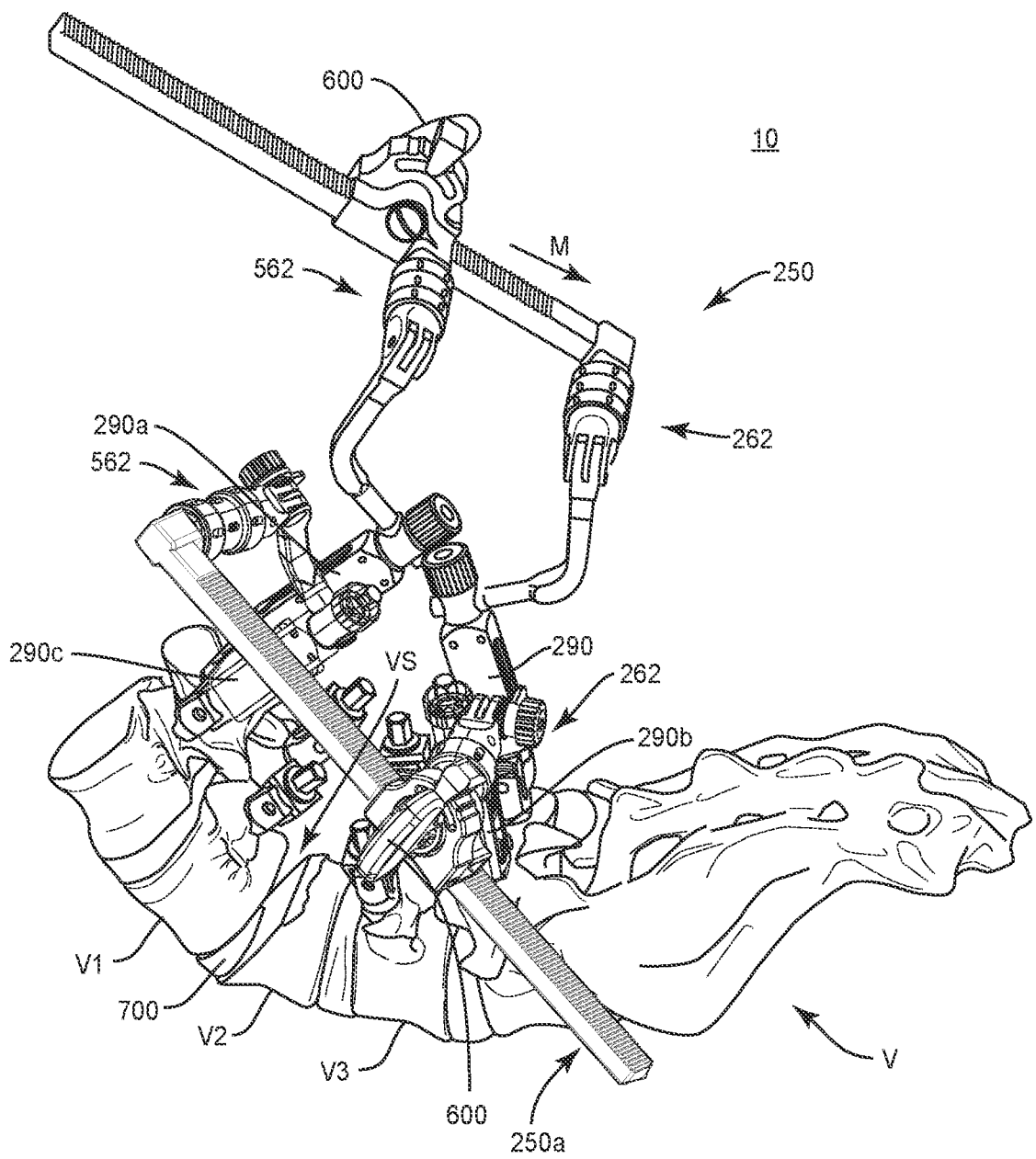
FIG. 38 is a perspective view of components of one embodiment of a surgical system in accordance with the principles of the present disclosure disposed with vertebrae.

In some embodiments, spinal rods 702, 704 may be connected with screws 200, 220 without using connectors, such as, for example, connector 12 or connector 1412. For example, in some embodiments, sleeves 290, 290*a*, 290*b*, 290*c* directly engage pairs 200*a*, 200*b*, 220*a*, 220*b*, as shown in FIG. 37. In particular, sleeve 290 directly engages one of pair 220*a*, sleeve 290*a* directly engages one of pair 220*b*, sleeve 290*b* directly engages one of pair 200*a* and sleeve 290*c* directly engages one of pair 200*b*. At least one of the joints of surgical instrument 250 and/or surgical instrument 250*a* are tightened, as discussed herein. In some embodiments, surgical instrument 250 and/or surgical instrument 250*a* are used to distract vertebrae V and a wedge portion of bone and/or other tissue is removed from a selected vertebra using an osteotome. In some embodiments, surgical instrument 250 and/or surgical instrument 250*a* are used to distract vertebrae V after vertebral space VS is formed to better accommodate a spinal implant, such as, for example, implant 700. Implant 700 is then positioned in vertebral space VS. After implant 700 is positioned in vertebral space VS, surgical instrument 250 and/or surgical instrument 250*a* is/are used to compress vertebrae V, as shown in FIG. 38. Surgical instrument 250 and surgical instrument 250*a* are removed. Spinal rod 702 is positioned within implant cavities of the receivers of pairs 200*a*, 200*b* and spinal rod 704 is positioned within implant cavities of the receivers of pairs 220*a*, 220*b* to maintain selected lordosis. Set screws are connected with each of screws 200, 220 such that the set screws directly engage spinal rod 702 or spinal rod 704 to maintain selected lordosis.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A kit for treating a spine, the kit comprising:
a first controller;
a second controller, the controllers each including:
a longitudinal element,
a first arm connected with the longitudinal element and including a body engageable with a first spinal construct, the body being rotatable relative to the first arm in a first orientation and a second orientation, the body including a lock to fix the body relative to the first arm, and
a second arm being axially translatable relative to the first arm and including a body engageable with a second spinal construct, the body of the second arm being rotatable relative to the second arm in a first orientation and a second orientation, the body of the second arm including a lock to fix the body of the second arm relative to the second arm; and
a plurality of bone fasteners,
wherein the lock of the first arm includes a collar and a screw, the first arm extending through the collar, the screw extending through the body of the first arm and into the collar.

2. A kit as recited in claim 1, further comprising:
a plurality of temporary implants; and
a plurality of permanent implants.

3. A kit as recited in claim 2, wherein the temporary implants are first spinal rods and the permanent implants are second spinal rods, the second spinal rods being different than the first spinal rods.

4. A kit as recited in claim 1, wherein the bodies each define a cavity, at least one of the bone fasteners including a head defining an implant cavity, the head being configured for disposal in one of the cavities.

5. A kit as recited in claim 1, wherein the bodies each define a cavity, at least one of the bone fasteners including a head comprising spaced apart arms, the arms defining an implant cavity therebetween, the arms being configured for disposal in one of the cavities.

6. A kit as recited in claim 1, wherein at least one of the bone fasteners includes a shaft and a receiver coupled to the shaft such that the receiver is rotatable relative to the shaft in a plurality of planes, the receiver comprising spaced apart first and second arms, the arms defining an implant cavity therebetween, the implant cavity being configured for disposal of a rod.

7. A kit as recited in claim 1, wherein at least one of the bone fasteners includes a shaft and a receiver coupled to the shaft such that the receiver is rotatable relative to the shaft in a plurality of planes, the receiver comprising first and second arms and a third arm between the first and second arms, the first and third arms defining a first implant cavity therebetween configured for disposal of a first rod, the second and third arms defining a second implant cavity therebetween configured for disposal of a second rod.

8. A kit as recited in claim 1, wherein:
rotation of the screw relative to the body of the first arm translates the collar relative to the first arm to move the body of the first arm between a first configuration in which the body of the first arm is rotatable relative to the first arm and a second configuration in which the body of the first arm is fixed relative to the first arm.

9. A kit as recited in claim 8, wherein rotation of the screw relative to the body of the first arm in a first direction moves the body of the first arm from the first configuration to the second configuration and rotation of the screw relative to the body of the first arm in an opposite second direction moves the body of the first arm from the second configuration to the first configuration.

10. A kit as recited in claim 8, wherein the screw is spaced apart from the first arm when the body of the first arm is in the first configuration and the screw directly engages the first arm when the body of the first arm is in the second configuration.

11. A kit as recited in claim 8, wherein the screw has a hexagonal head that extends through a hexagonal opening in the body of the first arm.

12. A kit as recited in claim 8, wherein the first arm extends through a first opening of the collar and the screw extends through a second opening of the collar, the second opening extending perpendicular to the first opening.

13. A kit as recited in claim 1, wherein the second arm of the first controller includes a housing, the first controller comprising a locking element pivotably connected to the housing and configured to move between a first configuration in which the second arm of the first controller is translatable along the longitudinal element of the first controller and a second configuration in which the second arm of the first controller is prevented from translating along the longitudinal element of the first controller.

14. A kit as recited in claim 1, wherein the screw is configured to directly engage the first arm.

15. A kit comprising:
a controller including a longitudinal element, a first arm connected with the longitudinal element, a second arm rotatably coupled to the first arm and a body coupled to the second arm such that the body is rotatable relative to the second arm, the body defining a cavity, the controller comprising a lock including a collar and a screw, the second arm extending through the collar, the screw extending through the body and into the collar; and
a bone fastener configured for disposal in the cavity,
wherein rotation of the screw relative to the body translates the collar relative to the body to move the body between a first configuration in which the body is rotatable relative to the second arm and a second configuration in which the body is fixed relative to the second arm.

16. A kit as recited in claim 15, wherein rotation of the screw relative to the body in a first direction moves the body from the first configuration to the second configuration and rotation of the screw relative to the body in an opposite second direction moves the body from the second configuration to the first configuration.

17. A kit as recited in claim 15, wherein the screw is spaced apart from the second arm when the body is in the first configuration and the screw directly engages the second arm when the body is in the second configuration.

18. A kit as recited in claim 15, wherein the screw has a hexagonal head that extends through a hexagonal opening in the body.

19. A kit as recited in claim 15, wherein the second arm extends through a first opening of the collar and the screw extends through a second opening of the collar, the second opening extending perpendicular to the first opening.

20. A kit comprising:
a controller including a longitudinal element, a first arm connected with the longitudinal element, a second arm rotatably coupled to the first arm and a body coupled to the second arm such that the body is rotatable relative to the second arm, the body defining a cavity, the controller comprising a lock including a collar and a screw, the second arm extending through the collar, the screw extending through the body and into the collar; and a bone fastener configured for disposal in the cavity, wherein rotation of the screw relative to the body translates the collar relative to the body to move the body between a first configuration in which the body is rotatable relative to the second arm and a second configuration in which the body is fixed relative to the second arm, wherein the screw is spaced apart from the second arm when the body is in the first configuration and the screw directly engages the second arm when the body is in the second configuration, wherein the second arm extends through a first opening of the collar and the screw extends through a second opening of the collar, the second opening extending perpendicular to the first opening, and wherein the controller includes a third arm having a housing, the controller comprising a locking element pivotably connected to the housing and configured to move between a first orientation in which the third arm is translatable along the longitudinal element and a second orientation in which the third arm is prevented from translating along the longitudinal element.

* * * * *